(12) United States Patent
Oh et al.

(10) Patent No.: US 12,569,200 B2
(45) Date of Patent: Mar. 10, 2026

(54) ELECTRONIC DEVICE FOR PROVIDING BIOMETRIC INFORMATION AND OPERATING METHOD THEREOF

(71) Applicant: SAMSUNG ELECTRONICS CO., LTD., Suwon-si (KR)

(72) Inventors: Duseon Oh, Suwon-si (KR); Donguk Kwak, Suwon-si (KR); Daehyeong Lim, Suwon-si (KR); Jaehun Cho, Suwon-si (KR); Hyunsoo Kim, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 480 days.

(21) Appl. No.: 17/993,139

(22) Filed: Nov. 23, 2022

(65) Prior Publication Data

US 2023/0165531 A1 Jun. 1, 2023

Related U.S. Application Data

(63) Continuation of application No. PCT/KR2022/018016, filed on Nov. 15, 2022.

(30) Foreign Application Priority Data

Nov. 26, 2021 (KR) ........................ 10-2021-0165173

(51) Int. Cl.
*A61B 5/00* (2006.01)
*A61B 5/0205* (2006.01)
(Continued)

(52) U.S. Cl.
CPC .......... *A61B 5/6843* (2013.01); *A61B 5/0205* (2013.01); *A61B 5/14552* (2013.01);
(Continued)

(58) Field of Classification Search
CPC ..... A61B 5/6843; A61B 5/684; A61B 5/6801; A61B 5/1455; A61B 5/14551;
(Continued)

(56) References Cited

U.S. PATENT DOCUMENTS

| | | |
|---|---|---|
| 10,265,027 B2 | 4/2019 | Lee et al. |
| 12,426,793 B2 | 9/2025 | Oh et al. |

(Continued)

FOREIGN PATENT DOCUMENTS

| | | |
|---|---|---|
| JP | 2020-130636 | 8/2020 |
| KR | 10-2006-0023003 A | 3/2006 |

(Continued)

OTHER PUBLICATIONS

International Search Report dated Feb. 21, 2023 for PCT/KR2022/018016.

(Continued)

*Primary Examiner* — Manuel L Barbee
(74) *Attorney, Agent, or Firm* — Nixon & Vanderhye P.C.

(57) ABSTRACT

An electronic device may include at least one sensor, a communication circuit, and at least one processor operatively connected with the at least one sensor and the communication circuit. The at least one processor may be configured to: if change amount of movement of the electronic device obtained via the at least one sensor is within a threshold range, identify a wearing state of the electronic device via the at least one sensor, select a group which corresponds to the wearing state from among a plurality of groups including a first group including saturations of percutaneous oxygen (SpO2s) which may correspond to reference values based on photoplethysmogram (PPG) signals and a second group including other SpO2s which may correspond to the reference values, and obtain a first PPG signal via the at least one sensor, and obtain a first SpO2

(Continued)

using the selected group and a first reference value which is based on the first PPG signal. Other embodiments are possible.

20 Claims, 19 Drawing Sheets

(51) Int. Cl.

| | |
|---|---|
| *A61B 5/024* | (2006.01) |
| *A61B 5/1455* | (2006.01) |
| *A61B 5/1495* | (2006.01) |
| *G06F 18/22* | (2023.01) |
| *H04Q 9/00* | (2006.01) |

(52) U.S. Cl.
CPC ............ *A61B 5/1495* (2013.01); *G06F 18/22* (2023.01); *H04Q 9/00* (2013.01); *A61B 5/02416* (2013.01); *A61B 5/14551* (2013.01); *A61B 5/681* (2013.01); *H04Q 2209/823* (2013.01)

(58) Field of Classification Search
CPC ... A61B 5/14552; A61B 5/6802; A61B 5/681; A61B 5/6813–6829; A61B 5/1495; A61B 5/7221; A61B 5/721; A61B 5/7214; G06F 18/22; H04Q 9/00; H04Q 2209/823
See application file for complete search history.

(56) References Cited

U.S. PATENT DOCUMENTS

| | | | |
|---|---|---|---|
| 2015/0164351 | A1 | 6/2015 | He et al. |
| 2015/0230758 | A1 | 8/2015 | Ochs |
| 2015/0289820 | A1 | 10/2015 | Miller et al. |
| 2016/0270671 | A1* | 9/2016 | Madabushi ............ G01C 23/00 |
| 2016/0274726 | A1 | 9/2016 | Chung et al. |
| 2017/0010669 | A1* | 1/2017 | Lim ........................ G06F 1/163 |
| 2017/0112398 | A1 | 4/2017 | Narusawa |
| 2017/0181680 | A1 | 6/2017 | Baek et al. |
| 2018/0042495 | A1 | 2/2018 | Moon et al. |
| 2019/0274555 | A1 | 9/2019 | Park et al. |
| 2019/0282107 | A1 | 9/2019 | Gelissen et al. |
| 2020/0113498 | A1 | 4/2020 | Bedingham |
| 2020/0146630 | A1 | 5/2020 | Joe et al. |
| 2023/0068620 | A1* | 3/2023 | Tadele ................. A61B 5/6844 |
| 2024/0118749 | A1* | 4/2024 | Holinski ................. G06F 3/038 |

FOREIGN PATENT DOCUMENTS

| | | |
|---|---|---|
| KR | 10-2016-0112559 A | 9/2016 |
| KR | 10-2017-0047848 A | 5/2017 |
| KR | 10-2020-0055933 | 5/2020 |
| KR | 10-2020-0074571 A | 6/2020 |
| KR | 10-2020-0134450 A | 12/2020 |
| KR | 10-2021-0058305 A | 5/2021 |
| KR | 10-2463076 B1 | 10/2022 |
| KR | 10-2544668 B1 | 6/2023 |
| WO | WO2020-203020 A1 | 10/2020 |
| WO | WO 2021/107871 A1 | 6/2021 |

OTHER PUBLICATIONS

PCT Written Opinion dated Feb. 21, 2023 for PCT/KR2022/018016.

Extended European Search Report dated Nov. 15, 2024 for EP Application No. 22898931.5.

Korean Office Action dated Jan. 20, 2026 for KR Application No. 10-2021-0165173.

European Examination Report dated Jan. 29, 2026 for EP Application No. 22898931.5.

\* cited by examiner

101b

220a

210a

112a

120a

250a

260a

297a

295a

270a

280a

290a

255a

293a

200

$$R \text{ value} = \frac{\dfrac{AC_{RED}}{DC_{RED}}}{\dfrac{AC_{IR}}{DC_{IR}}}$$

1300

RAW Data

1350

Removal of DC deviation
according to PD channel location

RAW Data

Removal of DC deviation according to PD channel location

1800

ELECTRONIC DEVICE FOR PROVIDING BIOMETRIC INFORMATION AND OPERATING METHOD THEREOF

CROSS-REFERENCE TO RELATED APPLICATIONS

This application is a continuation of International Application No. PCT/KR2022/018016, filed Nov. 15, 2022, designating the United States, in the Korean Intellectual Property Receiving Office, and claiming priority to Korean Patent Application No. 10-2021-0165173, filed on Nov. 26, 2021, in the Korean Intellectual Property Office, the disclosures of which are all hereby incorporated by reference herein in their entireties.

BACKGROUND

Technical Field

Certain example embodiments relate to an electronic device for providing biometric information and/or an operating method thereof.

Description of Related Art

Recently, the use of portable electronic devices such as smart phones, tablet personal computers (PCs), wearable electronic devices, etc. is increasing, and as electronic technology is developed, a technology for measuring biometric signals is also developing. For example, a technology for continuously measuring a user's biometric signals via an electronic device which may be routinely worn by the user, such as a wearable electronic device, has been developed. The wearable electronic device may include various sensors capable of measuring a user's biometric signal while being worn on the user. The wearable electronic device may provide at least one type of biometric information based on biometric signals obtained via the various sensors. For example, the wearable electronic device may measure a biometric signal (e.g., a photoplethysmogram (PPG) signal) based on an optical scheme, and may measure a biometric signal (e.g., an electrocardiography (ECG) signal) based on an electrical scheme. The wearable electronic device may provide biometric information which is based on the PPG signal, and may provide biometric information which is based on the ECG signal. The biometric information based on the PPG signal may include at least one of a heart rate (HR), body pressure, stress information (e.g., a stress index), information about a sleep state, or saturation of percutaneous oxygen (SpO2). The biometric information based on the ECG signal may include atrial fibrillation information.

In the wearable electronic device, SpO2 has been used for various health services. Schemes of measuring the SpO2 may include a first measuring scheme and a second measuring scheme. For example, the first measuring scheme may be a Continuous scheme, and the second measuring scheme may be an On-demand scheme. The On-demand scheme may be a scheme of measuring the SpO2 according to a user's request, and the Continuous scheme may be a scheme of measuring the SpO2 without a separate user request while a Continuous SpO2 measuring mode is turned on.

The SpO2 may be provided based on the PPG signal measured based on the optical scheme, and the PPG signal is obtained by measuring a change in a change rate of absorption or penetration with respect to an internal light source, this may be implemented with the PPG sensor which uses a photodiode (PD).

However, unlike a professional medical device, the wearable electronic device does not maintain close contact with a part of the user's body (e.g., the user's wrist), so external light may flow into the wearable electronic device due to sunlight or indoor light which enters through a slight gap between the wearable electronic device and the part of the user's body. Inflow of the external light via the PD may cause noise on measurement of the PPG signal.

For example, the wearable electronic device needs to measure the SpO2 in a state in which the wearable electronic device is worn on the part of the users body (e.g., the wrist) and moves along the user's body or the wearable electronic device is moved by an external force due to a characteristic of the wearable electronic device. In this case, in a case of the Continuous scheme in which SpO2 is measured without a separate user request other than the On-demand scheme in which SpO2 is measured according to a user's request, there may be a high possibility that SpO2 is measured inaccurately due to the users posture or movement. For example, the optical scheme for measuring the PPG signal may be a measuring scheme which uses light reflected corresponding to light irradiated to the part (e.g., the wrist) of the user's body, so if the Continuous scheme is used, there may be a high possibility that noise occurs on measurement of the PPG signal, and there may be a high possibility that inaccurate measurement of the PPG signal due to such noise reduces accuracy of SpO2 measurement.

SUMMARY

According to an example embodiment, an electronic device may comprise at least one sensor and at least one processor operatively connected, directly or indirectly, with the at least one sensor.

According to an example embodiment, the at least one processor may be configured to, if change amount of movement of the electronic device obtained via the at least one sensor is within a threshold range, identify a wearing state of the electronic device via the at least one sensor.

According to an example embodiment, the at least one processor may be configured to select a group which may correspond to the wearing state from among a plurality of groups including a first group including saturations of percutaneous oxygen (SpO2s) which may correspond to reference values based on photoplethysmogram (PPG) signals and a second group including other SpO2s which may correspond to the reference values.

According to an example embodiment, the at least one processor may be configured to obtain a first PPG signal via the at least one sensor, and obtain a first SpO2 using the selected group and a first reference value which is based on the first PPG signal.

According to an example embodiment, an external electronic device may comprise a communication circuit and at least one processor operatively connected, directly or indirectly, with the communication circuit.

According to an example embodiment, the at least one processor may be configured to receive, from an electronic device via the communication circuit, a first SpO2 obtained in a first measuring scheme in which a plurality of groups including a first group including saturations of percutaneous oxygen (SpO2s) which may correspond to reference values based on photoplethysmogram (PPG) signals and a second group including other SpO2s which may correspond to the reference values are used, a first reference value which may correspond to the first SpO2, an identifier of a group used for obtaining the first SpO2 among the plurality of groups, and a second SpO2 measured in a second measuring scheme in which a group (e.g., single group) is used.

According to an example embodiment, the at least one processor may be further configured to, if a difference between the first SpO2 and the second SpO2 is less than or equal to a threshold value, update a group mapped to the identifier by changing the first reference value included in the group mapped to the identifier to a second reference value which may correspond to the second SpO2.

According to an example embodiment, the at least one processor may be further configured to transmit, to the electronic device via the communication circuit, the identifier and the updated group.

According to an example embodiment, an operating method of an electronic device may comprise, if change amount of movement of the electronic device obtained via at least one sensor is within a threshold range, identifying a wearing state of the electronic device via the at least one sensor.

According to an example embodiment, the operating method may further comprise selecting a group which may correspond to the wearing state from among a plurality of groups including a first group including saturations of percutaneous oxygen (SpO2s) which may correspond to reference values based on photoplethysmogram (PPG) signals and a second group including other SpO2s which may correspond to the reference values.

According to an example embodiment, the operating method may further comprise obtaining a first PPG signal via the at least one sensor, and obtaining a first SpO2 using the selected group and a first reference value which is based on the first PPG signal.

According to an example embodiment, an operating method of an external electronic device may comprise receiving, from an electronic device, a first SpO2 obtained in a first measuring scheme in which a plurality of groups including a first group including saturations of percutaneous oxygen (SpO2s) which may correspond to reference values based on photoplethysmogram (PPG) signals and a second group including other SpO2s which may correspond to the reference values are used, a first reference value which may correspond to the first SpO2, an identifier of a group used for obtaining the first SpO2 among the plurality of groups, and a second SpO2 measured in a second measuring scheme in which a group (e.g., a single group) is used.

According to an example embodiment, the operating method may further comprise, if a difference between the first SpO2 and the second SpO2 is less than or equal to a threshold value, updating a group mapped to the identifier by changing the first reference value included in the group mapped to the identifier to a second reference value which may correspond to the second SpO2.

According to an example embodiment, the operating method may further comprise transmitting the identifier and the updated group to the electronic device.

According to an example embodiment, a non-transitory computer readable storage medium may include one or more programs, the one or more programs comprising instructions configured to, when executed by at least one processor of an electronic device, cause the electronic device to, if change amount of movement of the electronic device obtained via at least one sensor is within a threshold range, identify a wearing state of the electronic device via the at least one sensor.

According to an example embodiment, the instructions may be configured to cause the electronic device to select a group which may correspond to the wearing state from among a plurality of groups including a first group including saturations of percutaneous oxygen (SpO2s) which may correspond to reference values based on photoplethysmogram (PPG) signals and a second group including other SpO2s which may correspond to the reference values.

According to an example embodiment, the instructions may be configured to cause the electronic device to obtain a first PPG signal via the at least one sensor, and obtain a first SpO2 using the selected group and a first reference value which is based on the first PPG signal.

According to an example embodiment, a non-transitory computer readable storage medium may include one or more programs, the one or more programs comprising instructions configured to, when executed by at least one processor of an external electronic device, cause the external electronic device to, receive, from an electronic device, a first SpO2 obtained in a first measuring scheme in which a plurality of groups including a first group including saturations of percutaneous oxygen (SpO2s) which may correspond to reference values based on photoplethysmogram (PPG) signals and a second group including other SpO2s which may correspond to the reference values are used, a first reference value which may correspond to the first SpO2, an identifier of a group used for obtaining the first SpO2 among the plurality of groups, and a second SpO2 measured in a second measuring scheme in which a group (e.g., a single group) is used.

According to an example embodiment, the instructions may be configured to cause the external electronic device to, if a difference between the first SpO2 and the second SpO2 is less than or equal to a threshold value, update a group mapped to the identifier by changing the first reference value included in the group mapped to the identifier to a second reference value which may correspond to the second SpO2.

According to an example embodiment, the instructions may be configured to cause the external electronic device to transmit the identifier and the updated group to the electronic device.

DETAILED DESCRIPTION OF THE DRAWINGS

The above and other aspects, features, and advantages of certain embodiments will be more apparent from the following detailed description, taken in conjunction with the accompanying drawings, in which.

DETAILED DESCRIPTION

Figure 1A:
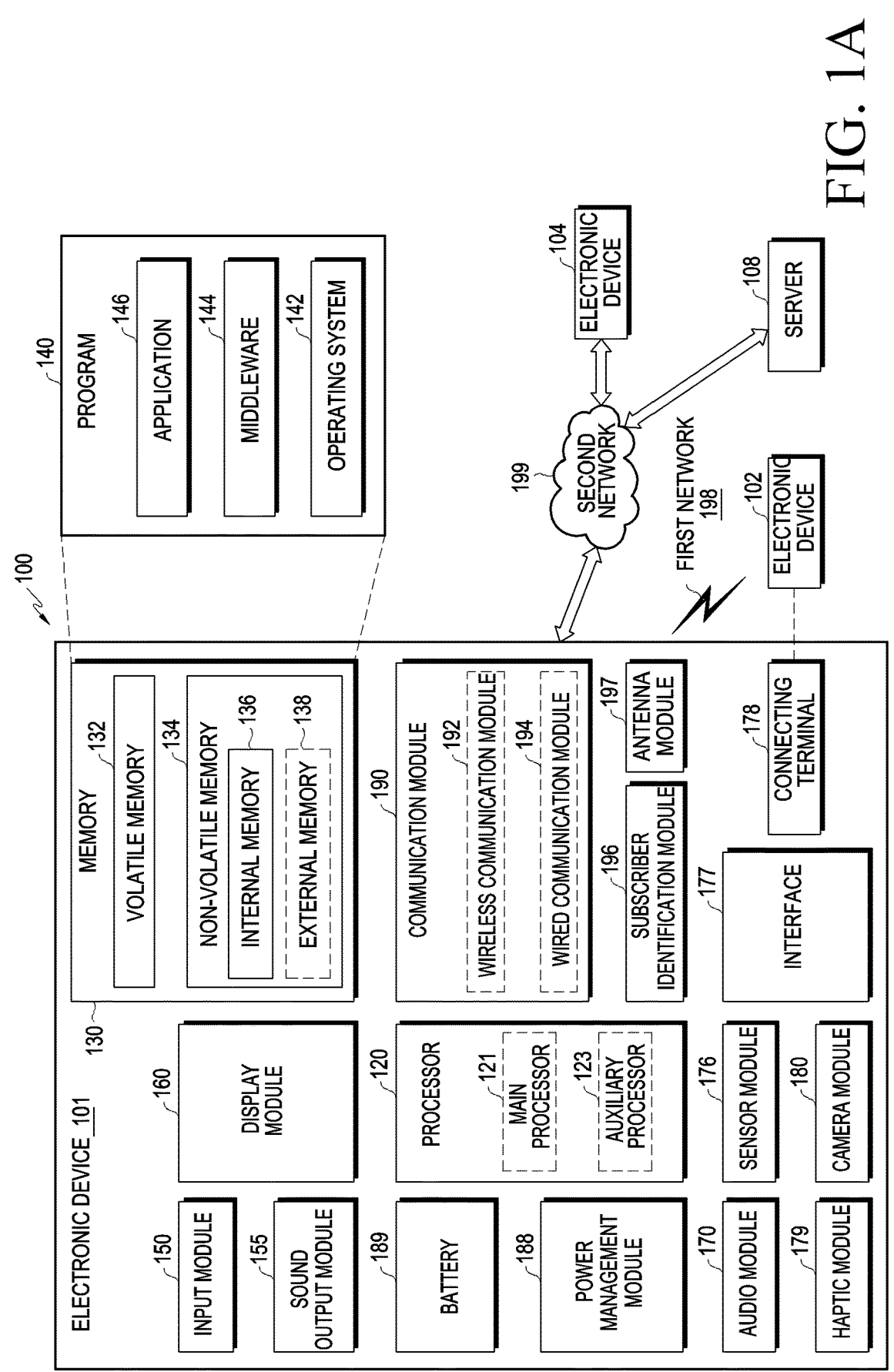
FIG. 1A is a block diagram illustrating an electronic device in a network environment according to an example embodiment.

Hereinafter, an embodiment will be described in detail with reference to the accompanying drawings. In the following description of an example embodiment, a detailed description of relevant known functions or configurations incorporated herein will be omitted when it is determined that the description may make the subject matter of an embodiment unnecessarily unclear. The terms which will be described below are terms defined in consideration of the functions in the disclosure, and may be different according to users, intentions of the users, or customs, and/or the like. Therefore, the definitions of the terms should be made based on the contents throughout the specification.

It should be noted that the technical terms used herein are only used to describe specific embodiments, and are not intended to limit the disclosure. Alternatively, the technical terms used herein should be interpreted to have the same meaning as those commonly understood by a person skilled in the art to which the disclosure pertains, and should not be interpreted have excessively comprehensive or excessively restricted meanings unless particularly defined as other meanings. Alternatively, when the technical terms used herein are wrong technical terms that cannot correctly represent the idea of the disclosure, it should be appreciated that they are replaced by technical terms correctly understood by those skilled in the art. Alternatively, the general terms used herein should be interpreted as defined in dictionaries or interpreted in the context of the relevant part, and should not be interpreted to have excessively restricted meanings.

Alternatively, a singular expression used herein may include a plural expression unless they are definitely different in the context. As used herein, such an expression as "comprises" or "include", and/or the like should not be interpreted to necessarily include all elements or all operations described in the specification, and should be interpreted to be allowed to exclude some of them or further include additional elements or operations.

Alternatively, the terms including an ordinal number, such as expressions "a first", "a second", and/or the like may be used to described various elements, but the corresponding elements should not be limited by such terms. These terms are used merely to distinguish between one element and any other element. For example, a first element may be termed a second element, and similarly, a second element may be termed a first element without departing from the scope of the disclosure.

It should be understood that when an element is referred to as being "connected" or "coupled" to another element, it may be connected or coupled directly to the other element, or any other element(s) may be interposed between them. In contrast, it should be understood that when an element is referred to as being "directly connected" or "directly coupled" to another element, there are no elements interposed between them.

Hereinafter, an example embodiment(s) will be described in detail with reference to the accompanying drawings. Regardless of drawing signs, the same or like elements are provided with the same reference numeral, and a repeated description thereof will be omitted. Alternatively, in describing an embodiment, a detailed description of relevant known technologies will be omitted when it is determined that the description may make the subject matter of the disclosure unclear. Alternatively, it should be noted that the accompanying drawings are presented merely to help easy understanding of the technical idea of the disclosure, and should not be construed to limit the technical idea of the disclosure. The technical idea of the disclosure should be construed to cover all changes, equivalents, and alternatives, in addition to the drawings.

FIG. 1A is a block diagram illustrating an electronic device in a network environment according to an embodiment.

Referring to FIG. 1A, the electronic device 101 in the network environment 100 may communicate with at least one of an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to an embodiment, as at least part of the data processing or computation, the processor 120 may store a command or data received from another component (e.g., the sensor module 176 or the communication module 190) in volatile memory 132, process the command or the data stored in volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control, for example, at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active (e.g., executing an application) state. According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence model is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input module 150, or output the sound via the sound output module 155 or an external electronic device (e.g., an electronic device 102 (e.g., a speaker or a headphone)) directly or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device 104 via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify or authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to an embodiment, the antenna module 197 may form a mmWave antenna module. According to an embodiment, the mmWave antenna module may include a printed circuit board, an RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 or 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In an embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

The electronic device according to an embodiment may be one of various types of electronic devices. The electronic devices may include, for example, a portable communication device (e.g., a smart phone), a computer device, a portable multimedia device, a portable medical device, a camera, a wearable device, or a home appliance. According to an embodiment of the disclosure, the electronic devices are not limited to those described above.

It should be appreciated that an embodiment of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "$1^{st}$" and "$2^{nd}$," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via at least a third element.

As used in connection with an embodiment of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

An embodiment as set forth herein may be implemented as software (e.g., the program 140) including one or more instructions that are stored in a storage medium (e.g., internal memory 136 and/or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to an embodiment of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to an embodiment, each component (e.g., a module or a program) of the above-described components may include a single entity or multiple entities, and some of the multiple entities may be separately disposed in different components. According to an embodiment, one or more of the above-described components or operations may be omitted, or one or more other components or operations may be added. Alternatively or additionally, a plurality of components (e.g., modules or programs) may be integrated into a single component. In such a case, the integrated component may still perform one or more functions of each of the plurality of components in the same or similar manner as they are performed by a corresponding one of the plurality of components before the integration. According to an embodiment, operations performed by the module, the program, or another component may be carried out sequentially, in parallel, repeatedly, or heuristically, or one or more of the operations may be executed in a different order or omitted, or one or more other operations may be added.

Figure 1B:
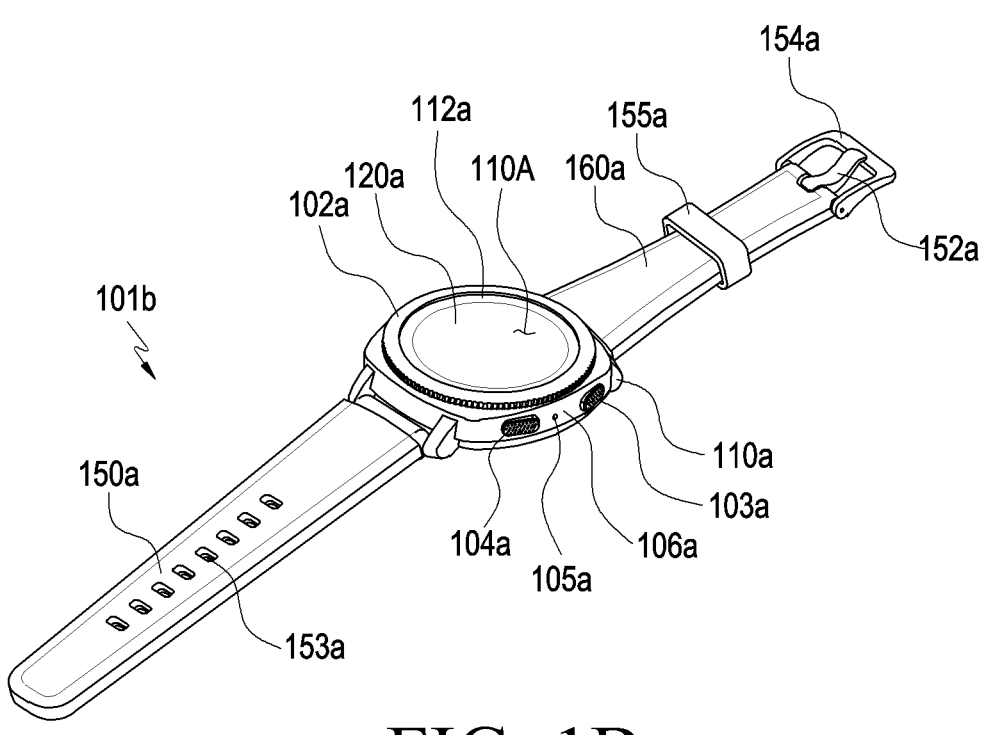
FIG. 1B is a front perspective view illustrating an electronic device according to an example embodiment.
Figure 1C:
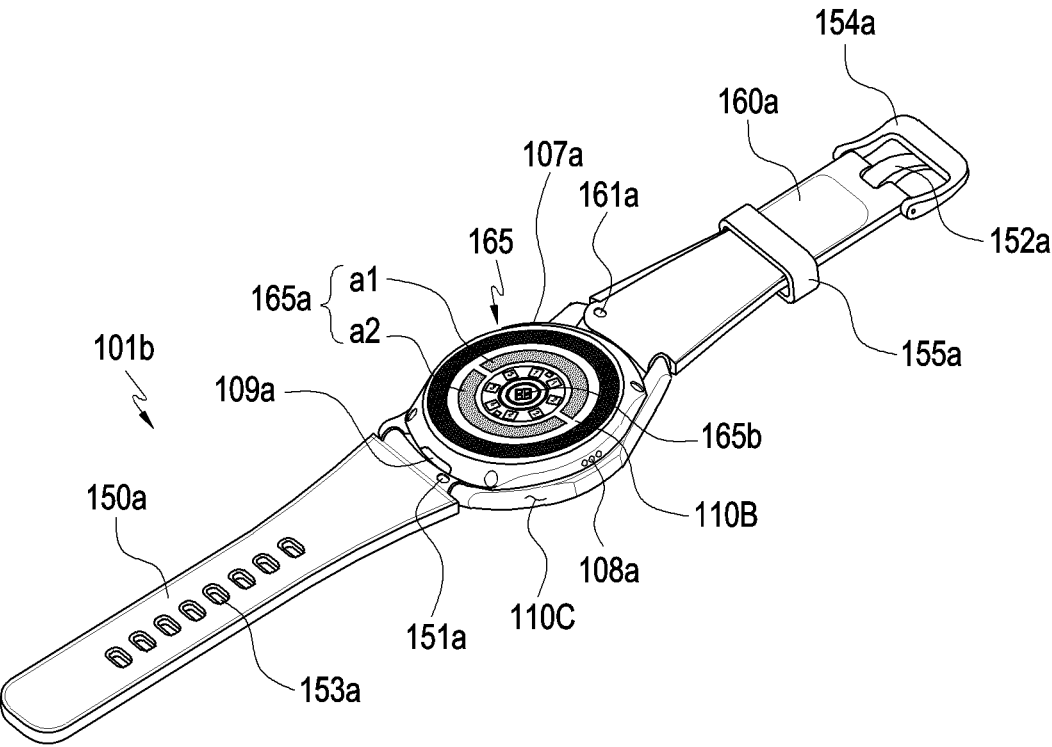
FIG. 1C is a rear perspective view illustrating an electronic device according to an example embodiment in FIG. 1B.

FIG. 1B is a front perspective view illustrating an electronic device according to an embodiment, and FIG. 1C is a rear perspective view illustrating an electronic device according to an embodiment as shown in FIG. 1B.

Referring to FIGS. 1B and 1C, according to an embodiment, an electronic device 101b (e.g., an electronic device 101 in FIG. 1A) may include a housing 110a including a first surface (or front surface) 110A, a second surface (or rear surface) 110B, and a side surface 110C surrounding a space between the first surface 110A and the second surface 110B and coupling members 150a and 160a connected to at least part of the housing 110a and configured to allow the electronic device 101b to be detachably worn on a part of a user's body (e.g., the user's wrist and the user's ankle). In an embodiment (not shown), housing may denote a structure forming a part of the first surface 110A, the second surface 110B, and the side surface 110C in FIGS. 1B and 1C. According to an embodiment, at least part of the first surface 110A may be formed of a substantially transparent front plate 112a (e.g., a glass plate or polymer plate including various coat layers). The second surface 110B may be formed of a substantially opaque rear plate 107a. In an embodiment, when the electronic device 101b includes a sensor module 165 (e.g., a sensor module 176 in FIG. 1A) disposed on the second surface 110B, the rear plate 107a may at least partially include a transparent region.

For example, the rear plate 107a may be formed of laminated or colored glass, ceramic, polymer, metal (e.g., aluminum, stainless steel (STS), or magnesium), or a combination of at least two of them. The side surface 110C may be formed by a side bezel structure (or a "side member") 106a that couples to the front plate 112a and the rear plate 107a and includes a metal and/or polymer. In an embodiment, the rear plate 107a and the side bezel structure 106a may be integrally formed together and include the same material (e.g., a metal such as aluminum). The coupling members 150a and 160a may be formed of various materials in various shapes. A uni-body structure and multiple unit links may be formed of fabric, leather, rubber, urethane, metal, ceramic, or a combination of at least two of them to be flexible one another.

According to an embodiment, the electronic device 101b may include at least one or more of a display 120a (e.g., a display module 160 in FIG. 1A), audio modules 105a and 108a (e.g., an audio module 170 in FIG. 1A), a sensor module 165 (e.g., a sensor module 176 in FIG. 1A), key input devices 102a, 103a, and 104a (e.g., an input module 150 in FIG. 1A), and a connector hole 109a. In an embodiment, the electronic device 101b may exclude at least one (e.g., the key input devices 102a, 103a, and 104a, the connector hole 109a, or the sensor module 165) of components or may add other components.

According to an embodiment, the electronic device 101b may include a plurality of electrodes for measuring a biometric signal, and at least one of the plurality of electrodes may be placed in at least one of a location of the key input device 102a, 103a, or 104a, a location of the bezel 106a, or a location of the display 120a or the housing 110a. Among the key input devices, the wheel key 102a may include a rotary bezel.

For example, the display 120a may be exposed through a substantial portion of the front plate 112a. A shape of the display 120a may be a shape corresponding to a shape of the front plate 112a, and may be one of various shapes such as a circle, an ellipse, a polygon, and/or the like. The display 120a may be coupled with, or disposed adjacent (directly or indirectly), a touch detection circuit, a pressure sensor capable of measuring the strength (e.g., pressure) of touches, and/or a fingerprint sensor.

According to an embodiment, the display 120a may include at least one transparent electrode for measuring a biometric signal among the plurality of electrodes for measuring the biometric signal.

The audio modules 105a and 108a may include a microphone hole 105a and a speaker hole 108a. The microphone hole 105a may have a microphone inside to obtain an external sound. In an embodiment, a plurality of microphones may be disposed to be able to obtain a direction of a sound in the microphone hole 105a. The speaker hole 108a may be used as an external speaker or a receiver for phone talks. In an embodiment, a speaker may be included without a speaker hole (e.g., a piezo speaker).

The sensor module 165 may generate an electrical signal or data which may correspond to an internal operating state or external environmental state of the electronic device 101b. The sensor module 165, e.g., the sensor module 165 (e.g., a heart rate monitoring (HRM) sensor) disposed on the second surface 110B of the housing 110a, may include an electrocardiography (ECG) sensor 165a including at least two electrodes a1 and a2 for ECG measurement and a photoplethysmogram (PPG) sensor 165b for heart rate measurement. The electronic device 101b may further include at least one of a gesture sensor, a gyro sensor, an atmospheric pressure sensor, a magnetic sensor, an acceleration sensor, a grip sensor, a color sensor, an infrared (IR) sensor, a temperature sensor, a humidity sensor, or an illuminance sensor.

The key input devices 102a, 103a, and 104a may include a wheel key 102a disposed on the first surface 110A of the housing 110a to be rotatable in at least one direction and/or side key buttons 103a and 104a disposed on the side surface 110C of the housing 110a. The wheel key 102a may have a shape corresponding to the shape of the front plate 112a. In an embodiment, the electronic device 101b may exclude all or some of the key input devices 102a, 103a, and 104a and the excluded key input devices 102a, 103a, and 104a may be implemented in another form, e.g., as a soft key on the display 120a. The connector hole 109a may accommodate a connector (e.g., a USB connector) for transmitting and receiving power and/or data to/from an external electronic device, and may include another connector hole (not shown) which may accommodate a connector for transmitting and receiving an audio signal to/from the external electronic device. In an embodiment, the electronic device 101b may further include a connector cover (not shown) to cover at least part of the connector hole 109a and prevent or reduce external foreign substances from entering the connector hole.

The coupling members 150a and 160a may detachably be fastened to at least portions of the housing 110a via locking members (e.g., locking members 151a and 161a in FIG. 1C). The locking members 151a and 161a may include a component for coupling, such as a pogo pin, and, according to an embodiment, may be replaced with protrusions or recesses formed on/in the coupling members 150a and 160a. For example, the coupling members 150a and 160a may be coupled, directly or indirectly, in such a manner as to be fitted into or over the recesses or protrusions formed on the housing 110a. The coupling members 150a and 160a may include one or more of a fastening member 152a, fastening member coupling holes 153a, a band guide member 154a, and a band fastening ring 155a.

The fastening member 152a may be configured to allow the housing 110a and the coupling members 150a and 160a to be fastened to the part of the user's body (e.g., the user's wrist or ankle). The fastening member coupling holes 153a may fasten the housing 110a and the coupling members 150a and 160a to the part of the user's body, corresponding to the fastening member 152a. The band guide member 154a may be configured to restrict a movement range of the fastening member 152a when the fastening member 152a fits into the fastening member coupling hole 153a, thereby allowing the coupling members 150a and 160a to be tightly fastened onto the part of the user's body. The band fastening ring 155a may limit a movement range of the coupling members 150a and 160a, with the fastening member 152a fitted into the fastening member coupling hole 153a.

Figure 1D:
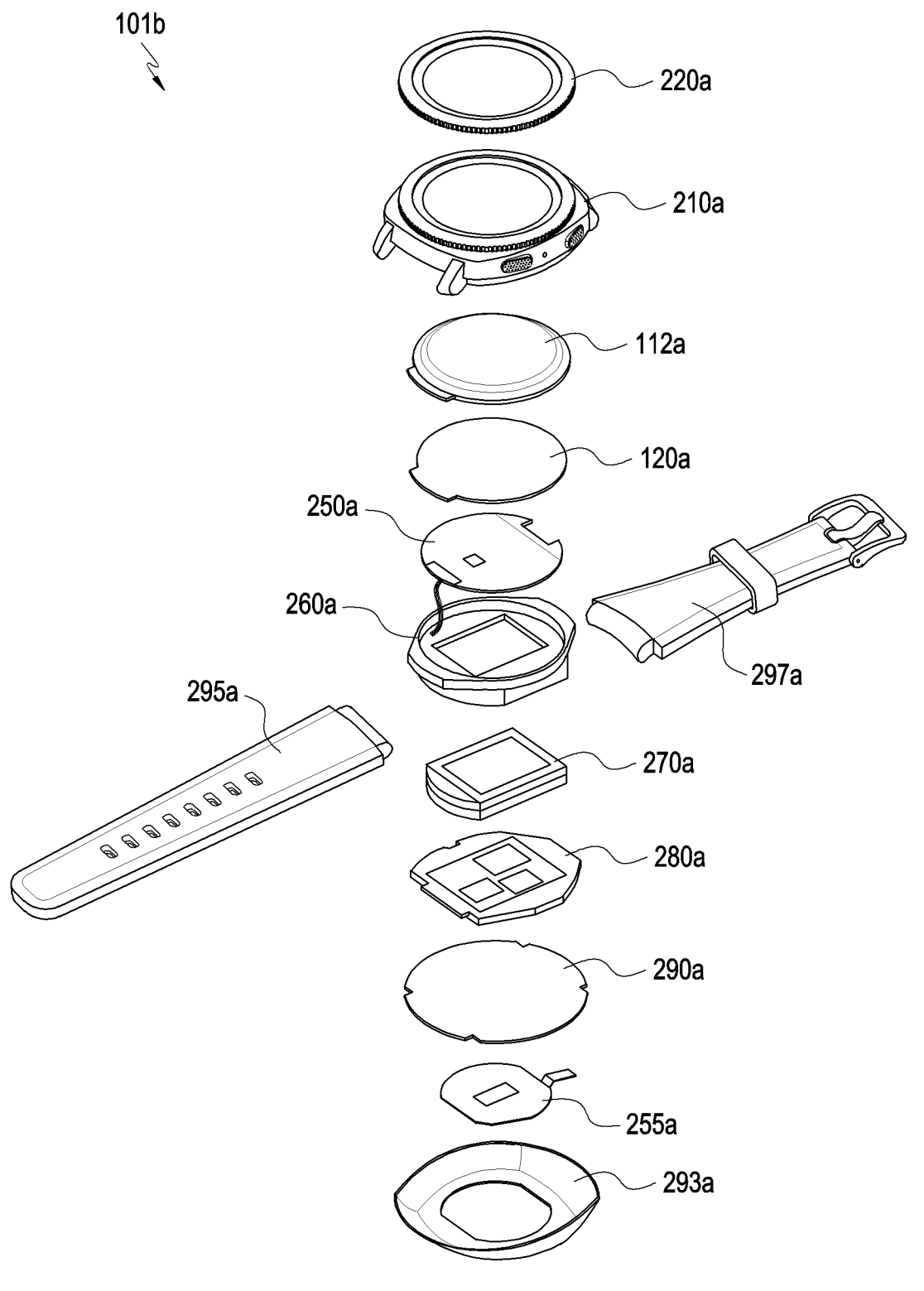
FIG. 1D is an exploded perspective view illustrating an electronic device in FIG. 1B.

FIG. 1D is an exploded perspective view illustrating an electronic device in FIG. 1B.

Referring to FIG. 1D, an electronic device 101 b (e.g., an electronic device 101 in FIG. 1A) may include a side bezel structure 210 a, a wheel key 220 a, a front plate 112 a, a display 120 a, a first antenna 250 a, a second antenna included on a second circuit board 255 a, a supporting member 260 a (e.g., a bracket), a battery 270 a, a printed circuit board 280 a, a sealing member 290 a, a rear plate 293 a, and coupling members 295 a and 297 a. At least one of the components of the electronic device 101 b may be the same or similar to at least one of the components of the electronic device 101 b of FIG. 1A or FIG. 1C and a duplicated description will be omitted. In an embodiment, the supporting member 260 a may be disposed inside the electronic device 101 b to be connected, directly or indirectly, with the side bezel structure 210 a or may be integrally formed with the side bezel structure 210 a. In an embodiment, the supporting member 260 a may be formed of a metal and/or non-metallic material (e.g., polymer). The display 120 a may be joined onto one surface of the supporting member 260 a, and the printed circuit board 280 a may be joined onto the opposite surface of the supporting member 260 a. A processor, memory, and/or interface may be mounted on the printed circuit board 280 a. In an embodiment, the processor may include at least one of a CPU, an AP, a graphic processing unit (GPU), a sensor processor, or a communication processor (CP).

In an embodiment, the memory may include a volatile or non-volatile memory. In an embodiment, the interface may include a high definition multimedia interface (HDMI), a universal serial bus (USB) interface, an SD card interface, and/or an audio interface. The interface may electrically or physically connect, directly or indirectly, e.g., the electronic device 101b with an external electronic device and may include a USB connector, an SD card/MMC connector, or an audio connector.

The battery 270a may be a device for supplying power to at least one component of the electronic device 101b, and may include a primary cell which is not rechargeable, a secondary cell which is rechargeable, or a fuel cell. At least a portion of the battery 270a may be disposed on substantially the same plane as the printed circuit board 280a. The battery 270a may be integrally or detachably disposed inside the electronic device 101b.

The first antenna 250a may be disposed between the display 120a and the supporting member 260a. The first antenna 250a may include a near-field communication (NFC) antenna, a wireless charging antenna, and/or a magnetic secure transmission (MST) antenna. The first antenna 250a may perform short-range communication with an external device, wirelessly transmit/receive power necessary for charging, or transmit magnetic-based signals including payment data or short-range communication signals. In an embodiment, an antenna structure may be formed by a portion or combination of the side bezel structure 210a and/or the supporting member 260a.

The second circuit board 255a may be disposed between the printed circuit board (PCB) 280a and the rear plate 293a. The second circuit board 255a may include an antenna, e.g., an NFC antenna, a wireless charging antenna, and/or an MST antenna. The second circuit board 255a may perform short-range communication with an external device, wirelessly transmit/receive power necessary for charging, or transmit magnetic-based signals including payment data or short-range communication signals. In an embodiment, an antenna structure may be formed by a portion or combination of the side bezel structure 210a and/or the rear plate 293a. In an embodiment, when the electronic device 101b includes a sensor module (e.g., a sensor module 176 in FIG. 1A and a sensor module 165 in FIG. 1B), a sensor element (e.g., a photoelectric conversion element or an electrode pad) separate from the second circuit board 255a or the sensor circuit disposed on the second circuit board 255a may be disposed. In an embodiment, an electronic component provided as the sensor module 165 may be disposed between the circuit board 280a and the rear plate 293a.

The sealing member 290a may be located between the side bezel structure 210a and the rear plate 293a. The sealing member 290a may be configured to block moisture or foreign substances which may enter a space surrounded by the side bezel structure 210a and the rear plate 293a, from the outside.

In an embodiment, an electronic device (e.g., a wearable electronic device) may include a sensor module (e.g., a sensor module 176 in FIG. 1A) including at least one sensor capable of measuring user's various biometric signals, and provide at least one type of biometric information based on biometric signals obtained via the sensor module. In an embodiment, a biometric signal obtained based on an optical scheme may be a PPG signal, and a biometric signal obtained based on an electrical scheme may be an ECG signal.

In an embodiment, biometric information based on a PPG signal may include at least one of a heart rate (HR), body pressure, stress information (e.g., a stress index), information about a sleep state, or saturation of percutaneous oxygen (SpO2). In an embodiment, biometric information based on an ECG signal may include atrial fibrillation information.

In an embodiment, SpO2 may be defined as in Equation 1 below.

$$SpO2\ (\%) = \frac{[O_2Hb]}{[O_2Hb] + [Hb]} \times 100 \qquad < \text{Equation 1} >$$

In Equation 1, Hb may represent a level (e.g., concentration) of hemoglobin, and O2Hb may represent a level (e.g., concentration) of oxy hemoglobin (O2Hb). SpO2 may be determined as a percentage of a level of oxy hemoglobin to sum of a level of hemoglobin and a level of oxy hemoglobin in blood. For example, an SpO2 value may be close to 100 in a healthy person.

In an embodiment, the SpO2 may be provided based on a PPG signal which is based on the optical scheme. The PPG signal may be obtained via a PPG sensor. The PPG sensor may include a light emitting unit and a light receiving unit, and the light emitting unit may include a RED light emitting diode (LED) which generates RED light (e.g., visible light having a wavelength of about 650 nm) and an infrared (IR) LED which generates IR light (e.g., infrared light having a wavelength of about 950 nm). The PPG sensor may obtain the PPG signal by irradiating, via the light emitting unit, a part of a user's body (e.g., the user's skin) with RED light and IR light, and receiving, via the light receiving unit, a signal generated by some of the irradiated RED light and IR light being reflected from the part of the user's body. The PPG signal may include a RED PPG signal including the received RED light and an IR PPG signal including the received IR light. The SpO2 may be measured based on an R value calculated according to an alternating current (AC)

component and a direct current (DC) component of each of the RED PPG signal and the IR PPG signal included in the PPG signal obtained from the PPG sensor. In an embodiment, although it has been described that the SpO2 is measured based on the R value which is based on the PPG signal, the SpO2 may be measured based on a value generated based on any one of various other biometric signals as well as the PPG signal.

In an embodiment, an algorithm based on a fast Fourier transform (FFT) and a discrete cosine transform (DCT) has been proposed for improving accuracy of the SpO2, and if 64-point FFT is applied to this algorithm with a 15 Hz sampling rate, the SpO2 may be expressed as in Equation 2 below.

$$SpO2(\%)=110-25\times R \qquad \text{<Equation 2>}$$

In Equation 2, R may be a reference value based on the PPG signal. According to an embodiment, R may be defined as in Equation 3 below.

$$R = \frac{\frac{AC_{RED}}{DC_{RED}}}{\frac{AC_{IR}}{DC_{IR}}} \qquad \text{< Equation 3 >}$$

In Equation 3, $AC_{RED}$ may represent the AC component of the RED PPG signal, $DC_{RED}$ may represent the DC component of the RED PPG signal, $AC_{IR}$ may represent the AC component of the IR PPG signal, and $DC_{IR}$ may represent the DC component of the IR PPG signal.

Each embodiment herein may be used in combination with any other embodiment described herein.

Figures 2, 3:
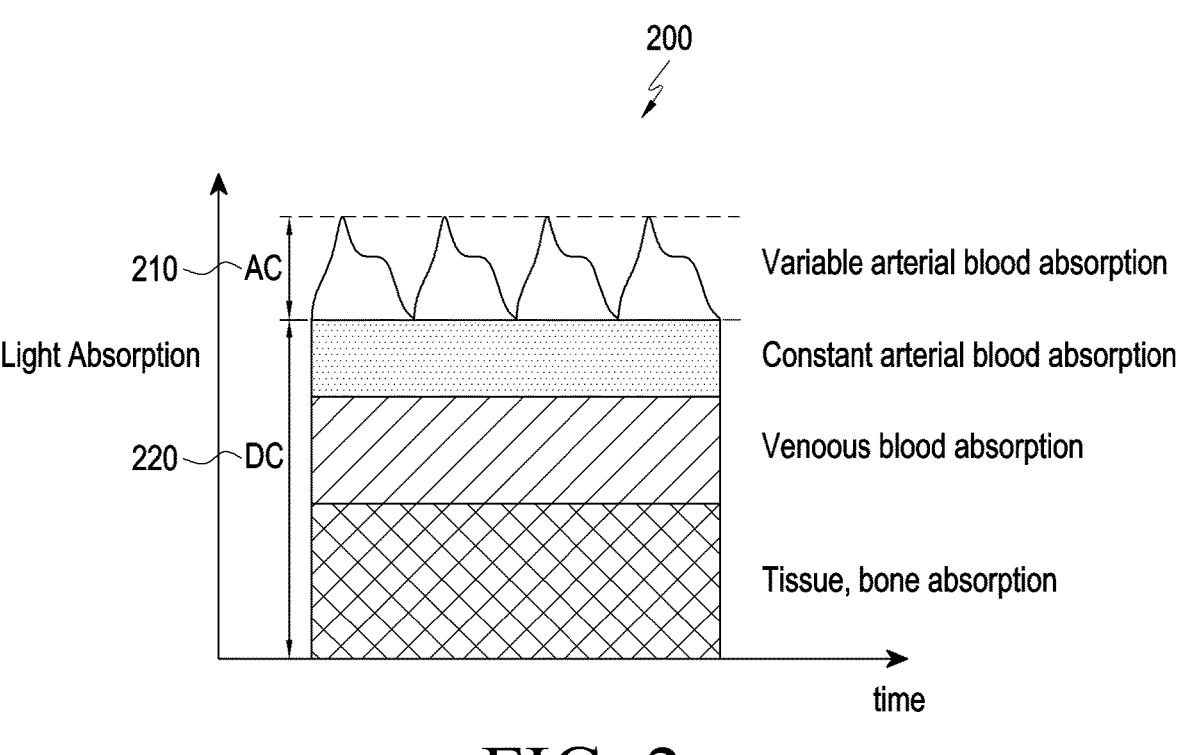
FIG. 2 is a diagram illustrating an example of an AC component and a DC component used for SpO2 measurement according to a light absorption rate according to an example embodiment.
FIG. 3 is a diagram illustrating an example of a light absorption rate according to a wavelength according to an example embodiment.

FIG. 2 is a diagram illustrating an example of an AC component and a DC component used for SpO2 measurement according to a light absorption rate according to an embodiment.

Referring to FIG. 2, in a case of light (e.g., IR light or RED light) irradiated from a light emitting unit in a PPG sensor to a part of a user's body (e.g., the user's wrist), a part thereof may be absorbed into the part of the user's body, and another part thereof may be reflected to be received via a light receiving unit in the PPG sensor. If the irradiated light is IR light, an IR PPG signal may be obtained, and if the irradiated light is RED light, a RED PPG signal may be obtained, and as described in Equation 2 and Equation 3, an R value may be obtained based on $AC_{RED}$ which is an AC component of the RED PPG signal, $DC_{RED}$ which is a DC component of the RED PPG signal, $AC_{IR}$ which is an AC component of the IR PPG signal, and $DC_{IR}$ which is a DC component of the IR PPG signal, and SpO2 may be obtained based on the obtained R value.

In a graph 200 in FIG. 2, a vertical axis may indicate amount of absorbed light (light absorption), and a horizontal axis may indicate time. In the graph 200 in FIG. 2, an AC component 210 and a DC component 220 may indicate an AC component (e.g., $AC_{IR}$) and a DC component (e.g., $DC_{IR}$), respectively, in a case that IR light is irradiated, or an AC component (e.g., ACRES) and a DC component (e.g., $DC_{RED}$), respectively, in a case that RED light is irradiated. The AC component 210 may appear as an AC waveform (e.g., variable arterial blood absorption) because absorption amount of light varies according to amount of oxygen included in blood (e.g., amount of oxygen combined with hemoglobin). The DC component 220 may be determined by components whose absorption degree of light does not vary, such as the user's cell and bone (e.g., constant arterial blood absorption, venous arterial blood absorption, and tissue, bone absorption.

FIG. 3 is a diagram illustrating an example of a light absorption rate according to a wavelength according to an embodiment.

Referring to FIG. 3, in a case of light irradiated from a light emitting unit in a PPG sensor to a part of a user's body (e.g., the user's wrist), a part thereof may be absorbed into the part of the user's body, and another part thereof may be reflected to be received via a light receiving unit in the PPG sensor. Amount of change in amount of reflected light may be affected by oxygen combined with hemoglobin.

In a graph shown in FIG. 3, a vertical axis may indicate absorbance, and a horizontal axis may indicate a wavelength. In an embodiment, in a case of a wavelength (650 nm) of IR light and a wavelength (950 nm) of RED light, there is a large difference in a light absorption rate in deoxy hemoglobin (DeoxyHb) 310 and oxy hemoglobin (OxyHb) 320, so an R-Curve based on an R value may be generated using two wavelengths. For example, in the graph 300 in FIG. 3, for the RED light, a light absorption rate of the DeoxyHb 310 may be higher than a light absorption rate of the OxyHb 320, and for the IR light, a light absorption rate of the OxyHb 320 may be higher than a light absorption rate of the DeoxyHb 310. So, a reference device for measuring the SpO2 may generate an R-Curve indicating a correlation between an R value and the SpO2 through a calibration process.

In an embodiment, the reference device for measuring the SpO2 will be referred to as a reference SpO2 measuring device. The reference SpO2 measuring device may be a medical SpO2 measuring device. In an embodiment, the reference SpO2 measuring device is not necessarily the medical SpO2 measuring device, and there is no limitation on a type of a device as long as it may accurately measure the user's SpO2.

Figure 4:
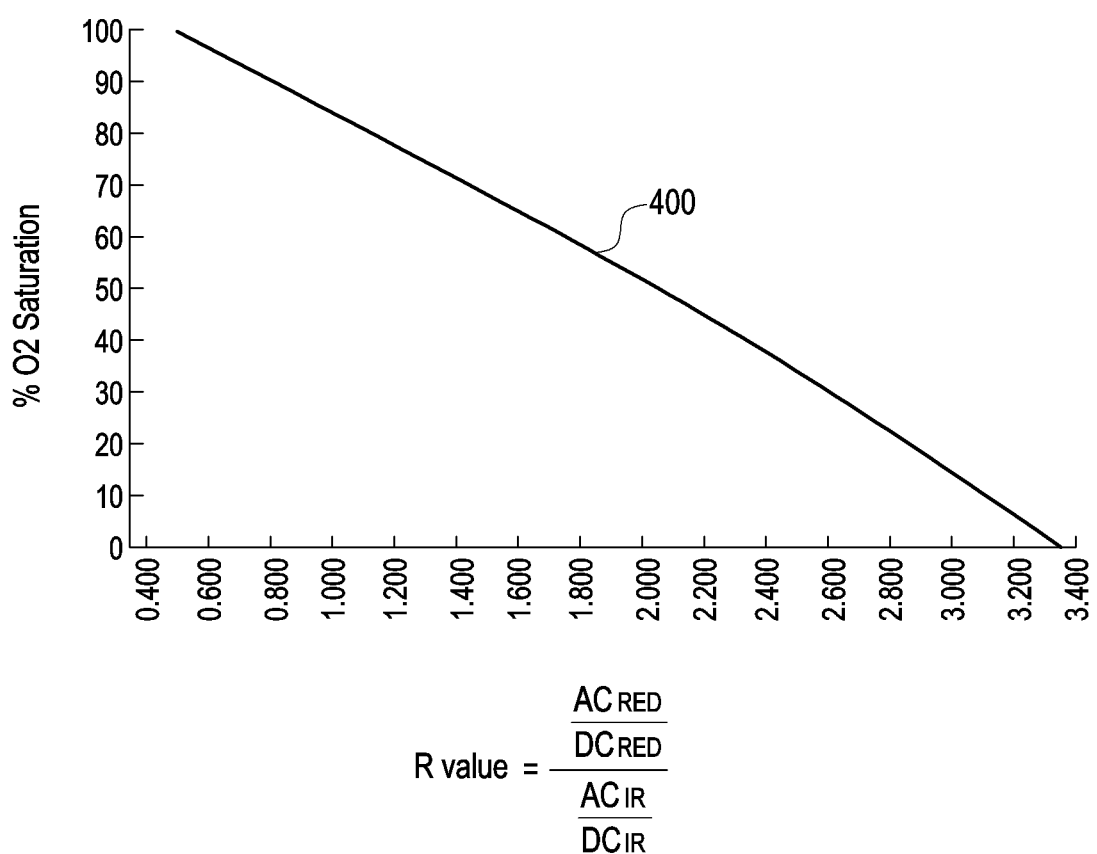
FIG. 4 is a diagram illustrating an example of an R-Curve used for SpO2 measurement according to an example embodiment.

FIG. 4 is a diagram illustrating an example of an R-Curve used for SpO2 measurement according to an embodiment.

Referring to FIG. 4, a graph 400 illustrated in FIG. 4 may indicate an R-Curve, a vertical axis may indicate SpO2 (% O2 Saturation), and a horizontal axis may indicate an R value. As illustrated in FIG. 4, an R-Curve 400 used for SpO2 measurement may be a correlation between an R value identified based on a PPG signal outputted from a PPG sensor and SpO2. In an embodiment, the R-Curve 400 may be a group including pairs of an R value and SpO2. In an embodiment, the correlation between the R value and the SpO2 has been indicated by taking the R-Curve 400 as an example, but the correlation between the R value and the SpO2 may be indicated as a table including the pairs of the R value and the SpO2.

In an electronic device (e.g., a wearable electronic device (e.g., an electronic device 101 in FIG. 1A)), SpO2 may be used for various health services. Schemes for measuring the SpO2 may include a first measuring scheme and a second measuring scheme. For example, the first measuring scheme may be a Continuous scheme, and the second measuring scheme may be an On-demand scheme. The On-demand scheme may be a scheme of measuring the SpO2 according to a user's request. The Continuous scheme may be a scheme of continuously measuring the SpO2 without a separate user request while a Continuous measuring mode is turned on, and in the Continuous scheme, a plurality of R-Curves may be used. For example, in the Continuous scheme, a plurality of groups may be used, each including pairs of an R value and SpO2.

For example, the On-demand scheme may be a scheme of measuring the SpO2 when a user request (e.g., an input by which a user touches a menu to start SpO2 measurement) is received in, for example, the electronic device 101 of FIG. 1A (e.g., a scheme of measuring the SpO2 until valid SpO2 measurement is completed), and the Continuous scheme may be a scheme of continuously measuring the SpO2 based on a designated period (e.g., one hour) until SpO2 measurement is deactivated in a state that the SpO2 measurement is activated. For example, activation of the SpO2 measurement may indicate that at least some of the PPG sensor, at least one software module for measuring the SpO2, and/or a function for measuring the SpO2 are activated. For example, the On-demand scheme may be used when the user measures the SpO2 while being in a stable posture to measure the SpO2, and the Continuous scheme may be used for continuously measuring the SpO2 without a separate user request, such as during sleep. An R-Curve used in the On-demand scheme and an R-Curve used in the Continuous scheme may be the same. An R-Curve used in both the On-demand scheme and the Continuous scheme may be an R-Curve generated by a reference SpO2 measuring device. For example, the R-Curve used in both the On-demand scheme and the Continuous scheme may be an R-Curve generated by measuring the SpO2 by the reference SpO2 measuring device in an appropriate measurement state (e.g., a state in which a measurement portion of the reference SpO2 measuring device is in close contact with the user's body) in a state in which the user's movement is relatively little.

In the Continuous scheme, when it is not a state in which the user intends the SpO2 measurement, the SpO2 may be continuously measured in various usage environments (e.g., the user's posture). So, if the SpO2 is measured through a wearable electronic device based on an R-Curve generated in a state in which the user is taking a stable posture in the Continuous scheme through the reference SpO2 measuring device, the measured SpO2 may be inaccurate. Unlike the reference SpO2 measuring device which is a professional medical device, the wearable electronic device does not maintain close contact with a part of the user's body (e.g., the user's wrist), so external light may flow into the wearable electronic device due to sunlight or indoor light which enters through a slight gap between the wearable electronic device and the part of the user's body. Like this, not only light generated from an internal light source but also light generated from the outside are inputted in a photodiode (PD) included in a light receiving unit in a PPG sensor, and this may cause noise on measurement of a PPG signal. Hereinafter, for convenience of a description, the wearable electronic device will be described in a form of a watch worn on the user's wrist, but a type of the wearable electronic device is not limited. For example, the wearable electronic device may be an electronic device in a form of glasses worn on the user's face.

For example, the wearable electronic device may need to meet at least one condition among the following condition (1) and condition (2) in order to measure the SpO2 from the user's body (e.g., the wrist).
(1) PPG Sensor Setting
The PPG sensor may be set to satisfy at least one of the following conditions so that a relatively high (e.g., higher than or equal to a threshold value) signal to noise ratio (SNR) may be secured to measure the SpO2.
Sample rate of a RED LED and/or an IR LED which is greater than or equal to 100 hz

Relatively wide (e.g., greater than or equal to a threshold value) LED pulse width
Use of relatively large (e.g., greater than or equal to a threshold value) current of an IR LED and an RED LED
(2) Wearing State
State in which the wearable electronic device is worn to closely adhere to the part (e.g., the wrist) of the user's body in a state in which movement of the part of the user's body is relatively small
In an embodiment, if a size of an area in which the wearable electronic device is in contact with the part of the user's body is larger than or equal to a threshold area, it may indicate a state in which the wearable electronic device is worn to closely adhere to the part of the user's body.
Wearing state similar to or substantially the same as a wearing state applied when an R-Curve is generated (e.g., used in an R-Curve calibration process)
In an embodiment, the wearing state may be a state indicating in what form the wearable electronic device is worn on the part of the user's body. According to an embodiment, the wearing state may be a state not indicating that the wearable electronic device is worn on the part of the user's body itself, but indicating in what form the wearable electronic device is worn on the part of the user's body. In an embodiment, the wearing state may be identified based on at least one wearing state signal obtained via a sensor module included in the wearable electronic device, and information indicating the wearing state will be referred to as wearing state information. The wearing state information may include at least one information element, and each of the at least one information element may indicate a wearing state which may correspond to a wearing state signal. For example, if the wearing state information includes three information elements, the three information elements may include pressure applied between the wearable electronic device and the part of the user's body, the size of the area in which the wearable electronic device is in contact with the part of the user's body, and a direction in which the wearable electronic device is in contact with the part of the user's body.

In an embodiment, the wearing state of the wearable electronic device may be determined by at least one of pressure applied to the part of the user's body by the wearable electronic device and/or a location of the wearable electronic device. Biometric information based on the PPG signal may include at least one of a heart rate (HR), body pressure, stress information (e.g., a stress index), information about a sleep state, or SpO2, and PPG sensor setting and a wearing state required to measure each of the HR and the SpO2 among them may be compared as shown in Table 1 below.

TABLE 1

| | | HR | SpO2 |
|---|---|---|---|
| PPG Sensor Setting | LED Sample Rate | 25 Hz | 100 Hz |
| | Pulse Width | About 70 us | About 170 us |
| | LED Current | 80 mA | 100 mA or more |
| Others | Wearing State | Normal | Important |
| | Whether to Calibrate | DC correction is required | R-Curve Calibration is required |

As shown in Table 1, if the SpO2 is measured, compared to a case that other biometric information (e.g., the HR) is measured, there are more complicated aspects in terms of the PPG sensor setting, the wearing state, and calibration, so it may be inefficient to always execute the SpO2 measuring mode to provide a health service related to the SpO2. Even if the SpO2 measuring mode is not always executed and the SpO2 measuring mode is executed as necessary, if the Continuous scheme is used, there may be a high possibility that the SpO2 will be inaccurately measured. If the Continuous scheme is used, for example, even if the user's movement is very small due to sleep, a wearing state (e.g., at least a part of wearing state information) of the electronic device may change as the part (e.g., the wrist) of the user's body on which the wearable electronic device is worn is pressed or pushed according to the user's sleeping posture. Due to this, there may be a high possibility that the SpO2 will be inaccurately measured.

Figure 5:
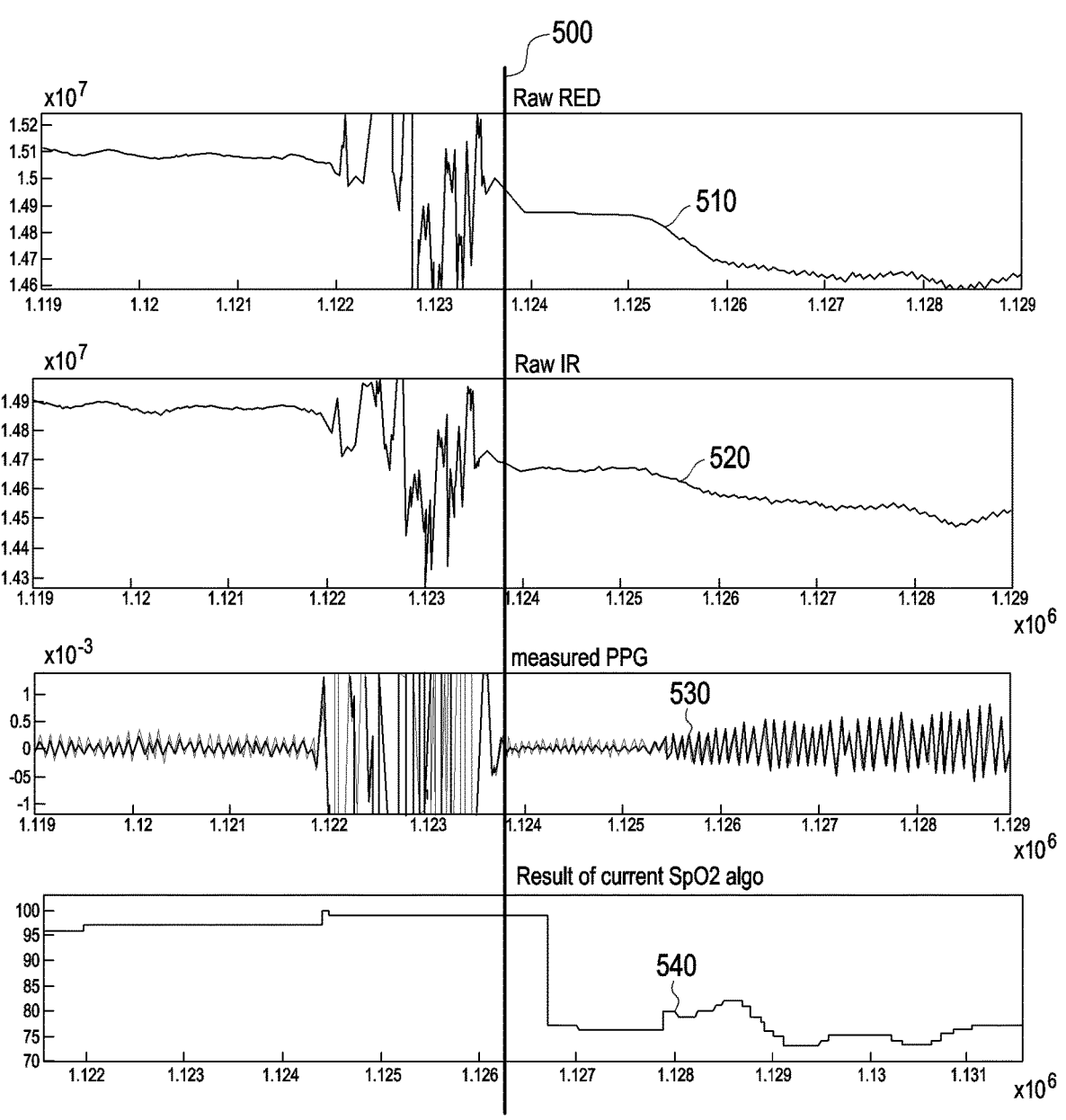
FIG. 5 is a diagram illustrating an example of an SpO2 measurement error according to a change in a wearing state of a user's electronic device in a case that a Continuous scheme is used according to an example embodiment.

FIG. 5 is a diagram illustrating an example of an SpO2 measurement error according to a change in a wearing state of a user's electronic device in a case that a Continuous scheme is used according to an embodiment.

Referring to FIG. 5, in a state in which SpO2 is measured in a Continuous scheme in an SpO2 measuring mode, raw data 510 of RED light and raw data 520 of IR light which are generated from a PPG sensor may rapidly change according to a change in a state in which a user wears an electronic device (e.g., a wearable electronic device)(e.g., an electronic device 101 in FIG. 1A). In an embodiment, a wearing state may indicate how much pressure the wearable electronic device is in contact with a part of the user's body, how wide the wearable electronic device is in contact with the part of the user's body, in which direction the wearable electronic device is in contact with the part of the user's body, or how evenly the wearable electronic device is in contact with the part of the user's body. For example, a change in the wearing state may be or include a change in at least part of pressure applied between the part of the user's body and the wearable electronic device, a size of an area in which the wearable electronic device is in contact with the part of the user's body, and a direction in which the wearable electronic device is in contact with the part of the user's body. For example, if there are two wearing states, a first wearing state and a second wearing state, at least part of pressure applied between the part of the user's body and the wearable electronic device, a size of an area in which the wearable electronic device is in contact with the part of the user's body, and a direction in which the wearable electronic device is in contact with the part of the user's body which may correspond to the first wearing state may be different from at least part of pressure applied between the part of the user's body and the wearable electronic device, a size of an area in which the wearable electronic device is in contact with the part of the user's body, and a direction in which the wearable electronic device is in contact with the part of the user's body which may correspond to the second wearing state.

In an embodiment, a reference numeral 500 in FIG. 5 may indicate a time point at which the user's wearing state changes in the state in which the SpO2 is measured in the Continuous scheme in the SpO2 measuring mode. A magnitude of an AC component of an RED PPG signal and a magnitude of an AC component of an IR PPG signal change due to a rapid change in the raw data 510 of the RED light and the raw data 520 of the IR light according to the change in the user's wearing state, so a PPG signal 530 measured in the PPG sensor may also change rapidly according to the change in the user's wearing state.

As the PPG signal 530 rapidly changes, SpO2 540 measured based on a PPG signal also rapidly changes, and this may be SpO2 which is inaccurately measured according to the change in the user's wearing state, not the user's actual SpO2.

A device for measuring SpO2 (e.g., an SpO2 measuring device) may need to perform a Calibration process for generating an R-Curve according to a structure and a characteristic of a PPG sensor. In a reference SpO2 measuring device (e.g., a medical SpO2 measuring device) for measuring SpO2 in a penetration type, constant pressure is applied to a part of a user's body (e.g., the user's finger) in a clip type, and a Calibration process may be performed using a reference SpO2 (Ref SpO2) and an R value which is measured in a state in which the constant pressure is applied to the part of the user's body.

In the Continuous scheme, if SpO2 is measured using an R-Curve generated according to the Calibration process in a stable wearing state and the wearing state of the user of the wearable electronic device becomes unstable, inaccurate SpO2 may be measured.

It may be undesirable for a wearable electronic device to operate in an SpO2 measuring mode for measuring SpO2 in a situation in which there is a high probability that inaccurate SpO2 is measured due to a limited resource (e.g., a relatively small battery capacity, and a relatively small memory capacity). For example, if pressure is applied to the wearable electronic device in a vertical direction, density of skin and cells irradiated with light via a PPG sensor may change, so an R value obtained via the PPG sensor may change. If SpO2 is measured by applying the changed R value to an R-Curve generated according to a Calibration process in a stable wearing state, inaccurate SpO2 may be measured.

Hereinafter, an embodiment of an electronic device (e.g., a wearable electronic device) for providing biometric information (e.g., SpO2) and an operating method thereof will be described in detail with reference to the drawings.

An embodiment proposes a device and a method for generating a plurality of R-Curves mapped to a plurality of wearing states of a user in advance, selecting an R-Curve which may correspond to a wearing state of the user from among the plurality of R-Curves, and measuring SpO2 which may correspond to the selected R-Curve. In an embodiment, an R-Curve may be a group including pairs of an R value and SpO2. In an embodiment, a correlation between the R value and the SpO2 may be indicated by taking the R-Curve as an example, but the correlation between the R value and the SpO2 may be indicated/provided as a table including the pairs of the R value and the SpO2. In an embodiment, the plurality of R-Curves may be updated if necessary. In an embodiment, a unique identifier (ID) (or index) may be allocated to each of the plurality of R-Curves. In an embodiment, a unique ID (or index) may be allocated to each of a plurality of tables.

In an embodiment, a wearing state may indicate a state in which a wearable electronic device is worn on a part of a user's body (e.g., the user's wrist). In an embodiment, the wearing state may indicate how much pressure the wearable electronic device is in contact with the part of the user's body, how wide the wearable electronic device is in contact with the part of the user's body, in which direction the wearable electronic device is in contact with the part of the user's body, or how evenly the wearable electronic device is in contact with the part of the user's body. In an embodiment, the wearing state may be identified based on at least one wearing state signal obtained via a sensor module which is included in the wearable electronic device and includes at least one sensor, and information indicating the wearing state will be referred to as wearing state information. The wearing state information may include at least one information element, and each of the at least one information element may indicate a wearing state which may correspond to a wearing state signal. For example, if the wearing state information includes three information elements, the three information elements may include pressure applied between the wearable electronic device and the part of the users body, the size of the area in which the wearable electronic device is in contact with the part of the user's body, and a direction in which the wearable electronic device is in contact with the part of the users body.

In an embodiment, the wearable electronic device may include a sensor module including at least one sensor capable of measuring users various biometric signals, and provide at least one type of biometric information based on biometric signals obtained via the sensor module. In an embodiment, a biometric signal obtained based on an optical scheme may be a PPG signal, and a biometric signal obtained based on an electrical scheme may be an ECG signal. In an embodiment, biometric information based on a PPG signal may include at least one of an HR, body pressure, stress information (e.g., a stress index), information about a sleep state, or SpO2. In an embodiment, biometric information based on an ECG signal may include atrial fibrillation information.

Figure 6:
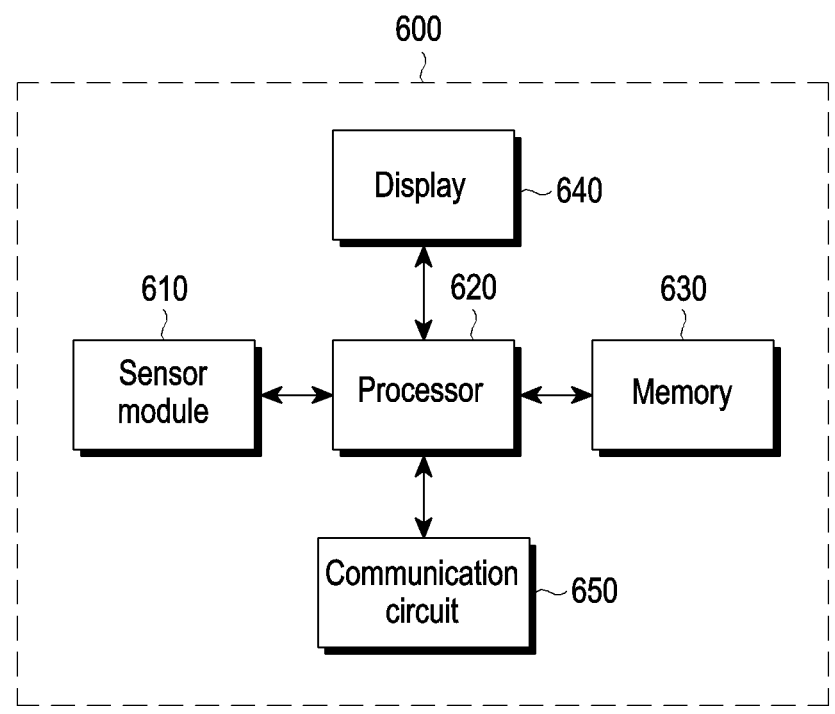
FIG. 6 is an example of a block diagram illustrating an electronic device according to an example embodiment.

FIG. 6 is an example of a block diagram illustrating an electronic device according to an embodiment.

Referring to FIG. 6, an electronic device 600 (e.g., an electronic device 101 in FIG. 1A or an electronic device 101b in FIG. 1B to FIG. 1D) may be a device for providing biometric information, and may be a wearable electronic device (e.g., a watch). In an embodiment, the biometric information may be SpO2.

Referring to FIG. 6, the electronic device 600 (e.g., the electronic device 101 in FIG. 1A or the electronic device 101b in FIG. 1B to FIG. 1D) may include a sensor module 610 (e.g., a sensor module 176 in FIG. 1A or a sensor module 165 in FIG. 1B), a processor 620 (e.g., a processor 120 in FIG. 1A), a memory 630 (e.g., a memory 130 in FIG. 1A), a display 640 (e.g., a display module 160 in FIG. 1A, or a display 120a in FIG. 1B or FIG. 1D), and a communication circuit 650 (e.g., a communication module 190 in FIG. 1A).

The sensor module 610 may include at least one sensor, and may obtain at least one biometric signal via the at least one sensor. In an embodiment, the at least one sensor may include other sensors which may be needed to measure a biometric signal such as an acceleration sensor as well as a biometric sensor such as an ECG sensor, a PPG sensor, a heart rate measuring sensor, and a body temperature measuring sensor, and types of a plurality of sensors may not be limited thereto. In an embodiment, the at least one sensor may include at least one of an acceleration sensor, a gyro sensor, and a pressure sensor.

In an embodiment, the PPG sensor may include a light emitting unit and a light receiving unit, and the light emitting unit may include an RED LED which generates RED light (e.g., visible light having a wavelength of about 650 nm) and an IR LED which generates IR light (e.g., infrared light having a wavelength of about 950 nm). The PPG sensor may be a sensor for estimating various biometric states based on a characteristic of a living body or a blood flow flowing inside the living body by irradiating, via the light emitting unit, a part of a user's body (e.g., the user's wrist) with RED light and IR light and receiving, via the light receiving unit, a signal generated by some of the irradiated RED light and IR light being reflected from the part of the user's body to obtain a PPG signal. According to an embodiment, if the PPG sensor is used, various biometric information which is based on a heart rate as well as the heart rate may be obtained. For example, the PPG sensor may generate and receive light having various wavelengths, so the PPG sensor may be used for measuring SpO2.

According to an embodiment, if the sensor module 610 includes a plurality of sensors, when an ECG signal is measured, acceleration and SpO2 may also be measured. Blood pressure may be measured based on the ECG signal and the PPG signal, and for example, sleep apnea symptoms may be measured based on the acceleration and the SpO2. For example, if the user breathes based on an acceleration value obtained from an acceleration sensor, a change in height of the user's chest and the user's toss and turn may be identified, and a sleep apnea state may be identified based on the SpO2 which is measured based on the PPG signal obtained via the PPG sensor.

According to an embodiment, the sensor module 610 may include a light emitting unit and a light receiving unit, and a sensor including the light emitting unit and the light receiving unit may be referred to as a PPG sensor. According to an embodiment, the sensor module 610 may irradiate, via the light emitting unit, the part of the user's body with light having a specific wavelength band. According to an embodiment, the light emitting unit may irradiate the part of the user's body with light having a certain intensity, and a wavelength of the irradiated light may vary according to a measurement purpose or a type of target component to be analyzed. According to an embodiment, the light emitting unit may include at least one of an LED and a laser diode (LD). For example, the light emitting unit may use bands having various wavelengths such as GREEN light, RED light, BLUE light, or IR light to reduce effect of a motion artifact, and emit light with a scheme of turning on a plurality of wavelengths at the same time, or crossing and turning on the plurality of wavelengths. Each light emitting unit herein may comprise a light source.

The sensor module 610 may detect, via the light receiving unit, light reflected from the part of the user's body or penetrated through the part of the user's body corresponding to the irradiated light. The sensor module 610 may output, via the light receiving unit, a biometric signal which may correspond to the light reflected from the part of the user's body. Each sensor module herein comprises at least one sensor.

According to an embodiment, the light receiving unit in the sensor module 610 may receive the reflected light to generate at least one biometric signal using an electrical signal converted from the light, and the at least one biometric signal may be a PPG signal. According to an embodiment, the light receiving unit may include a photodiode (PD), a photo transistor, or a charge-coupled device (CCD), and a type of a device may not be limited thereto as long as it is a device capable of converting an optical signal into an electrical signal. According to an embodiment, a structure of the light receiving unit may be a reflective structure or a penetrated structure.

According to an embodiment, the sensor module 610 may receive a current which corresponds to a measured PPG signal, and may convert the measured PPG signal into a digital signal to transmit the digital signal to the processor 620. According to an embodiment, the sensor module 610 may perform current-voltage conversion for processing the PPG signal, and digitize an analog voltage signal which is outputted before transfer to the processor 620 to transfer it to the processor 620.

The processor 620 may generate and provide biometric information based on a biometric signal from the sensor module 610. According to an embodiment, the processor 620 may be operatively connected, directly or indirectly, to the sensor module 610 and may control to irradiate the part of the user's body with light via the light emitting part of the sensor module 610.

According to an embodiment, the processor 620 may detect, predict, or analyze a health state of the user based on a biometric signal provided from the sensor module 610. According to an embodiment, the processor 620 may provide at least one biometric information based on the biometric signal provided from the sensor module 610. In an embodiment, the biometric signal provided from the sensor module 610 may be a PPG signal, and biometric information based on the PPG signal may include at least one of an HR, body pressure, stress information (e.g., a stress index), information about a sleep state, and/or SpO2. In an embodiment, the processor 620 may control to select an R-Curve which corresponds to a wearing state of the electronic device 600 from among a plurality of R-Curves mapped to a plurality of wearing states, and to measure SpO2 using the selected R-Curve.

According to an embodiment, the memory 630 may store data (e.g., biometric information) of the electronic device 600. In an embodiment, the memory 630 may store at least one R-Curve used for SpO2 measurement. In an embodiment, the memory 630 may store a plurality of R-Curves mapped to a plurality of wearing states of the user. In an embodiment, an R-Curve may be a group including pairs of an R value and SpO2. In an embodiment, a correlation between the R value and the SpO2 may be indicated by taking the R-Curve as an example, but the correlation between the R value and the SpO2 may be indicated as/via a table including the pairs of the R value and the SpO2. In an embodiment, the plurality of R-Curves may be updated if necessary. In an embodiment, a unique ID may be allocated to each of the plurality of R-Curves. For example, the unique ID may be an R-Curve index or a table index.

According to an embodiment, the display 640 may receive at least one biometric information from the processor 620 and visually display the received at least one biometric information. For example, the display 640 may display a user interface which is based on a biometric signal measured when an application (e.g., an electrocardiogram application and a health management application) for biometric signal measurement is executed. Also, the display 640 may output a guide screen or information about an abnormal state when the biometric signal is measured under the control of the processor 620.

According to an embodiment, the electronic device 600 may communicate with an external electronic device (e.g., an electronic device 102, an electronic device 104, or a server 108 in FIG. 1A) via the communication circuit 650.

Figure 7:
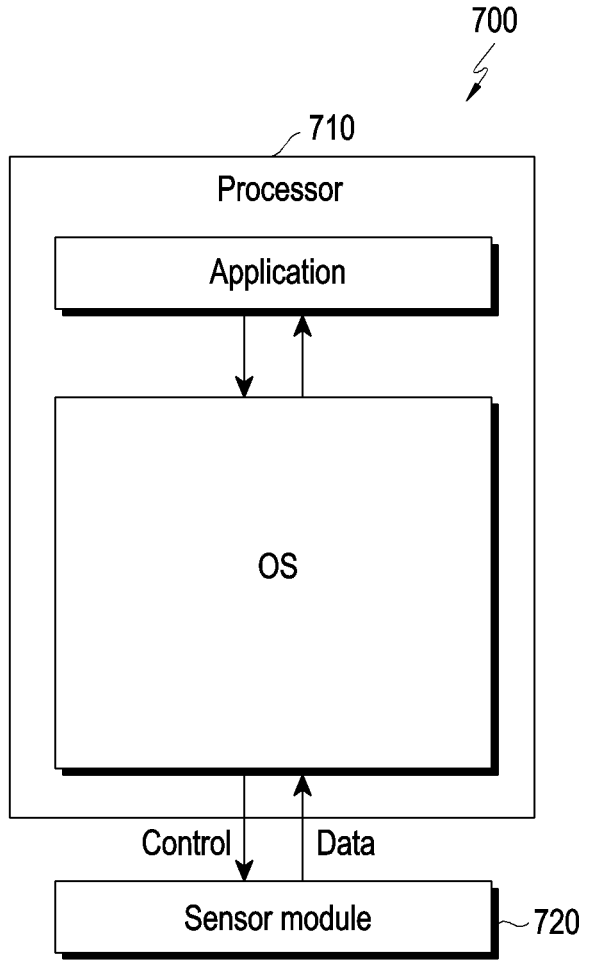
FIG. 7 is a block diagram illustrating a software layer structure of an electronic device according to an example embodiment.

FIG. 7 is a block diagram illustrating a software layer structure of an electronic device according to an embodiment.

Referring to FIG. 7, an electronic device 700 (e.g., an electronic device 101 in FIG. 1A, an electronic device 101b in FIG. 1B to FIG. 1D, or an electronic device 600 in FIG. 6) may be a device for providing biometric information, and may be a wearable electronic device. In an embodiment, the biometric information may be SpO2.

The electronic device 700 may include a processor (e.g., an application processor (AP) and/or a sensor hub processor) 710 (e.g., a processor 120 in FIG. 1A or a processor 620 in FIG. 6) and a sensor module 720 (e.g., a sensor module 176 in FIG. 1A, a sensor module 165 in FIG. 1B, or a sensor module 610 in FIG. 6).

The processor 710 may execute an application (e.g., an application 146 in FIG. 1A) and an operating system (OS) (e.g., an operating system 142 in FIG. 1A), receive data (e.g., a biometric signal) from the sensor module 720, and transmit a control signal for controlling the sensor module 720. The processor 710 may include a separate auxiliary processor (e.g., an auxiliary processor 123 in FIG. 1A, a micro controller (e.g., a micro controller unit (MCU), and a sensor hub processor) for a low-power operation. The micro controller may control the sensor module 720, and process data received from the sensor module 720 by a designated method (e.g., noise filtering) to transfer the processed data to a main processor (e.g., an AP). Alternatively, the main processor (e.g., a main processor 121 in FIG. 1A and the AP) may also control the sensor module 720 and process the data received from the sensor module 720.

The sensor module 720 may include at least one sensor. In an embodiment, the sensor module 720 may obtain at least one biometric signal from the at least one sensor (e.g., a PPG sensor). In an embodiment, the biometric signal may be a PPG signal. In an embodiment, the sensor module 720 may obtain a signal related to movement of the electronic device 700 via the at least one sensor (e.g., an acceleration sensor, an angular velocity sensor, or a motion sensor). In an embodiment, the sensor module 720 may obtain a signal related to a wearing state of the electronic device 700 via the at least one sensor (e.g., a pressure sensor, an ECG sensor, and a PPG sensor).

An embodiment may provide an electronic device for providing biometric information and an operating method thereof.

An embodiment may provide an electronic device capable of increasing SpO2 accuracy by removing a section in which inaccurate SpO2 measurement may occur if SpO2 is measured based on a Continuous scheme, and an operating method thereof.

According to an embodiment, an electronic device (e.g., an electronic device 101 in FIG. 1A, an electronic device 101b in FIG. 1B to FIG. 1D, an electronic device 600 in FIG. 6, or an electronic device 700) may comprise at least one sensor (e.g., a sensor module 176 in FIG. 1A, a sensor module 165 in FIG. 1B, a sensor module 610 in FIG. 6, or a sensor module 720 in FIG. 7) and at least one processor (e.g., a processor 120 in FIG. 1A, a processor 620 in FIG. 6, or a processor 710 in FIG. 7) operatively connected, directly or indirectly, with the at least one sensor (e.g., the sensor module 176 in FIG. 1A, the sensor module 165 in FIG. 1B, the sensor module 610 in FIG. 6, or the sensor module 720 in FIG. 7).

According to an embodiment, the at least one processor (e.g., the processor 120 in FIG. 1A, the processor 620 in FIG. 6, or the processor 710 in FIG. 7) may be configured to, if change amount of movement of the electronic device (e.g., the electronic device 101 in FIG. 1A, the electronic device 101b in FIG. 1B to FIG. 1D, the electronic device 600 in FIG. 6, or the electronic device 700) obtained via the at least one sensor (e.g., the sensor module 176 in FIG. 1A, the sensor module 165 in FIG. 1B, the sensor module 610 in FIG. 6, or the sensor module 720 in FIG. 7) is within a threshold range, identify a wearing state of the electronic device (e.g., the electronic device 101 in FIG. 1A, the electronic device 101b in FIG. 1B to FIG. 1D, the electronic device 600 in FIG. 6, or the electronic device 700) via the at least one sensor (e.g., the sensor module 176 in FIG. 1A, the sensor module 165 in FIG. 1B, the sensor module 610 in FIG. 6, or the sensor module 720 in FIG. 7).

According to an embodiment, the at least one processor (e.g., the processor 120 in FIG. 1A, the processor 620 in FIG. 6, or the processor 710 in FIG. 7) may be further configured to select a group which corresponds to the wearing state from among a plurality of groups including a first group including saturations of percutaneous oxygen (SpO2s) which correspond to reference values based on photoplethysmogram (PPG) signals and a second group including other SpO2s which correspond to the reference values.

According to an embodiment, the at least one processor (e.g., the processor 120 in FIG. 1A, the processor 620 in FIG. 6, or the processor 710 in FIG. 7) may be further configured to obtain a first PPG signal via the at least one sensor (e.g., the sensor module 176 in FIG. 1A, the sensor module 165 in FIG. 1B, the sensor module 610 in FIG. 6, or the sensor module 720 in FIG. 7), and obtain a first SpO2 using the selected group and a first reference value which is based on the first PPG signal.

According to an embodiment, the at least one processor (e.g., the processor 120 in FIG. 1A, the processor 620 in FIG. 6, or the processor 710 in FIG. 7) may be configured to identify a degree of similarity between wearing state information which corresponds to the identified wearing state and each of pieces of wearing state information mapped to the plurality of groups, and select a group mapped to wearing state information having a large and/or maximum value from among the identified degrees of similarity as a group which corresponds to the identified wearing state.

According to an embodiment, wearing state information includes at least one of pressure applied to the electronic device (e.g., the electronic device 101 in FIG. 1A, the electronic device 101b in FIG. 1B to FIG. 1D, the electronic device 600 in FIG. 6, or the electronic device 700) by a user's body, a size of an area in which the electronic device (e.g., the electronic device 101 in FIG. 1A, the electronic device 101b in FIG. 1B to FIG. 1D, the electronic device 600 in FIG. 6, or the electronic device 700) is in contact with the user's body, or a direction in which the electronic device (e.g., the electronic device 101 in FIG. 1A, the electronic device 101b in FIG. 1B to FIG. 1D, the electronic device 600 in FIG. 6, or the electronic device 700) is in contact with the user's body as information elements.

According to an embodiment, the at least one processor (e.g., the processor 120 in FIG. 1A, the processor 620 in FIG. 6, or the processor 710 in FIG. 7) may be configured to identify degrees of similarity between information elements included in the wearing state information which corresponds to the identified wearing state and information elements included in each of the pieces of wearing state information mapped to the plurality of groups.

According to an embodiment, the at least one processor (e.g., the processor 120 in FIG. 1A, the processor 620 in FIG. 6, or the processor 710 in FIG. 7) may be configured to, for each of the plurality of groups, apply a weight value set for each information element to each of the identified degrees of similarity for the information elements.

According to an embodiment, the at least one processor (e.g., the processor 120 in FIG. 1A, the processor 620 in FIG. 6, or the processor 710 in FIG. 7) may be configured to select, from among the plurality of groups, a group in which sum of degrees of similarity to which the weight value is applied is a large and/or maximum value as the group which corresponds to the identified wearing state.

According to an embodiment, the large and/or maximum value among sums of degrees of similarity to which the weight value is applied may be greater than or equal to a set minimum and/or small degree of similarity.

According to an embodiment, the movement may be obtained based on at least one of an acceleration signal or an angular velocity signal obtained via the at least one sensor (e.g., the sensor module 176 in FIG. 1A, the sensor module 165 in FIG. 1B, the sensor module 610 in FIG. 6, or the sensor module 720 in FIG. 7).

According to an embodiment, the wearing state may be obtained based on at least one of a PPG signal, an electrocardiography (ECG) signal, and a pressure signal obtained via the at least one sensor (e.g., the sensor module 176 in FIG. 1A, the sensor module 165 in FIG. 1B, the sensor module 610 in FIG. 6, or the sensor module 720 in FIG. 7).

According to an embodiment, the at least one processor (e.g., the processor 120 in FIG. 1A, the processor 620 in FIG. 6, or the processor 710 in FIG. 7) may be configured to, if the wearing state is a wearing state in which a size of an area in which the electronic device (e.g., the electronic device 101 in FIG. 1A, the electronic device 101b in FIG. 1B to FIG. 1D, the electronic device 600 in FIG. 6, or the electronic device 700) is in contact with a user's body is larger than or equal to a threshold area, select the first group and obtain the first SpO2 using the first group and the first reference value.

According to an embodiment, the at least one processor (e.g., the processor 120 in FIG. 1A, the processor 620 in FIG. 6, or the processor 710 in FIG. 7) may be configured to, if the wearing state is a wearing state which is applied when a group (e.g., a single group) used in a second measuring scheme is generated, select the second group and obtain the first SpO2 using the second group and the first reference value, and the second measuring scheme may be different from a first measuring scheme in which the plurality of groups are used.

According to an embodiment, the electronic device (e.g., the electronic device 101 in FIG. 1A, the electronic device 101b in FIG. 1B to FIG. 1D, the electronic device 600 in FIG. 6, or the electronic device 700) may further comprise a communication circuit (e.g., a communication module 190 in FIG. 1A or a communication circuit 650 in FIG. 6).

According to an embodiment, the at least one processor (e.g., the processor 120 in FIG. 1A, the processor 620 in FIG. 6, or the processor 710 in FIG. 7) may be configured to, after obtaining the first SpO2, switch from a first measuring scheme in which the plurality of groups are used to a second measuring scheme in which a group (e.g., a single group) is used.

According to an embodiment, the at least one processor (e.g., the processor 120 in FIG. 1A, the processor 620 in FIG. 6, or the processor 710 in FIG. 7) may be configured to obtain a second PPG signal via the at least one sensor (e.g., the sensor module 176 in FIG. 1A, the sensor module 165 in FIG. 1B, the sensor module 610 in FIG. 6, or the sensor module 720 in FIG. 7) in the second measuring scheme.

According to an embodiment, the at least one processor (e.g., the processor 120 in FIG. 1A, the processor 620 in FIG. 6, or the processor 710 in FIG. 7) may be configured to obtain a second SpO2 using the single group and a second reference value which is based on the second PPG signal. Each "processor" herein comprises processing circuitry.

According to an embodiment, the at least one processor (e.g., the processor 120 in FIG. 1A, the processor 620 in FIG. 6, or the processor 710 in FIG. 7) may be configured to transmit, to an external electronic device (e.g., a server 108 in FIG. 1A or a server 1800 in FIG. 18) via the communication circuit (e.g., the communication module 190 in FIG. 1A or the communication circuit 650 in FIG. 6), at least one of the first SpO2, the first reference value, an identifier of the selected group, and the second SpO2 to update the selected group.

According to an embodiment, the selected group may be updated by changing the first reference value included in the selected group to the second reference value which corresponds to the second SpO2.

According to an embodiment, the at least one processor (e.g., the processor 120 in FIG. 1A, the processor 620 in FIG. 6, or the processor 710 in FIG. 7) may be configured to switch from the first measuring scheme to the second measuring scheme if a condition is satisfied.

According to an embodiment, the condition may include at least one of a condition that change amount of the movement of the electronic device (e.g., the electronic device 101 in FIG. 1A, the electronic device 101*b* in FIG. 1B to FIG. 1D, the electronic device 600 in FIG. 6, or the electronic device 700) obtained via the at least one sensor (e.g., the sensor module 176 in FIG. 1A, the sensor module 165 in FIG. 1B, the sensor module 610 in FIG. 6, or the sensor module 720 in FIG. 7) is within a first threshold range, a condition that set time elapses after a time point at which the measurement of the first SpO2 is completed, or a condition that change amount of SpO2s measured in the first measuring scheme is within a second threshold range.

According to an embodiment, the movement may be obtained based on at least one of an acceleration signal or an angular velocity signal obtained via the at least one sensor (e.g., the sensor module 176 in FIG. 1A, the sensor module 165 in FIG. 1B, the sensor module 610 in FIG. 6, or the sensor module 720 in FIG. 7).

According to an embodiment, the at least one processor (e.g., the processor 120 in FIG. 1A, the processor 620 in FIG. 6, or the processor 710 in FIG. 7) may be configured to identify a degree of similarity between wearing state information which corresponds to the identified wearing state and each of pieces of wearing state information mapped to the plurality of groups.

According to an embodiment, the at least one processor (e.g., the processor 120 in FIG. 1A, the processor 620 in FIG. 6, or the processor 710 in FIG. 7) may be configured to select a group mapped to wearing state information having a large and/or maximum value from among the identified degrees of similarity as a group which corresponds to the identified wearing state.

According to an embodiment, wearing state information includes at least one of pressure applied to the electronic device (e.g., the electronic device 101 in FIG. 1A, the electronic device 101*b* in FIG. 1B to FIG. 1D, the electronic device 600 in FIG. 6, or the electronic device 700) by a user's body, a size of an area in which the electronic device (e.g., the electronic device 101 in FIG. 1A, the electronic device 101*b* in FIG. 1B to FIG. 1D, the electronic device 600 in FIG. 6, or the electronic device 700) is in contact with the user's body, or a direction in which the electronic device (e.g., the electronic device 101 in FIG. 1A, the electronic device 101*b* in FIG. 1B to FIG. 1D, the electronic device 600 in FIG. 6, or the electronic device 700) is in contact with the user's body as information elements.

According to an embodiment, the at least one processor (e.g., the processor 120 in FIG. 1A, the processor 620 in FIG. 6, or the processor 710 in FIG. 7) may be configured to identify degrees of similarity between information elements included in the wearing state information which corresponds to the identified wearing state and information elements included in each of the pieces of wearing state information mapped to the plurality of groups.

According to an embodiment, the at least one processor (e.g., the processor 120 in FIG. 1A, the processor 620 in FIG. 6, or the processor 710 in FIG. 7) may be configured to, for each of the plurality of groups, apply a weight value set for each information element to each of the identified degrees of similarity for the information elements.

According to an embodiment, the at least one processor (e.g., the processor 120 in FIG. 1A, the processor 620 in FIG. 6, or the processor 710 in FIG. 7) may be configured to select, from among the plurality of groups, a group in which sum of degrees of similarity to which the weight value is applied is a large and/or maximum value as the group which corresponds to the identified wearing state.

According to an embodiment, the large and/or maximum value among sums of degrees of similarity to which the weight value is applied may be greater than or equal to a set minimum and/or small degree of similarity.

According to an embodiment, the at least one processor (e.g., the processor 120 in FIG. 1A, the processor 620 in FIG. 6, or the processor 710 in FIG. 7) may be configured to, upon identifying that change amount of the movement of the electronic device (e.g., the electronic device 101 in FIG. 1A, the electronic device 101*b* in FIG. 1B to FIG. 1D, the electronic device 600 in FIG. 6, or the electronic device 700) obtained via the at least one sensor (e.g., the sensor module 176 in FIG. 1A, the sensor module 165 in FIG. 1B, the sensor module 610 in FIG. 6, or the sensor module 720 in FIG. 7) is within a first threshold range, identify the wearing state for the electronic device (e.g., the electronic device 101 in FIG. 1A, the electronic device 101*b* in FIG. 1B to FIG. 1D, the electronic device 600 in FIG. 6, or the electronic device 700) in the first measuring scheme.

According to an embodiment, the movement may be obtained based on at least one of an acceleration signal or an angular velocity signal obtained via the at least one sensor (e.g., the sensor module 176 in FIG. 1A, the sensor module 165 in FIG. 1B, the sensor module 610 in FIG. 6, or the sensor module 720 in FIG. 7).

According to an embodiment, the wearing state may be obtained based on at least one of a PPG signal, an electrocardiography (ECG) signal, and a pressure signal obtained via the at least one sensor (e.g., the sensor module 176 in FIG. 1A, the sensor module 165 in FIG. 1B, the sensor module 610 in FIG. 6, or the sensor module 720 in FIG. 7).

According to an embodiment, the at least one processor (e.g., the processor 120 in FIG. 1A, the processor 620 in FIG. 6, or the processor 710 in FIG. 7) may be further configured to receive, from the external electronic device (e.g., the server 108 in FIG. 1A or the server 1800 in FIG. 18) via the communication circuit (e.g., the communication module 190 in FIG. 1A or the communication circuit 650 in FIG. 6), an identifier of a updated group and the updated group.

According to an embodiment, if a difference between the first SpO2 and the second SpO2 is less than or equal to a threshold value, the updated group may be updated by changing the first reference valued included in the selected group to the second reference value which corresponds to the second SpO2.

According to an embodiment, the at least one processor (e.g., the processor 120 in FIG. 1A, the processor 620 in FIG. 6, or the processor 710 in FIG. 7) may be configured to, if the wearing state is a wearing state in which a size of an area in which the electronic device (e.g., the electronic device 101 in FIG. 1A, the electronic device 101b in FIG. 1B to FIG. 1D, the electronic device 600 in FIG. 6, or the electronic device 700) is in contact with a user's body is larger than or equal to a threshold area, select the first group and obtain the first SpO2 using the first group and the first reference value.

According to an embodiment, the at least one processor (e.g., the processor 120 in FIG. 1A, the processor 620 in FIG. 6, or the processor 710 in FIG. 7) may be configured to, if the wearing state is a wearing state which is applied when a group (e.g., a single group) used in a second measuring scheme is generated, select the second group and obtain the first SpO2 using the second group and the first reference value, and the second measuring scheme may be different from a first measuring scheme in which the plurality of groups are used.

Figure 18:
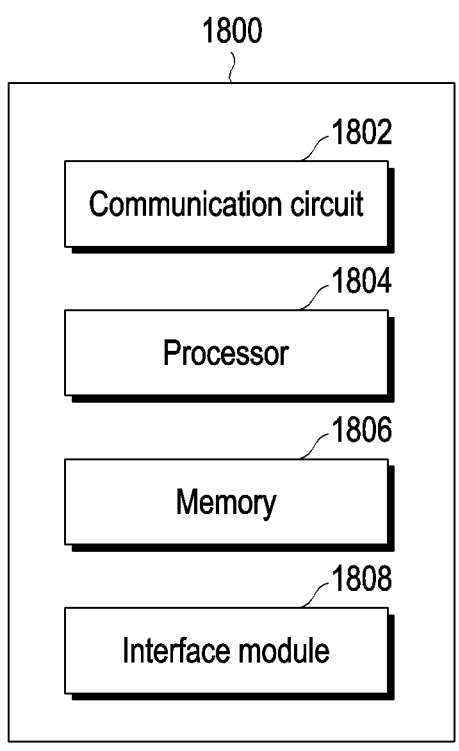
FIG. 18 is a block diagram illustrating a server according to an example embodiment.

According to an embodiment, an external electronic device (e.g., a server 108 in FIG. 1A or a server 1800 in FIG. 18) may comprise a communication circuit (e.g., a communication module including communication circuitry 1802 in FIG. 18) and at least one processor (e.g., a processor 1804 in FIG. 18) operatively connected, directly or indirectly, with the communication circuit (e.g., the communication module including communication circuitry 1802 in FIG. 18).

According to an embodiment, the at least one processor (e.g., the processor 1804 in FIG. 18) may be configured to receive, from an electronic device (e.g., an electronic device 101 in FIG. 1A, an electronic device 101b in FIG. 1B to FIG. 1D, an electronic device 600 in FIG. 6, or an electronic device 700) via the communication circuit (e.g., the communication module including communication circuitry 1802 in FIG. 18), a first SpO2 obtained in a first measuring scheme in which a plurality of groups including a first group including saturations of percutaneous oxygen (SpO2s) which correspond to reference values based on photoplethysmogram (PPG) signals and a second group including other SpO2s which correspond to the reference values are used, a first reference value which corresponds to the first SpO2, an identifier of a group used for obtaining the first SpO2 among the plurality of groups, and a second SpO2 measured in a second measuring scheme in which a group (e.g., single group) is used.

According to an embodiment, the at least one processor (e.g., the processor 1804 in FIG. 18) may be further configured to, if a difference between the first SpO2 and the second SpO2 is less than or equal to a threshold value, update a group mapped to the identifier by changing the first reference value included in the group mapped to the identifier to a second reference value which corresponds to the second SpO2.

According to an embodiment, the at least one processor (e.g., the processor 1804 in FIG. 18) may be further configured to transmit, to the electronic device (e.g., the electronic device 101 in FIG. 1A, the electronic device 101b in FIG. 1B to FIG. 1D, the electronic device 600 in FIG. 6, or the electronic device 700) via the communication circuit (e.g., the communication module including communication circuitry 1802 in FIG. 18), the identifier and the updated group.

According to an embodiment, the group used for obtaining the first SpO2 may be a group mapped to wearing state information which corresponds to the wearing state of the electronic device (e.g., the electronic device 101 in FIG. 1A, the electronic device 101b in FIG. 1B to FIG. 1D, the electronic device 600 in FIG. 6, or the electronic device 700 in FIG. 7) identified in the first measuring scheme among the plurality of groups.

According to an embodiment, the wearing state may be obtained based on at least one of a PPG signal, an electrocardiography (ECG) signal, or a press signal obtained via at least one sensor (e.g., a sensor module 176 in FIG. 1A, a sensor module 165 in FIG. 1B, a sensor module 610 in FIG. 6, or a sensor module 720 in FIG. 7) included in the electronic device (e.g., the electronic device 101 in FIG. 1A, the electronic device 101b in FIG. 1B to FIG. 1D, the electronic device 600 in FIG. 6, or the electronic device 700 in FIG. 7).

According to an embodiment, a measuring scheme of the electronic device (e.g., the electronic device 101 in FIG. 1A, the electronic device 101b in FIG. 1B to FIG. 1D, the electronic device 600 in FIG. 6, or the electronic device 700 in FIG. 7) may be switched from the first measuring scheme to the second measuring scheme if a condition is satisfied.

According to an embodiment, the condition may include at least one of a condition that change amount of the movement of the electronic device (e.g., the electronic device 101 in FIG. 1A, the electronic device 101b in FIG. 1B to FIG. 1D, the electronic device 600 in FIG. 6, or the electronic device 700 in FIG. 7) is within a first threshold range, a condition that set time elapses after a time point at which the electronic device (e.g., the electronic device 101 in FIG. 1A, the electronic device 101b in FIG. 1B to FIG. 1D, the electronic device 600 in FIG. 6, or the electronic device 700 in FIG. 7) completes the measurement of the first SpO2, or a condition that change amount of SpO2s measured in the first measuring scheme is within a second threshold range.

According to an embodiment, the movement may be obtained based on at least one of an acceleration signal or an angular velocity signal obtained via at least one sensor (e.g., a sensor module 176 in FIG. 1A, a sensor module 165 in FIG. 1B, a sensor module 610 in FIG. 6, or a sensor module 720 in FIG. 7) included in the electronic device (e.g., the electronic device 101 in FIG. 1A, the electronic device 101b in FIG. 1B to FIG. 1D, the electronic device 600 in FIG. 6, or the electronic device 700).

According to an embodiment, the at least one processor (e.g., the processor 1804 in FIG. 18) may be further configured to, if the difference between the first SpO2 and the second SpO2 is greater than the threshold value, transmit, to the electronic device (e.g., the electronic device 101 in FIG. 1A, the electronic device 101b in FIG. 1B to FIG. 1D, the electronic device 600 in FIG. 6, or the electronic device 700) via the communication circuit (e.g., the communication module including communication circuitry 1802 in FIG. 18), a message indicating that a group update is not performed.

Figure 8:
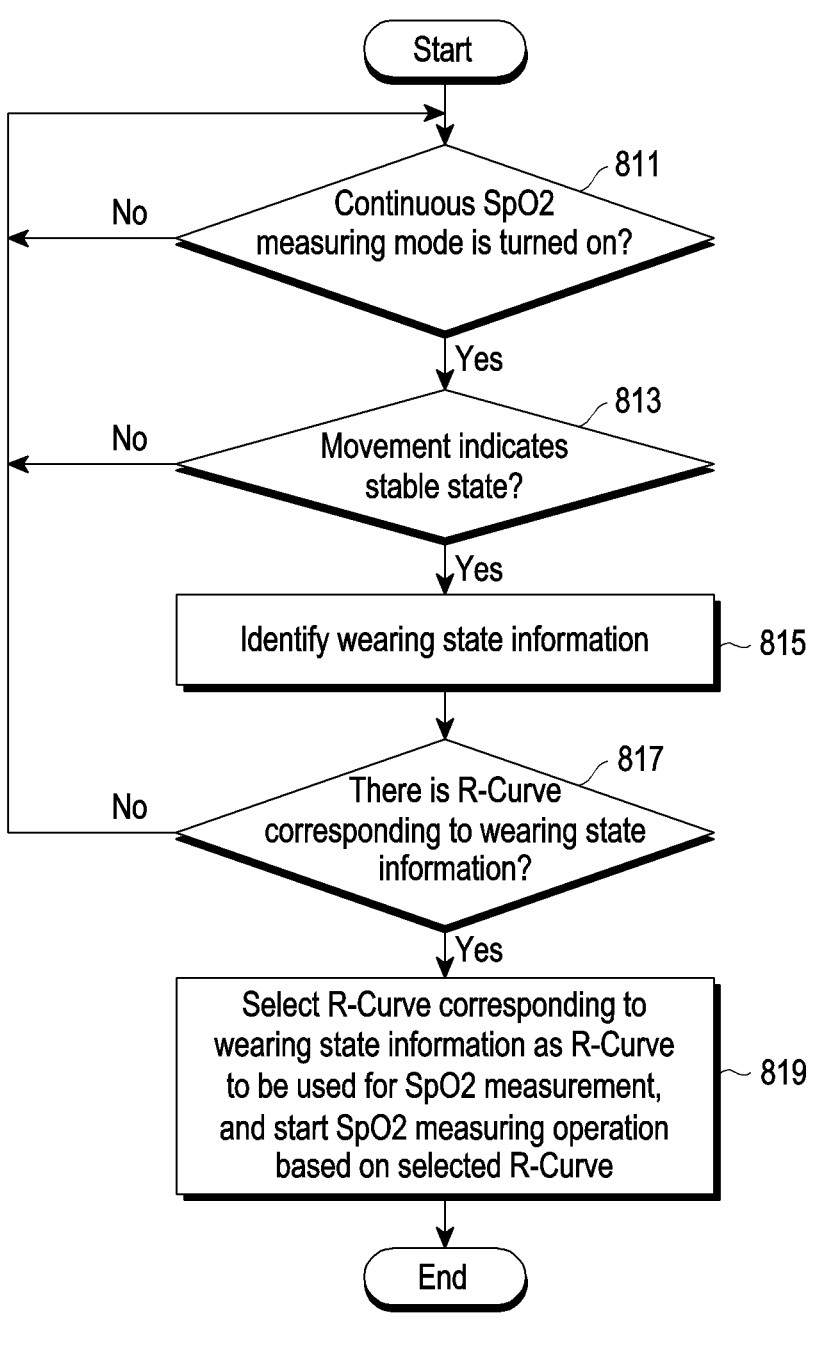
FIG. 8 is a flowchart schematically illustrating an example of an operating process of an electronic device according to an example embodiment.

FIG. 8 is a flowchart schematically illustrating an example of an operating process of an electronic device according to an embodiment.

Referring to FIG. 8, in operation 811, a processor (e.g., a processor 120 in FIG. 1A, a processor 620 in FIG. 6, or a processor 710 in FIG. 7) of an electronic device (e.g., an electronic device 101 in FIG. 1A, an electronic device 101b in FIG. 1B to FIG. 1D, an electronic device 600 in FIG. 6, or an electronic device 700 in FIG. 7) may identify whether a Continuous SpO2 measuring mode is turned on (e.g., whether the Continuous SpO2 measuring mode exists in an on-state). In an embodiment, the Continuous SpO2 measuring mode may be turned on based on a user input. In an embodiment, the Continuous SpO2 measuring mode may be turned on at designated time (e.g., time set by a user to turn on the Continuous SpO2 measuring mode). In an embodiment, the Continuous SpO2 measuring mode may be turned on if a value of a flag indicating the Continuous SpO2 measuring mode included in a set program is set to a set value, e.g., "1". In an embodiment, the Continuous SpO2 measuring mode may be turned on when being called by at least one instruction. According to an embodiment, the Continuous SpO2 measuring mode may be turned on in various forms, and it is not limited to a case that the Continuous SpO2 measuring mode is turned on by the flag or the instruction. An On-demand SpO2 measuring mode may be an SpO2 measuring mode which uses an R-Curve (e.g., a single R-Curve). In an embodiment, the On-demand SpO2 measuring mode may be an SpO2 measuring mode which is based on an On-demand scheme. An R-Curve used in the On-demand SpO2 measuring mode may be an R-Curve generated through a Calibration process in a reference SpO2 measuring device. The Continuous SpO2 measuring mode may be an SpO2 measuring mode which uses a plurality of R-Curves. In an embodiment, the Continuous SpO2 measuring mode may be an SpO2 measuring mode which is based on a Continuous scheme. The plurality of R-Curves used in the Continuous SpO2 measuring mode may be R-Curves generated through the Calibration process in the reference SpO2 measuring device. In an embodiment, wearing state information may be mapped to each of the plurality of R-Curves, and wearing state information mapped to the plurality of R-Curves may be different from each other. In an embodiment, the wearing state information is information indicating the wearing state, and the wearing state may be a state indicating in what form the wearable electronic device is worn on a part of the user's body. According to an embodiment, the wearing state may be a state not indicating that the electronic device is worn on the part of the user's body itself, but indicating in what form the electronic device is worn on the part of the user's body.

For example, the wearing state may indicate in what form the wearable electronic device is worn on the part (e.g., a wrist) of the user's body such as a state in which the electronic device is pressed relatively heavily by the part of the user's body and a state in which the electronic device is relatively greatly lifted from the part of the user's body. For example, the state in which the electronic device is pressed relatively heavily by the part of the user's body may indicate a state in which all of an area in which the electronic device is in contact with the part of the user's body are pressed relatively heavily or a state in which a part of the area in which the electronic device is in contact with the part of the user's body is pressed relatively heavily.

According to an embodiment, the wearing state information mapped to the plurality of R-Curves may correspond to any wearing state except for a wearing state in which SpO2 measurement is impossible (e.g., a wearing state in which valid SpO2 may not be obtained) in the Continuous SpO2 measuring mode. For example, the wearing state in which the SpO2 measurement is impossible may indicate a wearing state in which it is impossible to secure a minimum SNR used for obtaining an R value (e.g., a case that relatively much external light is received via a light receiving unit in a PPG sensor as the electronic device is relatively greatly lifted from the part of the user's body).

According to an embodiment, a wearing state may be identified based on at least one wearing state signal obtained via a sensor module (e.g., a sensor module 176 in FIG. 1A, a sensor module 165 in FIG. 1B, a sensor module 610 in FIG. 6, or a sensor module 720 in FIG. 7) which is included in the electronic device and includes at least one sensor.

The wearing state information may include at least one information element, and each of the at least one information element may indicate a wearing state which corresponds to a wearing state signal. For example, if the wearing state information includes three information elements, the three information elements may include pressure applied between the electronic device and the part of the user's body (e.g., pressure applied to the electronic device by the user's body), a size of an area in which the electronic device is in contact with the part of the user's body (e.g., a size of an area in which the electronic device is in contact with the user's body), and a direction in which the electronic device is in contact with the part of the user's body.

In an embodiment, the pressure applied between the electronic device and the part of the user's body may be obtained via a pressure sensor and/or a PPG sensor included in the sensor module, and in this case, the wearing state signal may be a pressure signal. In an embodiment, a size of the area in which the electronic device is in contact with the part of the user's body may be obtained via the PPG sensor included in the sensor module, and in this case, the wearing state signal may be a PPG signal. In an embodiment, a direction in which the electronic device is in contact with the part of the user's body may be obtained via an ECG sensor, and in this case, the wearing state signal may be an ECG signal.

As a result of identifying in operation 811, if the Continuous SpO2 measuring mode is not turned on, the processor may repeat operation 811 until it is identified that the Continuous SpO2 measuring mode is turned on. As the result of identifying in operation 811, if the Continuous SpO2 measuring mode is turned on, the processor may identify whether movement of the electronic device indicates a stable state based on at least a part of a movement signal obtained via the sensor module in operation 813. In an embodiment, the movement signal may include an acceleration signal obtained via an acceleration sensor included in the electronic device and/or an angular velocity signal obtained via a gyro sensor included in the electronic device.

In an embodiment, the stable state may indicate a state in which movement satisfies a set condition. In an embodiment, the set condition may include a condition in which amount of a change in the movement is within a threshold range. In an embodiment, the movement may be identified based on at least one of the acceleration signal or the angular velocity signal. In an embodiment, the set condition may include a condition which is based on at least one of a threshold value or threshold change amount of acceleration. For example, if the set condition is a condition which is based on the threshold value of acceleration, the set condition may be a condition in which an absolute DC value of the acceleration signal is less than the threshold value. As another example, if the set condition is a condition which is based on the threshold change amount of acceleration, the set condition may be a condition in which change amount of a DC value of the acceleration signal is less than the threshold change amount. In an embodiment, the set condition may include a condition which is based on at least one of a threshold value or threshold change amount of an angular velocity. For example, if the set condition is a condition which is based on the threshold value of angular velocity, the set condition may be a condition in which an absolute DC value of the angular velocity signal is less than the threshold value. As another example, if the set condition is a condition which is based on the threshold change amount of angular velocity, the set condition may be a condition in which change amount of a DC value of the angular velocity signal is less than the threshold change amount.

In an embodiment, the set condition may further include a condition which is based on a threshold value of acceleration and a threshold value of duration. If the set condition further includes the threshold value of acceleration the threshold value of duration, an embodiment of determining the stable state may be possible as shown in Table 2 below.

TABLE 2

| | Absolute DC Value of Acceleration Signal $(\sqrt{ACC\_X^2 + ACC\_Y^2 + ACC\_Z^2})$ | Duration | User State |
|---|---|---|---|
| Case 1 | ≥ACC Threshold Value | ≥Duration Threshold Value | Unstable State |
| Case 2 | ≥ACC Threshold Value | <Duration Threshold Value | Stable State |

In Table 2, ACC_X may denote an X component of the acceleration signal, ACC_Y may denote a Y component of the acceleration signal, and ACC_Z may denote a Z component of the acceleration signal.

In Table 2, Case 1 may represent a case in which a duration during which $\sqrt{ACC\_X^2 + ACC\_Y^2 + ACC\_Z^2}$ that is the absolute DC value of the acceleration signal is greater than or equal to the threshold value of acceleration (e.g., an ACC threshold value) is longer than or equal to the threshold value of duration, so Case 1 may indicate an unstable state.

In Table 2, Case 2 may represent a case in which a duration during which $\sqrt{ACC\_X^2 + ACC\_Y^2 + ACC\_Z^2}$ that is the absolute DC value of the acceleration signal is greater than or equal to the threshold value of acceleration is shorter than the threshold value of duration, so Case 2 may indicate the stable state.

In an embodiment, the set condition may further include a condition which is based on the threshold value of acceleration. If the set condition includes the threshold value of acceleration, if $\sqrt{ACC\_X^2 + ACC\_Y^2 + ACC\_Z^2}$ which is the absolute DC value of the acceleration signal is less than the threshold value of acceleration (e.g., the ACC threshold value), a user state may indicate the stable state.

An embodiment in which it is possible to identify whether the movement of the electronic device indicates the stable state is not limited to an embodiment shown in Table 2, and it may be implemented to identify whether the movement of the electronic device indicates the stable state in various forms by the set condition including at least a part of the acceleration, the angular velocity, and/or the duration. For example, the processor may identify the movement of the user (e.g., toss and turn during sleep) of the electronic device based on the acceleration signal obtained via the acceleration sensor. For another example, the processor may identify the movement of the user (e.g., the toss and turn during the sleep) of the electronic device based on the angular velocity signal obtained via the gyro sensor.

If the movement of the electronic device indicates the stable state in operation 813 (operation 813—Yes), the processor may identify wearing state information of the electronic device based on at least a part of a wearing state signal obtained via the sensor module in operation 815. The wearing state information based on the wearing state signal and information elements included in the wearing state may be the same as described in operation 811. In an embodiment, pressure applied between the electronic device and the part of the user's body may be obtained via the PPG sensor as well as the pressure sensor, and in this case, the wearing state signal may be a PPG signal. As a result of identifying in operation 813, if the movement of the electronic device does not indicate the stable state (operation 813—No), the processor may repeat operation 811.

In FIG. 8, a scheme in which the electronic device measures the SpO2 based on at least the part of the movement signal and/or at least the part of the wearing state signal obtained via the sensor module included in the electronic device has been described. However, if the electronic device is capable of receiving at least a part of a movement signal and/or at least a part of a wearing state signal obtained via a sensor module which is attached to the part of the user's body while existing outside the electronic device as well as the sensor module included in the electronic device, the electronic device may measure SpO2 based on at least the part of the movement signal and/or at least the part of the wearing state signal in a scheme similar to or the same as that described in FIG. 8.

In an embodiment, an example of disposition and a structure of a PPG sensor will be described with reference to FIGS. 9 and 10 as follows.

Figure 9:
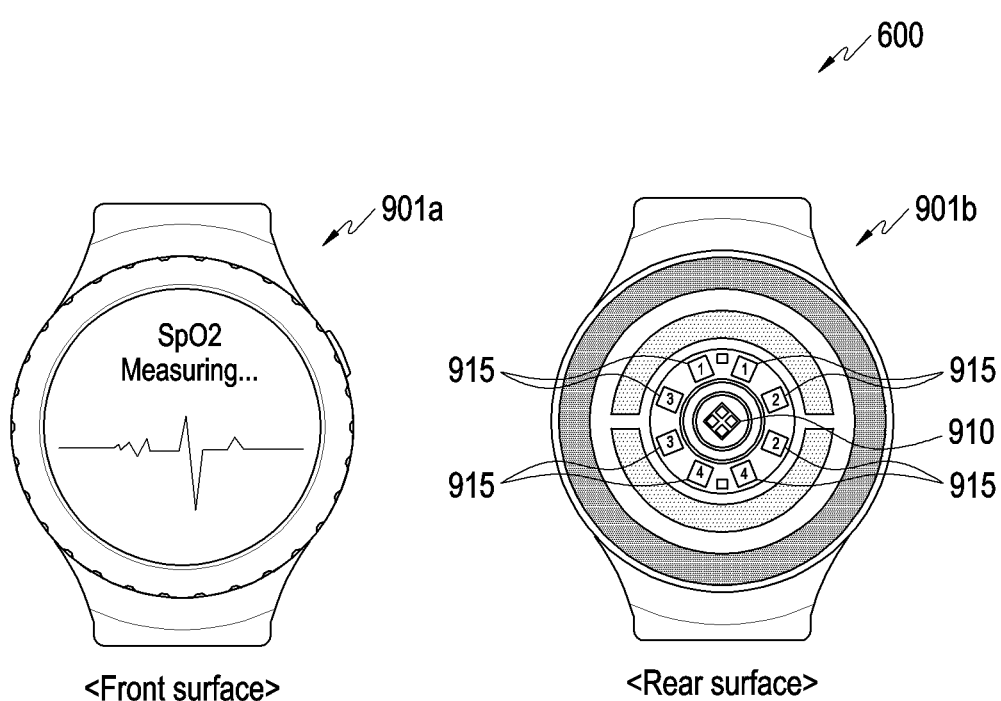
FIG. 9 is a diagram schematically illustrating an example of disposition of a PPG sensor according to an example embodiment.

FIG. 9 is a diagram schematically illustrating an example of disposition of a PPG sensor according to an embodiment.

Referring to FIG. 9, a surface in which a display of an electronic device 600 (e.g., an electronic device 101 in FIG. 1A, an electronic device 101b in FIGS. 1B to 1D, or an electronic device 700 in FIG. 7) is visually exposed may be a front surface 901a, and an opposite surface thereof may be indicated as a rear surface 901b. A PPG sensor including a light emitting unit 910 and a light receiving unit 915 for optical biometric signal measurement may be disposed on the rear surface 901b of the electronic device 600 according to an embodiment, and the light receiving unit 915 may be disposed on substantially the same surface as the light emitting unit 910. In an embodiment, a message indicating that SpO2 is being measured (e.g., "SpO2 Measuring . . . ") may be displayed on the front surface 901a of the electronic device 600 via the display. In FIG. 9, a case in which the message indicating that the SpO2 is being measured is displayed has been illustrated as an example, however, if measurement of the SpO2 is completed later, a message indicating the measured SpO2 may be also displayed.

As shown in FIG. 9, the light emitting unit 910 may be located in the middle of the rear surface 901b, and may be composed of or include a single element, or may include a plurality of elements emitting light of a wavelength of the same band or a plurality of elements emitting light of wavelengths of different bands. A structure in which the light emitting unit 910 includes at least one light emitting element (e.g., an LED) and a structure in which the light receiving unit 915 includes at least one light receiving element (e.g., a PD) may be implemented similarly to a structure of a light emitting unit (e.g., a light emitting unit 1110) and a structure of a light receiving unit (e.g., a light receiving unit 1115) to be described in FIG. 11, and a detailed description thereof will be described in detail in FIG. 11. FIG. 9 has exemplified a case in which the light emitting unit 910 is located in the middle of the rear surface 901b of the electronic device 600, however, the light emitting unit 910 may be disposed outside the light receiving unit 915 in consideration of location relationship between the light emitting unit 910 and the light receiving unit 915.

In FIG. 9, the rear surface 901b on which the PPG sensor is disposed may be also formed as a flat surface or may be also formed as a convex dome shape so as to be in close contact with a part of a user's body (e.g., the user's wrist). A case in which eight light receiving units 915 surrounding the light emitting unit 910 are included on the rear surface 901b has been illustrated in FIG. 9. In addition, although a case in which the rear surface 901b is flat or convex has been described as an example in FIG. 9, a shape thereof may not be limited thereto.

Figure 10:
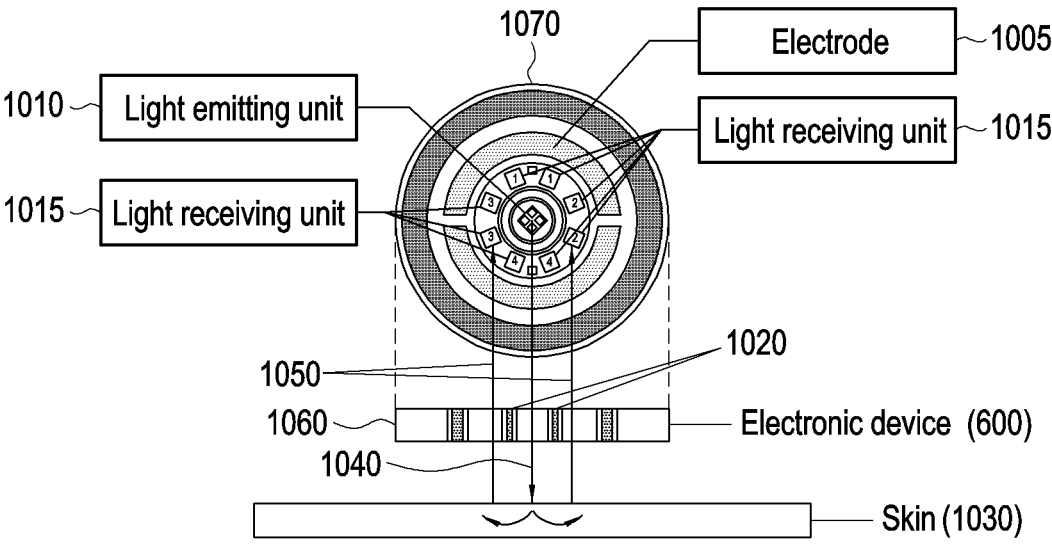
FIG. 10 is a diagram schematically illustrating an example of a structure of a PPG sensor according to an example embodiment.

FIG. 10 is a diagram schematically illustrating an example of a structure of a PPG sensor according to an embodiment.

Referring to FIG. 10, a plurality of sensors are disposed on a rear surface of an electronic device 600 (e.g., an electronic device 101 in FIG. 1A, an electronic device 101b in FIGS. 1B to 1D, or an electronic device 700 in FIG. 7), and a PPG signal (or data) may be measured using a PPG sensor which is an optical sensor and which is one of the plurality of sensors.

An example of a rear surface 1070 of the electronic device 600 and a vertical cross section 1060 of the PPG sensor in the electronic device 600 is illustrated in FIG. 10. As shown in FIG. 10, the PPG sensor may have a structure in which it is divided by a barrier 1020 according to a light receiving unit 1015 and a light emitting unit 1010 of the PPG sensor in the electronic device 600, and such barrier structure may be used as a path for measuring the PPG signal. A structure in which the light emitting unit 1010 includes at least one light emitting element (e.g., an LED) and a structure in which the light receiving unit 1015 includes at least one light receiving element (e.g., PD) may be implemented similarly to a structure of a light emitting unit (e.g., a light emitting unit 1110) and a structure of a light receiving unit (e.g., a light receiving unit 1115) to be described in FIG. 11, and a detailed description thereof will be described in detail in FIG. 11.

According to an embodiment, at least one sensor other than the PPG sensor may be further disposed on the rear surface 1070 of the electronic device 600. According to an embodiment, at least one electrode 1005 may be disposed on the rear surface 1070 of the electronic device 600. At least one electrode 1005 may not be disposed if necessary.

According to an embodiment, a light emitting unit (e.g., at least one LED) and a light receiving unit (e.g., at least one PD) are disposed inside (e.g., on a PCB) the electronic device 600, and at least a part of the rear surface 1070 of the electronic device 600 may be formed of a substantially transparent material. For example, a location at least partially corresponding the light emitting unit 1010 on the rear surface 1070 and at least one location at least partially corresponding to the light receiving unit 1015 on the rear surface 1070 may be formed of a transparent material (e.g., a glass), thereby a part of the light emitting unit 1010 and the light receiving unit 1015 may be visually exposed, and a light emitting path and a light receiving path may be formed. According to an embodiment, the rear surface 1070 may be formed of a substantially opaque material (e.g., a metal and a plastic), and may include at least one opening (not shown) at a location which corresponds to the light emitting unit 1010, the light receiving unit 1015, and/or the at least one electrode 1005. For example, a window glass (not shown) for visually exposing a part of the light emitting unit 1010 and the light receiving unit 1015 and the at least one electrode 1005 may be fitted into the at least one opening. According to an embodiment, the rear surface 1070 of the electronic device 600 may be entirely formed of a transparent material, so that at least a part thereof may be processed to be opaque. For example, substantially opaque ink may be painted on the remaining parts except for a location which corresponds to the light emitting unit 1010 and a location which corresponds to the light receiving unit 1015, thereby an internal component (e.g., a circuit board) may be hidden.

According to an embodiment, at least one opaque optical shield structure (or a barrier) 1020 surrounding the side portion extending from the light emitting unit 1010 and the light receiving unit 1015 to a surface which is exposed to the outside of the rear surface 1070 of the electronic device 600 may be formed. Such an opaque optical shield structure may be referred to as a barrier, and such at least one barrier may prevent or reduce light emitted from the light emitting unit 1010 from entering the light receiving unit 1015 after being diffracted or reflected by the internal structure of the electronic device 600 or prevent or reduce light-leakage phenomenon on a path on which light reflected from a user's skin 1030 enters the light receiving unit 1015.

According to an embodiment, the electronic device 600 may sequentially perform reception of an ECG signal via the at least one electrode 1005 and/or reception of a PPG signal via the light emitting unit 1010 and the light receiving unit 1015. According to an embodiment, when measurement of a biometric signal is started, the light emitting unit 1010 (including at least one light source) emits light in a designated direction 1040 (e.g., a direction toward the part of the user's body (e.g., the user's skin 1030) when the electronic device 600 is worn), and the emitted light may be modulated by blood flow under the user's skin 1030. The modulated light 1050 may be received by the light receiving unit 1015, as shown in FIG. 10.

Figure 11:
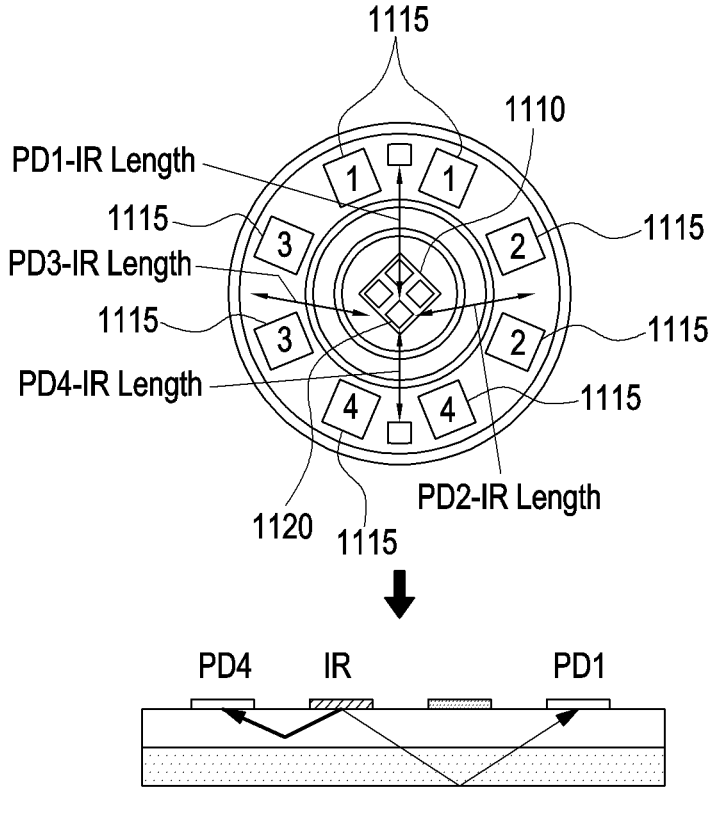
FIG. 11 is a diagram illustrating an example of an operation of measuring pressure applied to an electronic device via a PPG sensor according to an example embodiment.

FIG. 11 is a diagram illustrating an example of an operation of measuring pressure applied to an electronic device via a PPG sensor according to an embodiment.

Referring to FIG. 11, a PPG sensor included in a sensor module (e.g., a sensor module 176 in FIG. 1A, a sensor module 165 in FIG. 1B, a sensor module 610 in FIG. 6, or a sensor module 720 in FIG. 7) in an electronic device (e.g., an electronic device 101 in FIG. 1A, an electronic device 101b in FIG. 1B to FIG. 1D, an electronic device 600 in FIG. 6, or an electronic device 700 in FIG. 7) may include a light emitting unit 1110 (e.g., a light emitting unit 910 in FIG. 9) and a light receiving unit 1115 (e.g., a light receiving unit 915 in FIG. 9). In an embodiment, pressure applied to the electronic device for each channel (e.g., for each PD channel) may be measured based on a distance difference between the light emitting unit 1110 and the light receiving unit 1115. In an embodiment, a PD channel may be a signal, a path, and/or intensity of light received in a PD included in the PD channel. The PD channel may include at least one PD, and the number of PDs included in the PD channel may be variable. The PPG sensor may calculate amount of light received in each PD channel.

In FIG. 11, the light emitting unit 1110 may include at least one of a RED LED, a GREEN LED, a BLUE LED, and/or an IR LED 1120, and may generate IR light via the IR LED 1120. The light receiving unit 1115 may include two PDs corresponding to a PD channel 1, two PDs corresponding to a PD channel 2, two PDs corresponding to a PD channel 3, and two PDs corresponding to a PD channel 4. In FIG. 11, a case in which two PDs are included in one PD channel is exemplified, so two PDs may be mapped to each PD channel, and a channel number of a corresponding channel is shown in PDs mapped to the corresponding channel.

As shown in FIG. 11, it may be seen that there is a difference in an obtained DC value according to a distance between the IR LED 1120 and a PD. In FIG. 11, it may be seen that a distance (PD1-IR Length) between the IR LED 1120 and the PD channel 1 is the longest among a distance (PD2-IR Length) between the IR LED 1120 and the PD channel 2, a distance (PD3-IR Length) between the IR LED 1120 and the PD channel 3, and a distance (PD4-IR Length) between the IR LED 1120 and the PD channel 4. In an embodiment, the shorter a distance between the IR LED 1120 and the PD channel is, the greater a DC value obtained via the corresponding PD channel may be. In FIG. 11, a case in which the light emitting unit 1110 generates the IR light via the IR LED 1120 has been described as an example, however, the light emitting unit 1110 may also generate light (e.g., RED light, GREEN light, and/or BLUE light) other than the IR light.

Figure 12:
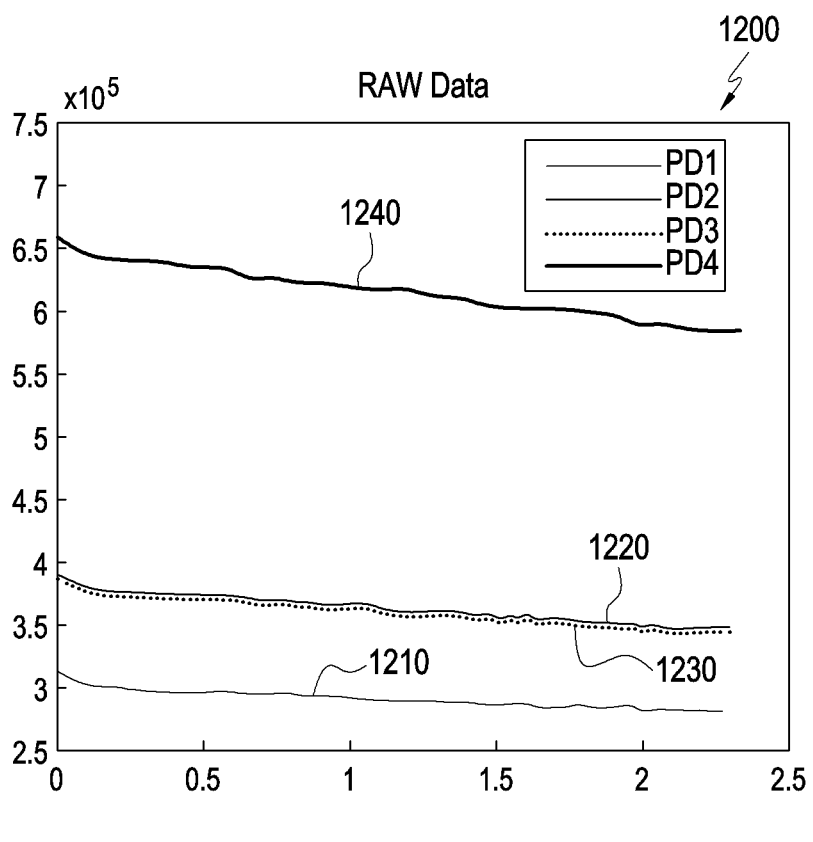
FIG. 12 is a diagram illustrating an example of a DC component value of an IR PPG signal for each PD channel obtained via a PPG sensor according to an example embodiment.

FIG. 12 is a diagram illustrating an example of a DC component value of an IR PPG signal for each PD channel obtained via a PPG sensor according to an embodiment.

Referring to FIG. 12, as described in FIG. 11, a PPG sensor included in a sensor module (e.g., a sensor module 176 in FIG. 1A, a sensor module 165 in FIG. 1B, a sensor module 610 in FIG. 6, or a sensor module 720 in FIG. 7) in an electronic device (e.g., an electronic device 101 in FIG. 1A, an electronic device 101b in FIG. 1B to FIG. 1D, an electronic device 600 in FIG. 6, or an electronic device 700 in FIG. 7) may include a light emitting unit (e.g., a light emitting unit 910 in FIG. 9 or a light emitting unit 1110 in FIG. 11) and a light receiving unit (e.g., a light receiving unit 915 in FIG. 9 or a light receiving unit 1115 in FIG. 11). The light emitting unit may include at least one of a RED LED, a GREEN LED, a BLUE LED, and/or an IR LED (e.g., an IR LED 1120 in FIG. 11), and may generate an IR light via the IR LED 1120. The light receiving unit may include two PDs corresponding to a PD channel 1, two PDs corresponding to a PD channel 2, two PDs corresponding to a PD channel 3, and two PDs corresponding to a PD channel 4.

As described in FIG. 11, a distance (PD1-IR Length) between the IR LED 1120 and the PD channel 1 may be the longest among a distance (PD2-IR Length) between the IR LED 1120 and the PD channel 2, a distance (PD3-IR Length) between the IR LED 1120 and the PD channel 3, and a distance (PD4-IR Length) between the IR LED 1120 and the PD channel 4.

In this case, as shown in a graph 1200 in FIG. 12, it may be seen that a magnitude of raw data (e.g., raw data of a DC component value of an IR PPG signal) 1240 obtained through the PD channel 4 is greater than a magnitude of raw data 1210 obtained through the PD channel 1, a magnitude of raw data 1220 obtained through the PD channel 2, and a magnitude of raw data 1230 obtained through the PD channel 3. As described in FIG. 11, a distance between the PD channel 2 and the IR LED 1120 and a distance between the PD channel 3 and the IR LED 1120 may be the same, so the magnitude of the raw data 1220 obtained through the PD channel 2 and the magnitude of the raw data 1230 obtained through the PD channel 3 may be almost similar. In this case, as shown in the graph 1200 in FIG. 12, the raw data 1220 obtained through the PD channel 2 and the raw data 1230 obtained through the PD channel 3 may be seen as overlapping each other.

Figure 13:
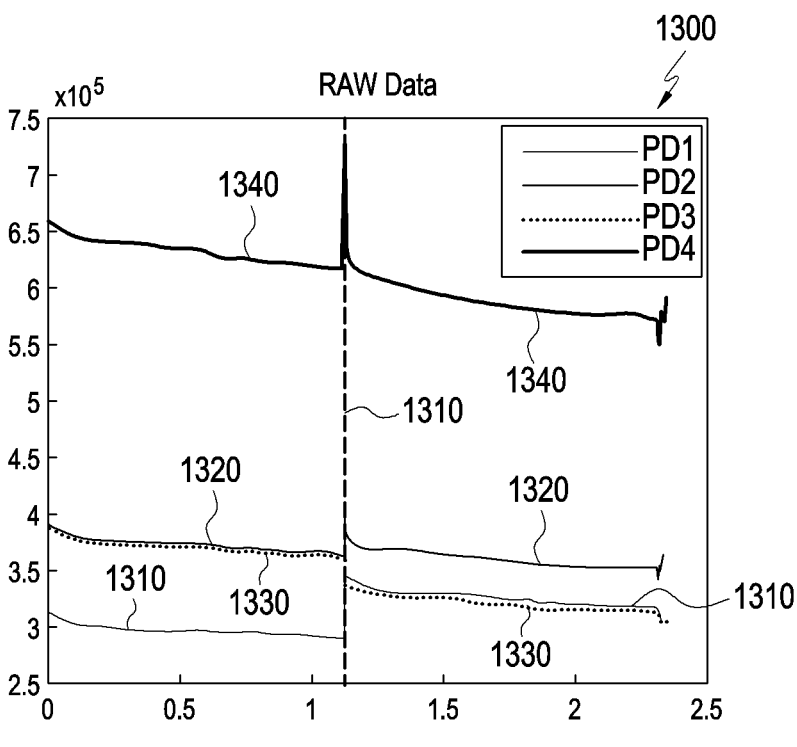
FIG. 13 is a diagram illustrating an example of a change amount of a DC component value of an IR PPG signal for each PD channel obtained via a PPG sensor according to an example embodiment.
Figure 13:
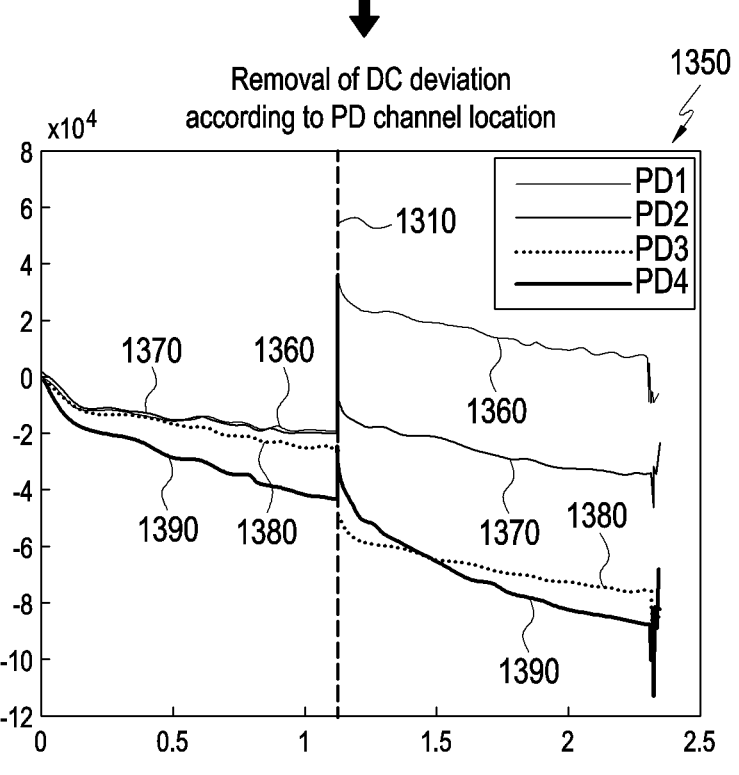

FIG. 13 is a diagram illustrating an example of a change amount of a DC component value of an IR PPG signal for each PD channel obtained via a PPG sensor according to an embodiment.

Referring to FIG. 13, as described in FIG. 11, a PPG sensor included in a sensor module (e.g., a sensor module 176 in FIG. 1A, a sensor module 165 in FIG. 1B, a sensor module 610 in FIG. 6, or a sensor module 720 in FIG. 7) in an electronic device (e.g., an electronic device 101 in FIG. 1A, an electronic device 101b in FIG. 1B to FIG. 1D, an electronic device 600 in FIG. 6, or an electronic device 700 in FIG. 7) may include a light emitting unit (e.g., a light emitting unit 910 in FIG. 9 or a light emitting unit 1110 in FIG. 11) and a light receiving unit (e.g., a light receiving unit 915 in FIG. 9 or a light receiving unit 1115 in FIG. 11), and the light emitting unit may include at least one of a RED LED, a GREEN LED, a BLUE LED, and/or an IR LED (e.g., an IR LED 1120 in FIG. 11), and may generate an IR light via the IR LED 1120. The light receiving unit may include two PDs corresponding to a PD channel 1, two PDs corresponding to a PD channel 2, two PDs corresponding to a PD channel 3, and two PDs corresponding to a PD channel 4.

As described in FIG. 11, a distance (PD1-IR Length) between the IR LED 1120 and the PD channel 1 may be the longest among a distance (PD2-IR Length) between the IR LED 1120 and the PD channel 2, a distance (PD3-IR Length) between the IR LED 1120 and the PD channel 3, and a distance (PD4-IR Length) between the IR LED 1120 and the PD channel 4. In this case, as shown in a graph 1300 in FIG. 13, it may be seen that a magnitude of raw data (e.g., raw data of a DC component value of an IR PPG signal) 1340 obtained through the PD channel 4 is greater than a magnitude of raw data 1310 obtained through the PD channel 1, a magnitude of raw data 1320 obtained through the PD channel 2, and a magnitude of raw data 1330 obtained through the PD channel 3. As described in FIG. 11, a distance between the PD channel 2 and the IR LED 1120 and a distance between the PD channel 3 and the IR LED 1120 may be the same, so the magnitude of the raw data 1320 obtained through the PD channel 2 and the magnitude of the raw data 1330 obtained through the PD channel 3 may be almost similar. In this case, as shown in the graph 1300 in FIG. 13, the raw data 1320 obtained through the PD channel 2 and the raw data 1330 obtained through the PD channel 3 may be seen as overlapping each other. In the graph 1300, a vertical axis may indicate a magnitude of a DC component value of an IR PPG signal, and a horizontal axis may indicate time. For example, the DC component value of the IR PPG signal may be a value expressed in a form of an analog to digital converter (ADC) value.

Thereafter, if force is applied to the electronic device in an F direction (e.g., a direction from the PD channel 4 to the PD channel 1 in FIG. 11) from a horizontal direction (for example, if the electronic device is pushed in the F direction from the horizontal direction), as shown in the graph 1300, it may seen that the raw data 1310, 1320, 1330, and 1340 obtained through the PD channel 1, the PD channel 2, the PD channel 3, and the PD channel 4 change from a corresponding time point 1310. In an embodiment, the horizontal direction to the electronic device may be a direction horizontal to a direction of a front surface (e.g., 901a in FIG. 9) or a rear surface (e.g., 901b in FIG. 9) of the electronic device.

As such, if the force is applied to the electronic device in the F direction from the horizontal direction, as shown in a graph 1350, it may seen that data 1360, 1370, 1380, and 1390 (e.g., a DC component of an IR PPG signal which is generated by removing DC deviation from raw data of a DC component value of the IR PPG signal) which is generated by removing DC deviation from the raw data obtained through the PD channel 1, the PD channel 2, the PD channel 3, and PD the channel 4 may also change after the corresponding time point 1310. A scheme of removing the DC deviation from the raw data obtained through the PD channel 1, the PD channel 2, the PD channel 3, and the PD channel 4 may include any one of general DC deviation removing schemes.

As described in FIG. 11, even though the distance between the PD channel 2 and the IR LED 1120 and the distance between the PD channel 3 and the IR LED 1120 are the same, if force is applied to the electronic device in the F direction from the horizontal direction, a magnitude of the raw data obtained through the PD channel 2 and a magnitude of the raw data obtained through the PD channel 3 may change after the corresponding time point 1310, so, as shown in FIG. 13, it may seen that a magnitude of the data 1370 which is generated by removing the DC deviation from the raw data 1320 obtained through the PD channel 2 is significantly different from a magnitude of the data 1380 which is generated by removing the DC deviation from the raw data 1330 obtained through the PD channel 3.

Figure 14:
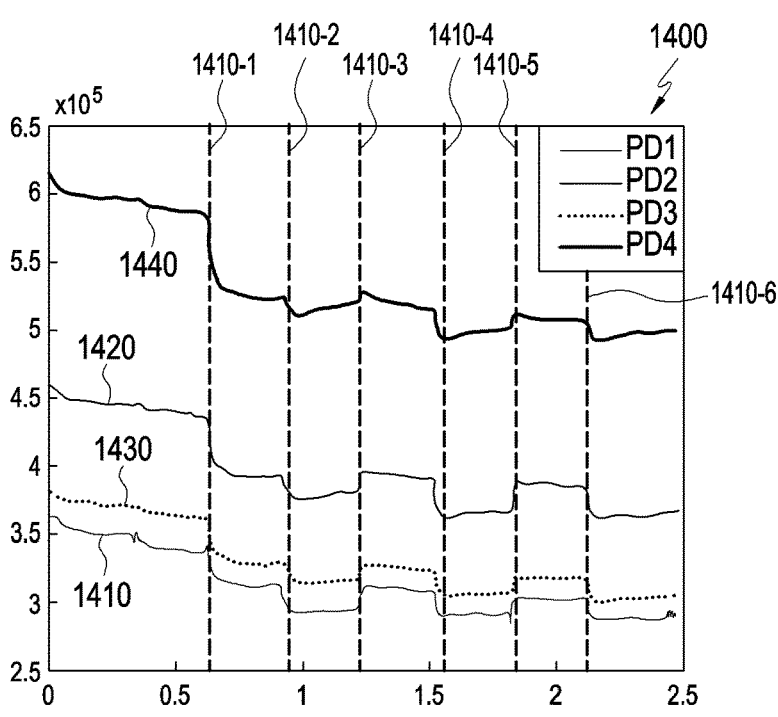
FIG. 14 is a diagram illustrating another example of a change amount of a DC component value of an IR PPG signal for each PD channel obtained via a PPG sensor according to an example embodiment.
Figure 14:
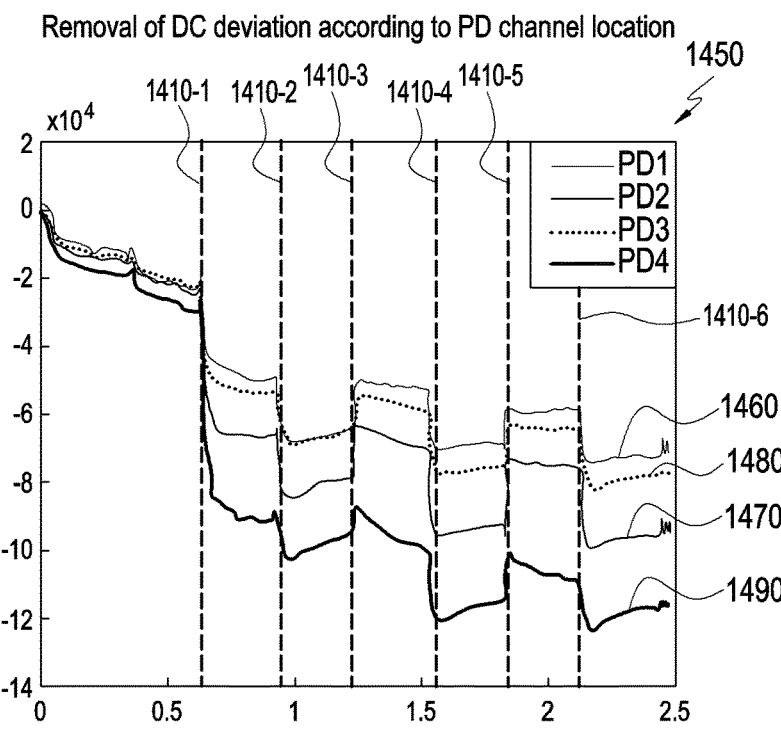

FIG. 14 is a diagram illustrating another example of a change amount of a DC component value of an IR PPG signal for each PD channel obtained via a PPG sensor according to an embodiment.

Referring to FIG. 14, as described in FIG. 11, a PPG sensor included in a sensor module (e.g., a sensor module 176 in FIG. 1A, a sensor module 165 in FIG. 1B, a sensor module 610 in FIG. 6, or a sensor module 720 in FIG. 7) in an electronic device (e.g., an electronic device 101 in FIG. 1A, an electronic device 101b in FIG. 1B to FIG. 1D, an electronic device 600 in FIG. 6, or an electronic device 700 in FIG. 7) may include a light emitting unit (e.g., a light emitting unit 910 in FIG. 9 or a light emitting unit 1110 in FIG. 11) and a light receiving unit (e.g., a light receiving unit 915 in FIG. 9 or a light receiving unit 1115 in FIG. 11), and the light emitting unit may include at least one of a RED LED, a GREEN LED, a BLUE LED, and/or an IR LED (e.g., an IR LED 1120 in FIG. 11), and may generate an IR light via the IR LED 1120. The light receiving unit may include two PDs corresponding to a PD channel 1, two PDs corresponding to a PD channel 2, two PDs corresponding to a PD channel 3, and two PDs corresponding to a PD channel 4.

As described in FIG. 11, a distance (PD4-IR Length) between the IR LED 1120 and the PD channel 4 may be the shortest among a distance (PD1-IR Length) between the IR LED 1120 and the PD channel 1, a distance (PD2-IR Length) between the IR LED 1120 and the PD channel 2, and a distance (PD3-IR Length) between the IR LED 1120 and the PD channel 3. In this case, as shown in a graph 1400 in FIG. 14, it may be seen that a magnitude of raw data (e.g., raw data of a DC component value of an IR PPG signal) 1440 obtained through the PD channel 4 is greater than a magnitude of raw data 1410 obtained through the PD channel 1, a magnitude of raw data 1420 obtained through the PD channel 2, and a magnitude of raw data 1430 obtained through the PD channel 3. In the graph 1300, a vertical axis may indicate a magnitude of a DC component value of an IR PPG signal, and a horizontal axis may indicate time. For example, the DC component value of the IR PPG signal may be a value expressed in a form of an ADC value.

Thereafter, if force is applied to the electronic device in an F direction from a vertical direction (e.g., a direction to a light emitting unit 1110 in FIG. 11) (for example, if the electronic device is pressed in the F direction from the vertical direction at a time point 1410-1), as shown in the graph 1400, it may seen that the raw data 1410, 1420, 1430, and 1440 obtained through the PD channel 1, the PD channel 2, the PD channel 3, and the PD channel 4 change at time points 1410-1 to 1410-6 compared to before the force is applied. In an embodiment, the vertical direction to the electronic device may be a direction vertical to a direction of a front surface (e.g., 901a in FIG. 9) or a rear surface (e.g., 901b in FIG. 9) of the electronic device.

As such, if the force is applied to the electronic device in the F direction from the vertical direction, as shown in a graph 1450, it may seen that data 1460, 1470, 1480, and 1490 (e.g., a DC component of an IR PPG signal which is generated by removing DC deviation from raw data of a DC component value of the IR PPG signal) which is generated by removing DC deviation from the raw data obtained through the PD channel 1, the PD channel 2, the PD channel 3, and PD the channel 4 may also change at the time points 1410-1 to 1410-6. A scheme of removing the DC deviation from the raw data obtained through the PD channel 1, the PD channel 2, the PD channel 3, and the PD channel 4 may include any one of general DC deviation removing schemes.

As described in FIG. 11, if the distance between the PD channel 2 and the IR LED 1120 and the distance between the PD channel 3 and the IR LED 1120 are the same, and before the force is applied (e.g., before the time point 1410-1), a magnitude of the data 1470 which is generated by removing the DC deviation from the raw data obtained through the PD channel 2 and a magnitude of the data 1480 which is generated by removing the DC deviation from the raw data obtained through the PD channel 3 may be similar to each other. Thereafter, if force is applied to the electronic device in the F direction from the vertical direction, a magnitude of the raw data obtained through the PD channel 2 and a magnitude of the raw data obtained through the PD channel 3 may change at the corresponding time points 1410-1 to 1410-6, so, as shown in FIG. 14, it may seen that a magnitude of the data 1470 which is generated by removing the DC deviation from the raw data 1420 obtained through the PD channel 2 is significantly different from a magnitude of the data 1480 which is generated by removing the DC deviation from the raw data 1430 obtained through the PD channel 3.

Referring back to FIG. 8, in an embodiment, the wearing state signal may be a pressure signal obtained via the pressure sensor included in the sensor module. In an embodiment, the processor may identify pressure applied between the electronic device and the part of the user's body (e.g., the user's wrist) based on the pressure signal obtained via the pressure sensor.

In an embodiment, the wearing state signal may be an ECG signal obtained via the ECG sensor included in the sensor module. In an embodiment, the processor may identify a direction in which the electronic device is in contact with the part of the user's body (e.g., the user's wrist) based on the ECG signal obtained through the ECG sensor. For example, the processor may identify whether the electronic device is in contact with a upper part of the user's wrist or a lower part of the user's wrist based on the ECG signal obtained via the ECG sensor.

For convenience of a description, a case in which the wearing state signal includes the PPG signal, the pressure signal, and the ECG signal will be described as an example. In an embodiment, the wearing state of the electronic device may be identified based on the wearing state signal, and information indicating the wearing state of the electronic device may be the wearing state information.

In an embodiment, the wearing state information may indicate a plurality of wearing states. For example, the wearing state information may indicate various wearing states which are based on information indicated by the PPG signal, the pressure signal, and the ECG signal. In addition, R-Curves corresponding to a plurality of wearing state information may be generated and stored in a memory (e.g., a memory 130 in FIG. 1A).

In an embodiment, wearing state information corresponding to each of the plurality of wearing states may exist, and an R-Curve corresponding to each of the plurality of wearing state information may be generated. In an embodiment, it will be assumed that there may be a total of N pieces of wearing state information, and in this case, an R-Curve corresponding to each of the total N pieces of wearing state information may be generated. In an embodiment, an R-Curve may be a group including pairs of an R value and SpO2. In an embodiment, a correlation between the R value and the SpO2 may be indicated by taking the R-Curve as an example, but the correlation between the R value and the SpO2 may be indicated as/via a table including the pairs of the R value and the SpO2. In an embodiment, the plurality of R-Curves may be updated if necessary. In an embodiment, a unique ID (or index) may be allocated to each of the plurality of R-Curves. In an embodiment, a unique ID (or index) may be allocated to each of a plurality of tables. For example, N R-Curves may be stored in the memory at a time point of manufacturing the electronic device. In an embodiment, if the N R-Curves are not stored in the memory at the time point of manufacturing the electronic device, the processor in the electronic device may receive, from a server (e.g., a server 108 in FIG. 1A or a server 1800 in FIG. 18) via the communication circuit, N pieces of wearing state information and N R-Curves corresponding thereto. The server may store the N pieces of wearing state information and the N R-Curves corresponding thereto, and update the N pieces of wearing state information corresponding to the N R-Curves if necessary (e.g., according to a request from the electronic device).

Referring back to FIG. 8, after identifying the wearing state information in operation 815, the processor in the electronic device may determine whether there is an R-Curve which corresponds to the wearing state information identified in operation 815 among the N R-Curves stored in the memory (e.g., the memory 130 in FIG. 1A or the memory 630 in FIG. 6) in operation 817. For example, the N R-Curves stored in the memory may be that stored in the memory at the time point of manufacturing the electronic device, or may be that received from the server and stored in the memory, and there is no limitation on a time point at which the N R-Curves are stored in the memory or a form in which the N R-Curves are stored in the memory.

In an embodiment, the processor may use a weight value when determining whether there is the R-Curve corresponding to the wearing state information identified in operation 815 among the N R-Curves. For example, there is wear state information mapped to each of the N R-Curves, so N wear state information may exist. In an embodiment, the processor may set a weight for each of information elements included in wearing state information based on a characteristic of the at least one sensor included in the sensor module.

In an embodiment, if the wearing state information includes three information elements, a weight may be set for each of the three information elements. For example, if the three information elements include pressure applied between the electronic device and the part of the users body, a size of an area in which the electronic device is in contact with the part of the users body, and a direction in which the electronic device is in contact with the part of the user's body, a weight may be set for each of the three information elements.

In an embodiment, the information elements included in the wearing state information identified in operation 815 may have a different degree of similarity (e.g., a matching rate) from information elements included in each of the N pieces of wearing state information, and a final matching rate for each of the N pieces of wearing state information may be identified by multiplying a matching rate identified for the information elements included in each of the N pieces of wearing state information by a weight set for a corresponding information element and summing them. The processor may select an R-Curve mapped to wearing state information having a final matching rate having a maximum value from among final matching rates for the N pieces of wearing state information as an R-Curve which corresponds to the wearing state information identified in operation 815. In an embodiment, if the maximum value among the final matching rates for the N pieces of wearing state information is less than a threshold value, it may be determined that there is no R-Curve corresponding to the wearing state information identified in operation 815. In an embodiment, the threshold value may be a minimum and/or small value which needs to be satisfied so that it may be determined that the identified wearing state information matches the N pieces of wearing state information mapped to the N R-Curves. In operation 815, the matching rate between the information elements included in the identified wearing state information and the information elements included in each of the N pieces of wearing state information has been considered as an example, however, there is no limitation on a form capable of indicating a degree of similarity between the information elements included in the identified wearing state information and the information elements included in each of the N pieces of wearing state information.

A scheme of selecting an R-Curve which corresponds to wearing state information from among a plurality of R-Curves according to an embodiment will be described in more detail with reference to FIG. 15.

Figure 15:
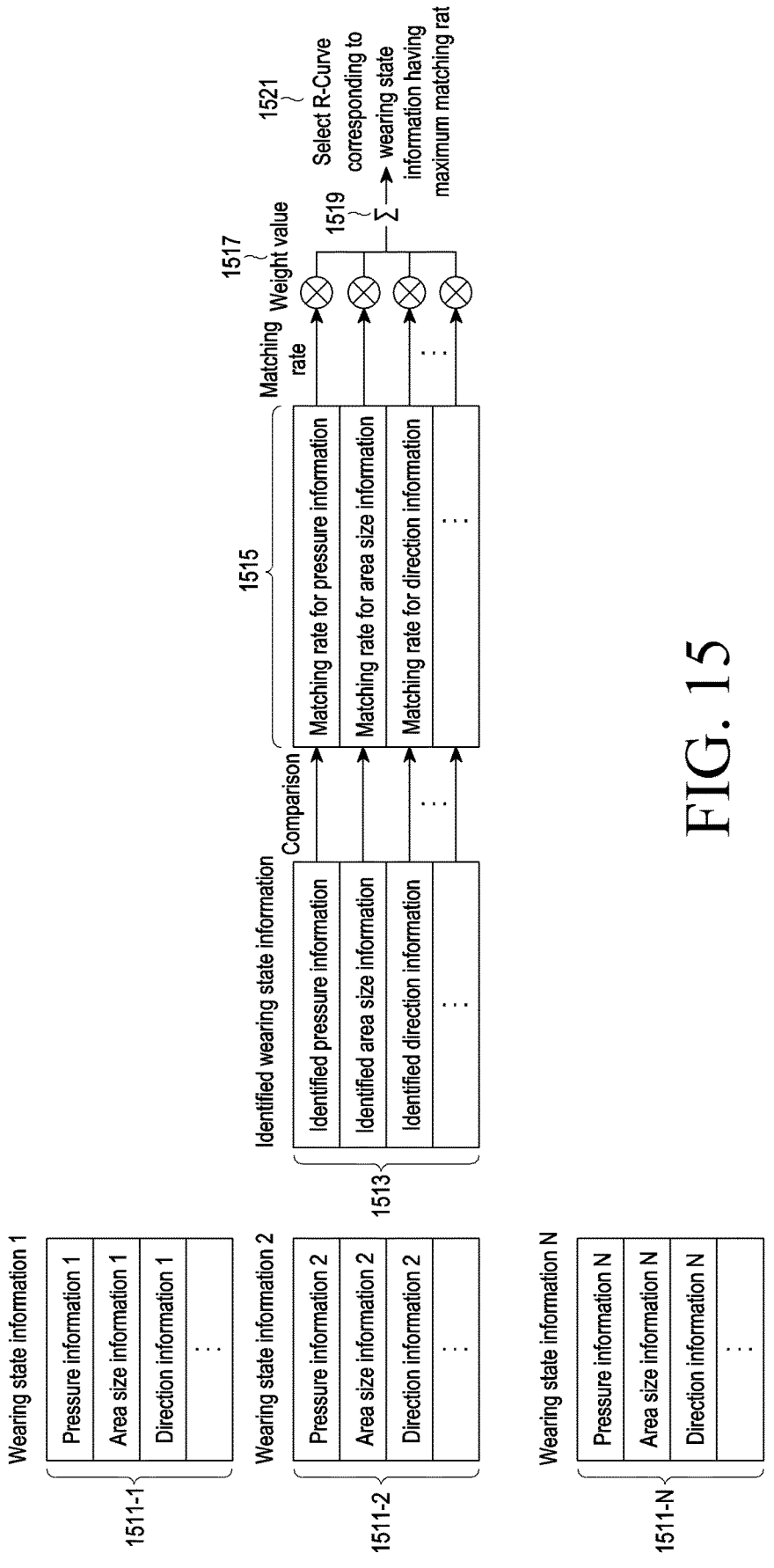
FIG. 15 is a flowchart illustrating an example of an operation of selecting an R-Curve corresponding to wearing state information from among a plurality of R-Curves according to an example embodiment.

FIG. 15 is a flowchart illustrating an example of an operation of selecting an R-Curve corresponding to wearing state information from among a plurality of R-Curves according to an embodiment.

Referring to FIG. 15, a processor (e.g., a processor 120 in FIG. 1A, a processor 620 in FIG. 6, or a processor 710 in FIG. 7) in an electronic device (e.g., an electronic device 101 in FIG. 1A, an electronic device 101b in FIG. 1B to FIG. 1D, an electronic device 600 in FIG. 6, or an electronic device 700 in FIG. 7) may store a plurality of (e.g., N) R-Curves in a memory (e.g., a memory 130 in FIG. 1A or a memory 630 in FIG. 6). For example, the N R-Curves stored in the memory may be that stored in the memory at the time point of manufacturing the electronic device, or may be that received from the server and stored in the memory, and there is no limitation on a time point at which the N R-Curves are stored in the memory or a form in which the N R-Curves are stored in the memory.

According to an embodiment, wearing state information 1511-1, 1511-2, . . . 1511-N is mapped to the N R-Curves. In an embodiment, the wearing state information may include, as information elements, pressure applied between the electronic device and a part of a user's body, a size of an area in which the electronic device is in contact with the part of the user's body, and a direction in which the electronic device is in contact with the part of the user's body.

Wearing state information 1 1511-1 may be mapped to an R-Curve 1, wearing state information 2 1511-2 may be mapped to an R-Curve 2, and in this way, wearing state information N 1511-N may be mapped to an R-Curve N. The processor may obtain a wearing state signal via a sensor module (e.g., a sensor module 176 in FIG. 1A, a sensor module 165 in FIG. 1B, a sensor module 610 in FIG. 6, or a sensor module 720 in FIG. 7) in a Continuous SpO2 measuring mode, and identify wearing state information 1513 which corresponds to the wearing state signal. The processor may compare (1515) information elements included in the identified wearing state information 1513 and information elements included in each of wearing state information 1511-1, 1511-2 . . . , 1511-N mapped to the N R-Curves to identify degrees of similarity (e.g., matching rates) between the information elements included in the identified wearing state information 1513 and the information elements included in each of the wearing state information 1511-1, 1511-2, . . . , 1511-N mapped to the N R-Curves. Then, the processor may identity a final matching rate for each of the N pieces of wearing state information 1511-1, 1511-2, . . . , 1511-N by multiplying (1517) the identified mating rates of the information elements by a weight set for each information element and summing (1519) them. The processor may select (1521) an R-Curve mapped to wearing state information having a final matching rate having a maximum from among the final matching rates for the N pieces of wearing state information 1511-1, 1511-2, . . . , 1511-N as an R-Curve which corresponds to the identified wearing state information. In an embodiment, if the maximum value from among the final matching rates for the N pieces of wearing state information is less than a threshold value, it may be determined that the R-Curve corresponding to the identified wearing state information does not exist. In an embodiment, the threshold value may be a minimum and/or small value which needs to be satisfied so that it may be determined that the identified wearing state information matches the N pieces of wearing state information mapped to the N R-Curves. In FIG. 15, the matching rate between the information elements included in the identified wearing state information and the information elements included in each of the N pieces of wearing state information has been considered as an example, however, there is no limitation on a form capable of indicating a degree of similarity between the information elements included in the identified wearing state information and the information elements included in each of the N pieces of wearing state information.

Referring back to FIG. 8, as a result of identifying in operation 817, if the R-Curve corresponding to the wearing state information identified in operation 815 exists from among the N R-curves (Operation 817—Yes), the processor in the electronic device may select the R-Curve corresponding to the wearing state information identified in operation 815 from among the N R-Curves as an R-Curve to be used for SpO2 measurement, and start an SpO2 measuring operation based on the selected R-Curve in operation 819.

As the SpO2 measuring operation is started in this way, the processor may obtain an R value based on a PPG signal obtained via the sensor module, and may measure SpO2 based on the selected R-Curve and the obtained R value. Although not shown in FIG. 8, the processor may selectively (e.g., according to the user's request, a time point at which the Continuous SpO2 measurement mode is terminated, or a set period) output the measured SpO2 via a display (e.g., a display module 160 in FIG. 1A or a display 640 in FIG. 6). An operation of measuring the SpO2 based on the selected R-Curve and the obtained R value is similar to a method described in FIG. 4, so a detailed description thereof will be omitted herein.

In an embodiment, the N R-Curves may include at least a first R-Curve and a second R-Curve, the first R-Curve is an R-Curve which corresponds to a state in which the electronic device is worn in close contact with the part of the user's body, and the second R-Curve may be an R-Curve which corresponds to a wearing state applied when an R-Curve used in an On-demand scheme is generated. For example, if the identified wearing state corresponds to a state in which the electronic device is worn so that the electronic device is in close contact with the part of the user's body, the processor may select the first R-Curve, and measure SpO2 based on the obtained R value and the selected first R-Curve. For another example, if the identified wearing state corresponds to the wearing state applied when the R-Curve used in the On-demand scheme is generated, the processor may select the second R-Curve, and measure SpO2 based on the obtained R value and the selected second R-Curve.

Although not separately shown in FIG. 8, as the result of identifying in operation 817, if there is no R-Curve corresponding to the wearing state information identified in operation 815 among the N R-Curves (Operation 817—No), the processor may proceed to operation 811 without performing the SpO2 measuring operation. In an embodiment, the processor may output a warning message indicating that SpO2 measurement has failed via the display (e.g., the display module 160 in FIG. 1A or the display 640 in FIG. 6) and/or a speaker (e.g., a sound output module 155 in FIG. 1A) whenever it is identified that the R-Curve corresponding to the wearing state information does not exist. In an embodiment, the processor may output the warning message indicating that the SpO2 measurement has failed via the display and/or the speaker upon identifying that the R-Curve corresponding to the wearing state information does not exist during set time from a time point at which it is identified that the R-Curve corresponding to the wearing state information does not exist. In an embodiment, the set time may be set differently per electronic device.

Figure 16:
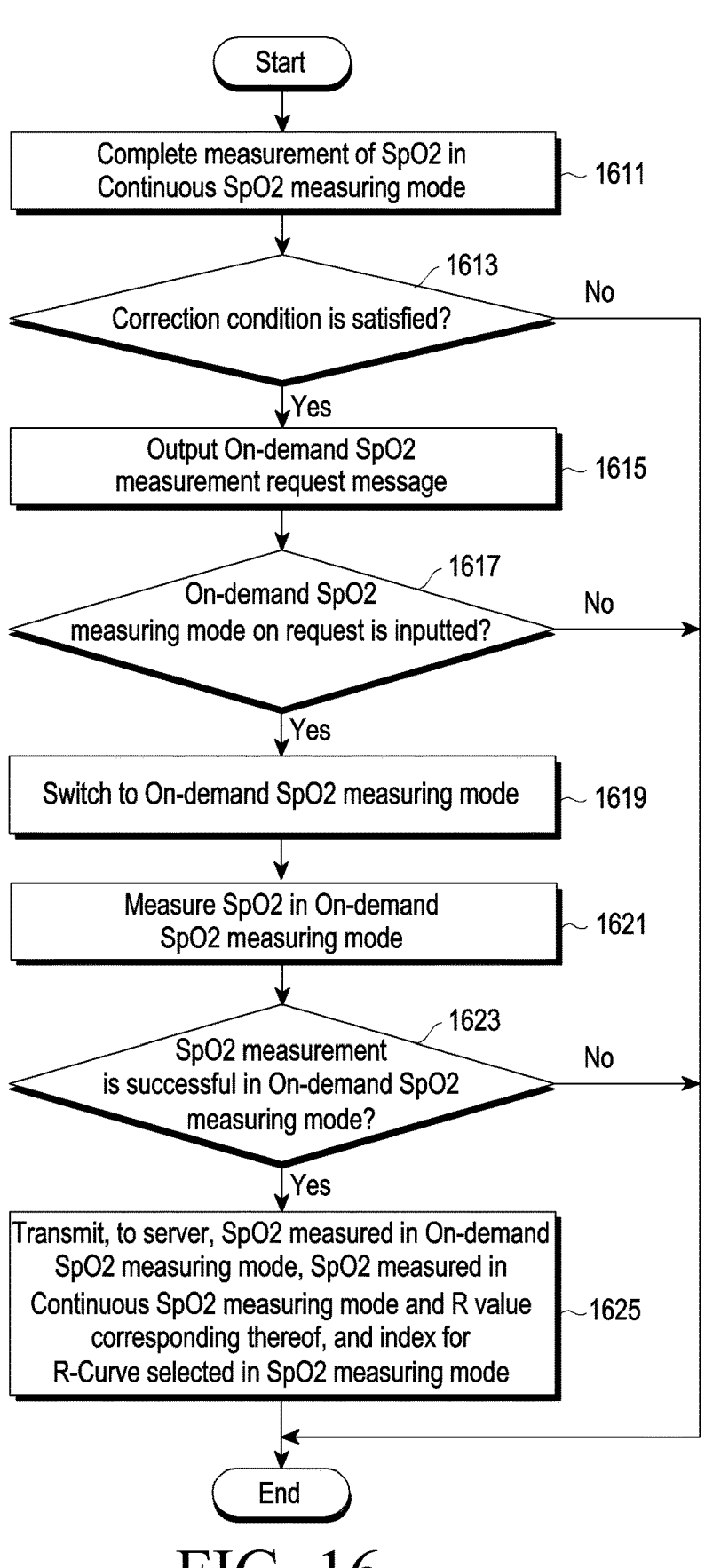
FIG. 16 is a flowchart illustrating another example of an operating process of an electronic device according to an example embodiment.

FIG. 16 is a flowchart illustrating another example of an operating process of an electronic device according to an embodiment.

Referring to FIG. 16, a processor (e.g., a processor 120 in FIG. 1A, a processor 620 in FIG. 6, or a processor 710 in FIG. 7) in an electronic device (e.g., an electronic device 101 in FIG. 1A, an electronic device 101*b* in FIG. 1B to FIG. 1D, an electronic device 600 in FIG. 6, or an electronic device 700 in FIG. 7) may complete measurement of SpO2 in a Continuous SpO2 measuring mode in operation 1611. In operation 1613, the processor may identify whether a correction condition capable of correcting a plurality of R-Curves is satisfied based on an On-demand scheme. In an embodiment, the correction condition may include at least one of the following conditions (1), (2), or (3).

(1) State in which Movement is Little

In an embodiment, a state in which movement is little may indicate a state in which movement of an electronic device obtained based on a movement signal which is obtained via a sensor module (e.g., a sensor module 176 in FIG. 1A, a sensor module 165 in FIG. 1B, a sensor module 610 in FIG. 6, or a sensor module 720 in FIG. 7) of the electronic device satisfies a set condition. In the Continuous SpO2 measuring mode, if there is little movement after the measurement of SpO2 is completed, the correction condition may be satisfied. For example, in the state in which the movement is little, a user may measure SpO2 in a stable posture, thereby accurate SpO2 measurement may be possible. In an embodiment, the movement signal may include at least one of an acceleration signal and an angular velocity signal.

In an embodiment, the set condition may be a condition which is based on at least one of a threshold value or threshold change amount of acceleration. For example, if the set condition is a condition which is based on the threshold value of acceleration, the set condition may be a condition in which an absolute DC value of the acceleration signal is less than the threshold value. As another example, if the set condition is a condition which is based on the threshold change amount of acceleration, the set condition may be a condition in which change amount of a DC value of the acceleration signal is less than the threshold change amount. In an embodiment, the set condition may be a condition which is based on at least one of a threshold value or threshold change amount of an angular velocity. For example, if the set condition is a condition which is based on the threshold value of angular velocity, the set condition may be a condition in which an absolute DC value of the angular velocity signal is less than the threshold value. As another example, if the set condition is a condition which is based on the threshold change amount of angular velocity, the set condition may be a condition in which change amount of a DC value of the angular velocity signal is less than the threshold change amount.

(2) Set Time

In an embodiment, set time may be preset time. For example, in the Continuous SpO2 measuring mode, if the set time elapses from a time point at which the measurement of the SpO2 is completed, the correction condition may be satisfied. For another example, in the Continuous SpO2 measuring mode, if time designated by the user as sleep time elapses after the measurement of the SpO2 is completed, the correction condition may be satisfied.

(3) State in which a Sudden Change in SpO2 does not Occur

If change amount of SpO2s measured in the Continuous SpO2 measuring mode is less than threshold change amount, it may be a state in which a sudden change in SpO2 does not occur. If the change amount of SpO2s measured in the Continuous SpO2 measuring mode exists within a threshold range, it may be the state in which the sudden change in SpO2 does not occur. As such, if the change amount of SpO2 measured in the Continuous SpO2 measuring mode is less than the threshold change amount or exists within the threshold range, the correction condition may be satisfied.

In an embodiment, the correction condition may be a condition for correcting R-Curves used in the Continuous SpO2 measuring mode in a situation in which it may be determined that the SpO2 measured in the Continuous SpO2 measuring mode has relatively high accuracy.

As a result of identifying in operation 1613, if the correction condition is satisfied (Operation 1613—Yes), the processor may output an On-demand SpO2 measurement request message for requesting On-demand SpO2 measurement through a UI via a display (e.g., a display module 160 in FIG. 1A or a display 640 in FIG. 6) and/or a speaker (e.g., a sound output module 155 in FIG. 1A) in operation 1615. As the result of identifying in operation 1613, if the correction condition is not satisfied (Operation 1613—No), the processor may terminate without performing any further operations.

In operation 1617, the processor may identify whether an On-demand SpO2 measuring mode on request for requesting to turn on the On-demand SpO2 measuring mode is inputted through the UI. As a result of identifying in operation 1617, if the On-demand SpO2 measuring mode on request is inputted (Operation 1617—Yes), the processor may switch an SpO2 measuring mode from the Continuous SpO2 measuring mode to the On-demand SpO2 measuring mode in operation 1619. As the result of identifying in operation 1617, if the On-demand SpO2 measuring mode on request is not inputted (Operation 1617—No), the processor may terminate without performing any further operations.

In operation 1621, the processor may measure SpO2 in the On-demand SpO2 measuring mode based on a biometric signal (e.g., an R value) obtained via the sensor module and an R-Curve (e.g., a reference R-Curve) set for the On-demand SpO2 measuring mode. In operation 1623, the processor may identify whether SpO2 measurement in the On-demand SpO2 measuring mode is successful. In an embodiment, if the processor identifies that movement occurs while measuring the SpO2 in the On-demand SpO2 measuring mode, if the processor identifies a unmeasurable state due to an unstable posture of the user, or if the biometric signal inputted form the sensor module in the On-demand SpO2 measuring mode is inaccurate, the processor may identify that the SpO2 measurement in the On-demand SpO2 measuring mode has failed.

As a result of identifying in operation 1623, if the SpO2 measurement is successful in the On-demand SpO2 measuring mode (operation 1623—Yes), the processor may transmit, to a server (e.g., a server 108 in FIG. 1A or a server 1800 in FIG. 18) via a communication circuit (e.g., a communication module 190 in FIG. 1A or a communication circuit in FIG. 6), the SpO2 measured in the On-demand SpO2 measuring mode, SpO2 measured in the Continuous SpO2 measuring mode immediately before the On-demand SpO2 measuring mode and an R value corresponding thereof, and an index for an R-Curve selected in the Continuous SpO2 measuring mode in operation 1625. As the result of identifying in operation 1623, if the SpO2 measurement is not successful in the On-demand SpO2 measuring mode (operation 1623—No), the processor may terminate without performing any further operations.

In an embodiment, the server may correct a plurality of R-Curves used in the Continuous SpO2 measuring mode of the electronic device based on the SpO2 measured in the On-demand SpO2 measuring mode, the SpO2 measured in the Continuous SpO2 measuring mode immediately before the On-demand SpO2 measuring mode and the R value corresponding thereof, and the index for the R-Curve selected in the Continuous SpO2 measuring mode which are received from the electronic device. This will be described with reference to FIG. 17.

Figure 17:
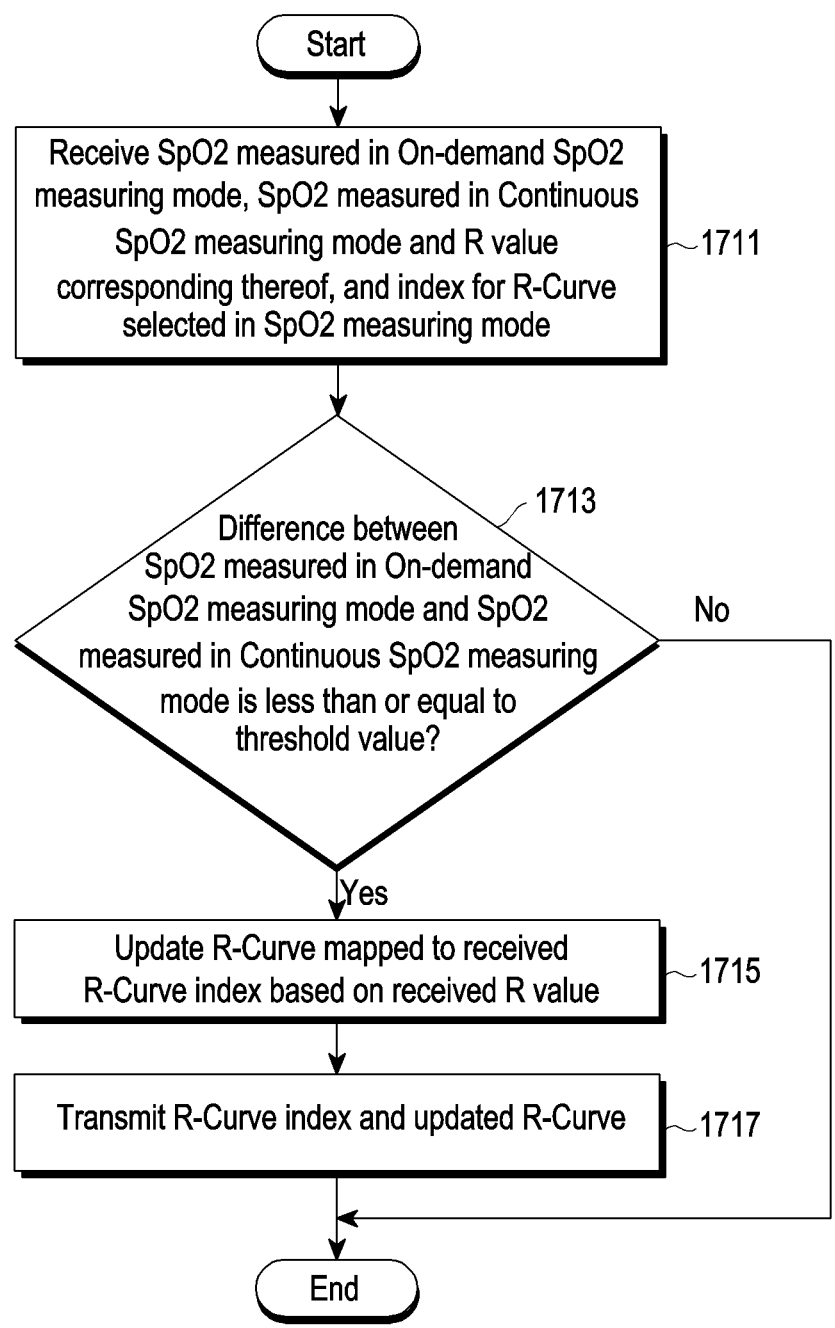
FIG. 17 is a flowchart illustrating an operating process of a server according to an example embodiment.

FIG. 17 is a flowchart illustrating an operating process of a server according to an embodiment.

Referring to FIG. 17, in operation 1711, a processor (e.g., a processor 1804 in FIG. 18) in a server (e.g., a server 108 in FIG. 1A or a server 1800 in FIG. 18) may receive, from an electronic device (e.g., an electronic device 101 in FIG. 1A, an electronic device 101b in FIG. 1B to FIG. 1D, an electronic device 600 in FIG. 6, or an electronic device 700 in FIG. 7) via a communication circuit (e.g., a communication circuit 1802 in FIG. 18), SpO2 measured in an On-demand SpO2 measuring mode, SpO2 measured in a Continuous SpO2 measuring mode immediately before the On-demand SpO2 measuring mode and an R value corresponding thereof, and an index for an R-Curve selected in the Continuous SpO2 measuring mode.

In operation 1713, the processor may identify whether a difference between SpO2 measured in the On-demand SpO2 measuring mode and SpO2 measured in the Continuous SpO2 measuring mode is equal to or less than a threshold value. As a result of identifying, if the difference between the SpO2 measured in the On-demand SpO2 measuring mode and the SpO2 measured in the Continuous SpO2 measuring mode is equal to or less than the threshold value (Operation 1713—Yes), the processor may update an R-Curve mapped to an R-Curve index by changing an R value of an R-Curve mapped to the received R-Curve index to an R value which corresponds to the received SpO2 measured in the Continuous SpO2 measuring mode in operation 1715. As a result of identifying in operation 1713, if the difference between the SpO2 measured in the On-demand SpO2 measuring mode and the SpO2 measured in the Continuous SpO2 measuring mode is not equal to or less than the threshold value (Operation 1713-No), the processor may terminate without performing any further operations. For example, if the difference between the SpO2 measured in the On-demand SpO2 measuring mode and the SpO2 measured in the Continuous SpO2 measuring mode is not equal to or less than the threshold value, inaccurate R-Curve correction may proceed, so the processor may terminate without performing any further operations.

In operation 1717, the processor may transmit the R-Curve index and the updated R-Curve to the electronic device via the communication circuit. According to an embodiment, upon receiving the R-Curve index and the updated R-Curve from the server, the electronic device may update an R-Curve which corresponds to an R-Curve index stored in the electronic device to the received updated R-Curve. As such, the updated R-Curve may then be used when SpO2 is measured in the Continuous SpO2 measuring mode, so it may be possible to measure SpO2 more suitable for a user.

In FIG. 17, a case in which an R-Curve updating operation for the electronic device is performed in the server has been described as an example, however, the electronic device (e.g., a wearable electronic device) may also perform the R-Curve updating operation directly.

FIG. 18 is a block diagram illustrating a server according to an embodiment.

Referring to FIG. 18, a server (e.g., a server 108 in FIG. 1A) may include a communication circuit 1802 for transmitting and receiving signals to and from an electronic device (e.g., an electronic device 101 in FIG. 1A, an electronic device 101b in FIG. 1B to FIG. 1D, an electronic device 600 in FIG. 6, or an electronic device 700 in FIG. 7). In an embodiment, the communication circuit 1802 may support a wired or wireless communication.

The server 1800 may include a processor 1804 which may be implemented with one or more single-core processors or one or more multi-core processors, and a memory 1806 which stores instructions for an operation of the server 1800.

The server 1800 may include an interface module 1808 which provides a wired and/or wireless interface for communicating with components outside a network.

According to an embodiment, an operating method of an electronic device (e.g., an electronic device 101 in FIG. 1A, an electronic device 101b in FIG. 1B to FIG. 1D, an electronic device 600 in FIG. 6, or an electronic device 700) may comprise, if change amount of movement of the electronic device (e.g., the electronic device 101 in FIG. 1A, the electronic device 101b in FIG. 1B to FIG. 1D, the electronic device 600 in FIG. 6, or the electronic device 700) is within a threshold range, identifying a wearing state of the electronic device (e.g., the electronic device 101 in FIG. 1A, the electronic device 101b in FIG. 1B to FIG. 1D, the electronic device 600 in FIG. 6, or the electronic device 700).

According to an embodiment, the operating method may further comprise selecting a group which corresponds to the wearing state from among a plurality of groups including a first group including saturations of percutaneous oxygen (SpO2s) which correspond to reference values based on photoplethysmogram (PPG) signals and a second group including other SpO2s which correspond to the reference values.

According to an embodiment, the operating method may comprise obtaining a first PPG signal via at least one sensor (e.g., a sensor module 176 in FIG. 1A, a sensor module 165 in FIG. 1B, a sensor module 610 in FIG. 6, or a sensor module 720 in FIG. 7) included in the electronic device (e.g., the electronic device 101 in FIG. 1A, the electronic device 101b in FIG. 1B to FIG. 1D, the electronic device 600 in FIG. 6, or the electronic device 700), and obtaining a first SpO2 using the selected group and a first reference value which is based on the first PPG signal.

According to an embodiment, selecting the group which corresponds to the wearing state from among the plurality of groups may comprise identifying a degree of similarity between wearing state information which corresponds to the identified wearing state and each of pieces of wearing state information mapped to the plurality of groups, and selecting a group mapped to wearing state information having a maximum value from among the identified degrees of similarity as a group which corresponds to the identified wearing state.

According to an embodiment, wearing state information includes at least one of pressure applied to the electronic device (e.g., the electronic device 101 in FIG. 1A, the electronic device 101b in FIG. 1B to FIG. 1D, the electronic device 600 in FIG. 6, or the electronic device 700) by a user's body, a size of an area in which the electronic device (e.g., the electronic device 101 in FIG. 1A, the electronic device 101b in FIG. 1B to FIG. 1D, the electronic device 600 in FIG. 6, or the electronic device 700) is in contact with the user's body, or a direction in which the electronic device (e.g., the electronic device 101 in FIG. 1A, the electronic device 101b in FIG. 1B to FIG. 1D, the electronic device 600 in FIG. 6, or the electronic device 700) is in contact with the user's body as information elements.

According to an embodiment, selecting the group which corresponds to the wearing state from among the plurality of groups may comprise identifying degrees of similarity between information elements included in the wearing state information which corresponds to the identified wearing state and information elements included in each of the pieces of wearing state information mapped to the plurality of groups, for each of the plurality of groups, applying a weight value set for each information element to each of the identified degrees of similarity for the information elements, and selecting, from among the plurality of groups, a group in which sum of degrees of similarity to which the weight value is applied is a maximum value as the group which corresponds to the identified wearing state.

According to an embodiment, the maximum value among sums of degrees of similarity to which the weight value is applied may be greater than or equal to a set minimum and/or low degree of similarity.

According to an embodiment, the movement may be obtained based on at least one of an acceleration signal or an angular velocity signal obtained via the at least one sensor (e.g., the sensor module 176 in FIG. 1A, the sensor module 165 in FIG. 1B, the sensor module 610 in FIG. 6, or the sensor module 720 in FIG. 7) included in the electronic device (e.g., the electronic device 101 in FIG. 1A, the electronic device 101b in FIG. 1B to FIG. 1D, the electronic device 600 in FIG. 6, or the electronic device 700).

According to an embodiment, the wearing state may be obtained based on at least one of a PPG signal, an electrocardiography (ECG) signal, and a pressure signal obtained via the at least one sensor (e.g., the sensor module 176 in FIG. 1A, the sensor module 165 in FIG. 1B, the sensor module 610 in FIG. 6, or the sensor module 720 in FIG. 7) included in the electronic device (e.g., the electronic device 101 in FIG. 1A, the electronic device 101b in FIG. 1B to FIG. 1D, the electronic device 600 in FIG. 6, or the electronic device 700).

According to an embodiment, selecting the group which corresponds to the wearing state from among the plurality of groups and obtaining the first SpO2 may comprise, if the wearing state is a wearing state in which a size of an area in which the electronic device (e.g., the electronic device 101 in FIG. 1A, the electronic device 101b in FIG. 1B to FIG. 1D, the electronic device 600 in FIG. 6, or the electronic device 700) is in contact with a user's body is larger than or equal to a threshold area, selecting the first group and obtaining the first SpO2 using the first group and the first reference value, and if the wearing state is a wearing state which is applied when a group (e.g., a single group) used in a second measuring scheme is generated, selecting the second group and obtaining the first SpO2 using the second group and the first reference value.

According to an embodiment, the second measuring scheme may be different from a first measuring scheme in which the plurality of groups are used.

According to an embodiment, the operating method may further comprise, after obtaining the first SpO2, switching from a first measuring scheme in which the plurality of groups are used to a second measuring scheme in which a group (e.g., a single group) is used.

According to an embodiment, the operating method may further comprise obtaining a second PPG signal in the second measuring scheme.

According to an embodiment, the operating method may further comprise obtaining a second SpO2 using the group (e.g., the single group) and a second reference value which is based on the second PPG signal.

According to an embodiment, the operating method may further comprise transmitting, to an external electronic device (e.g., a server 108 in FIG. 1A or a server 1800 in FIG. 18), at least one of the first SpO2, the first reference value, an identifier of the selected group, and the second SpO2 to update the selected group.

According to an embodiment, the selected group may be updated by changing the first reference value included in the selected group to the second reference value which corresponds to the second SpO2.

According to an embodiment, a measuring scheme may be switched from the first measuring scheme to the second measuring scheme if a condition is satisfied.

According to an embodiment, the condition may include at least one of a condition that change amount of the movement of the electronic device (e.g., the electronic device 101 in FIG. 1A, the electronic device 101b in FIG. 1B to FIG. 1D, the electronic device 600 in FIG. 6, or the electronic device 700) obtained via the at least one sensor (e.g., the sensor module 176 in FIG. 1A, the sensor module 165 in FIG. 1B, the sensor module 610 in FIG. 6, or the sensor module 720 in FIG. 7) included in the electronic device (e.g., the electronic device 101 in FIG. 1A, the electronic device 101b in FIG. 1B to FIG. 1D, the electronic device 600 in FIG. 6, or the electronic device 700) is within a first threshold range, a condition that set time elapses after a time point at which the measurement of the first SpO2 is completed, or a condition that change amount of SpO2s measured in the first measuring scheme is within a second threshold range.

According to an embodiment, the movement may be obtained based on at least one of an acceleration signal or an angular velocity signal obtained via the at least one sensor (e.g., the sensor module 176 in FIG. 1A, the sensor module 165 in FIG. 1B, the sensor module 610 in FIG. 6, or the sensor module 720 in FIG. 7) included in the electronic device (e.g., the electronic device 101 in FIG. 1A, the electronic device 101b in FIG. 1B to FIG. 1D, the electronic device 600 in FIG. 6, or the electronic device 700).

According to an embodiment, selecting the group which corresponds to the wearing state from among the plurality of groups may comprise identifying a degree of similarity between wearing state information which corresponds to the identified wearing state and each of pieces of wearing state information mapped to the plurality of groups, and selecting a group mapped to wearing state information having a maximum value from among the identified degrees of similarity as a group which corresponds to the identified wearing state.

According to an embodiment, wearing state information includes at least one of pressure applied to the electronic device (e.g., the electronic device 101 in FIG. 1A, the electronic device 101b in FIG. 1B to FIG. 1D, the electronic device 600 in FIG. 6, or the electronic device 700) by a user's body, a size of an area in which the electronic device (e.g., the electronic device 101 in FIG. 1A, the electronic device 101b in FIG. 1B to FIG. 1D, the electronic device 600 in FIG. 6, or the electronic device 700) is in contact with the user's body, or a direction in which the electronic device (e.g., the electronic device 101 in FIG. 1A, the electronic device 101b in FIG. 1B to FIG. 1D, the electronic device 600 in FIG. 6, or the electronic device 700) is in contact with the user's body as information elements.

According to an embodiment, selecting the group which corresponds to the wearing state from among the plurality of groups may comprise identifying degrees of similarity between information elements included in the wearing state information which corresponds to the identified wearing state and information elements included in each of the pieces of wearing state information mapped to the plurality of groups, for each of the plurality of groups, applying a weight value set for each information element to each of the identified degrees of similarity for the information elements, and selecting, from among the plurality of groups, a group in which sum of degrees of similarity to which the weight value is applied is a maximum value as the group which corresponds to the identified wearing state.

According to an embodiment, the maximum value among sums of degrees of similarity to which the weight value is applied may be greater than or equal to a set minimum degree of similarity.

According to an embodiment, identifying the wearing state of the electronic device (e.g., the electronic device 101 in FIG. 1A, the electronic device 101b in FIG. 1B to FIG. 1D, the electronic device 600 in FIG. 6, or the electronic device 700) may be performed upon identifying that change amount of the movement of the electronic device (e.g., the electronic device 101 in FIG. 1A, the electronic device 101b in FIG. 1B to FIG. 1D, the electronic device 600 in FIG. 6, or the electronic device 700) is within a first threshold range.

According to an embodiment, the movement may be obtained based on at least one of an acceleration signal or an angular velocity signal obtained via the at least one sensor (e.g., the sensor module 176 in FIG. 1A, the sensor module 165 in FIG. 1B, the sensor module 610 in FIG. 6, or the sensor module 720 in FIG. 7) included in the electronic device (e.g., the electronic device 101 in FIG. 1A, the electronic device 101*b* in FIG. 1B to FIG. 1D, the electronic device 600 in FIG. 6, or the electronic device 700).

According to an embodiment, the wearing state may be obtained based on at least one of a PPG signal, an electro-cardiography (ECG) signal, and a pressure signal obtained via the at least one sensor (e.g., the sensor module 176 in FIG. 1A, the sensor module 165 in FIG. 1B, the sensor module 610 in FIG. 6, or the sensor module 720 in FIG. 7) included in the electronic device (e.g., the electronic device 101 in FIG. 1A, the electronic device 101*b* in FIG. 1B to FIG. 1D, the electronic device 600 in FIG. 6, or the electronic device 700).

According to an embodiment, the operating method may further comprise receiving an identifier of the updated group and the updated group from the external electronic device (e.g., the server 108 in FIG. 1A or the server 1800 in FIG. 18).

According to an embodiment, if a difference between the first SpO2 and the second SpO2 is less than or equal to a threshold value, the updated group may be updated by changing the first reference valued included in the selected group to the second reference value which corresponds to the second SpO2.

According to an embodiment, selecting the group which corresponds to the wearing state from among the plurality of groups and obtaining the first SpO2 using the selected group and the first reference value which is based on the first PPG signal may comprise, if the wearing state is a wearing state in which a size of an area in which the electronic device (e.g., the electronic device 101 in FIG. 1A, the electronic device 101*b* in FIG. 1B to FIG. 1D, the electronic device 600 in FIG. 6, or the electronic device 700) is in contact with a user's body is larger than or equal to a threshold area, selecting the first group and obtaining the first SpO2 using the first group and the first reference value, and if the wearing state is a wearing state which is applied when a group (e.g., a single group) used in a second measuring scheme is generated, selecting the second group and obtain the first SpO2 using the second group and the first reference value.

According to an embodiment, the second measuring scheme may be different from a first measuring scheme in which the plurality of groups are used.

According to an embodiment, an operating method of an external electronic device (e.g., a server 108 in FIG. 1A or a server 1800 in FIG. 18) may comprise receiving, from an electronic device (e.g., an electronic device 101 in FIG. 1A, an electronic device 101*b* in FIG. 1B to FIG. 1D, an electronic device 600 in FIG. 6, or an electronic device 700), a first SpO2 obtained in a first measuring scheme in which a plurality of groups including a first group including saturations of percutaneous oxygen (SpO2s) which corre-spond to reference values based on photoplethysmogram (PPG) signals and a second group including other SpO2s which correspond to the reference values are used, a first reference value which corresponds to the first SpO2, an identifier of a group used for obtaining the first SpO2 among the plurality of groups, and a second SpO2 measured in a second measuring scheme in which a group (e.g., a single group) is used.

According to an embodiment, the operating method may comprise, if a difference between the first SpO2 and the second SpO2 is less than or equal to a threshold value, updating a group mapped to the identifier by changing the first reference value included in the group mapped to the identifier to a second reference value which corresponds to the second SpO2.

According to an embodiment, the operating method may comprise transmitting the identifier and the updated group to the electronic device (e.g., the electronic device 101 in FIG. 1A, the electronic device 101*b* in FIG. 1B to FIG. 1D, the electronic device 600 in FIG. 6, or the electronic device 700).

According to an embodiment, the group used for obtain-ing the first SpO2 may be a group mapped to wearing state information which corresponds to the wearing state of the electronic device (e.g., the electronic device 101 in FIG. 1A, the electronic device 101*b* in FIG. 1B to FIG. 1D, the electronic device 600 in FIG. 6, or the electronic device 700) identified in the first measuring scheme among the plurality of groups.

According to an embodiment, the wearing state may be obtained based on at least one of a PPG signal, an electro-cardiography (ECG) signal, or a press signal obtained via at least one sensor (e.g., a sensor module 176 in FIG. 1A, a sensor module 165 in FIG. 1B, a sensor module 610 in FIG. 6, or a sensor module 720 in FIG. 7) included in the electronic device (e.g., the electronic device 101 in FIG. 1A, the electronic device 101*b* in FIG. 1B to FIG. 1D, the electronic device 600 in FIG. 6, or the electronic device 700).

According to an embodiment, a measuring scheme of the electronic device (e.g., the electronic device 101 in FIG. 1A, the electronic device 101*b* in FIG. 1B to FIG. 1D, the electronic device 600 in FIG. 6, or the electronic device 700) may be switched from the first measuring scheme to the second measuring scheme if a condition is satisfied, and the condition may include at least one of a condition that change amount of the movement of the electronic device (e.g., the electronic device 101 in FIG. 1A, the electronic device 101*b* in FIG. 1B to FIG. 1D, the electronic device 600 in FIG. 6, or the electronic device 700) is within a first threshold range, a condition that set time elapses after a time point at which the electronic device (e.g., the electronic device 101 in FIG. 1A, the electronic device 101*b* in FIG. 1B to FIG. 1D, the electronic device 600 in FIG. 6, or the electronic device 700) completes the measurement of the first SpO2, or a condition that change amount of SpO2s measured in the first measur-ing scheme is within a second threshold range.

According to an embodiment, the movement may be obtained based on at least one of an acceleration signal or an angular velocity signal obtained via at least one sensor (e.g., a sensor module 176 in FIG. 1A, a sensor module 165 in FIG. 1B, a sensor module 610 in FIG. 6, or a sensor module 720 in FIG. 7) included in the electronic device (e.g., the electronic device 101 in FIG. 1A, the electronic device 101*b* in FIG. 1B to FIG. 1D, the electronic device 600 in FIG. 6, or the electronic device 700).

According to an embodiment, the operating method may further comprise, if the difference between the first SpO2 and the second SpO2 is greater than the threshold value, transmit a message indicating that a group update is not performed to the electronic device (e.g., the electronic device 101 in FIG. 1A, the electronic device 101*b* in FIG. 1B to FIG. 1D, the electronic device 600 in FIG. 6, or the electronic device 700).

According to an embodiment, if an electronic device (e.g., a wearable electronic device) measures SpO2 based on a Continuous scheme, a section in which inaccurate SpO2 measurement may occur may be removed, thereby increasing SpO2 accuracy.

According to an embodiment, if an electronic device (e.g., a wearable electronic device) measures SpO2 based on a Continuous scheme, a section in which inaccurate SpO2 measurement may occur may be removed, thereby increasing a success rate of SpO2 measurement.

According to an embodiment, if a state in which SpO2 measurement is impossible is identified if an electronic device (e.g., a wearable electronic device) measures SpO2 based on a Continuous scheme, SpO2 measurement is not performed, thereby preventing or reducing unnecessary current consumption.

According to an embodiment, if an electronic device (e.g., a wearable electronic device) measures SpO2 based on a Continuous scheme, R-curve accuracy may be improved through interworking with a server, thereby increasing SpO2 accuracy.

According to an embodiment, if an electronic device (e.g., a wearable electronic device) measures SpO2 based on a Continuous scheme, a probability that SpO2 is inaccurately measured due to a user's posture or the user's movement may be reduced.

The invention claimed is:

1. An electronic device comprising:
at least one sensor;
memory storing instructions;
a communication circuit; and
at least one processor comprising processing circuitry and operatively connected with the at least one sensor,
wherein the instructions, when executed by the at least one processor, individually and/or collectively, cause the electronic device to:
receive at least one of an acceleration signal or an angular velocity signal from the at least one sensor,
identify a wearing state of the electronic device via the at least one sensor, based on a change amount of movement of the electronic device, obtained based on at least one of the acceleration signal or the angular velocity signal from the at least one sensor, being within a threshold range,
select a group which corresponds to the wearing state from among a plurality of groups including a first group including saturations of percutaneous oxygen (SpO2s) which correspond to reference values and a second group including other SpO2s which correspond to the reference values,
obtain a first photoplethysmogram (PPG) signal via the at least one sensor, and obtain a first SpO2 based on the selected group and a first reference value which is based on the first PPG signal;
after obtaining the first SpO2, switch from a first measuring scheme in which the plurality of groups are to be used, to a second measuring scheme in which a single group is to be used;
obtain a second PPG signal via the at least one sensor, and obtain a second SpO2 based on the single group and a second reference value which is based on the second PPG signal in the second measuring scheme; and
control to transmit, to an external electronic device via the communication circuit, at least one of the first SpO2, the first reference value, an identifier of the selected group, and the second SpO2 to update the selected group.

2. The electronic device of claim 1, wherein the instructions, when executed by the at least one processor, individually and/or collectively, cause the electronic device to:
identify a degree of similarity between wearing state information which corresponds to the identified wearing state and each of pieces of wearing state information mapped to the plurality of groups, and
select a group mapped to wearing state information having a large and/or maximum value from among the identified degrees of similarity as a group which corresponds to the identified wearing state.

3. The electronic device of claim 2, wherein wearing state information includes at least one of: pressure applied to the electronic device by a user's body, a size of an area in which the electronic device is in contact with the user's body, or a direction in which the electronic device is in contact with the user's body as information elements, and
wherein the instructions, when executed by the at least one processor, individually and/or collectively, cause the electronic device to:
identify degrees of similarity between information elements included in the wearing state information which corresponds to the identified wearing state and information elements included in each of the pieces of wearing state information mapped to the plurality of groups,
for each of the plurality of groups, apply a weight value set for each information element to each of the identified degrees of similarity for the information elements, and
select, from among the plurality of groups, a group in which a sum of degrees of similarity to which the weight value is applied is a maximum value as the group which corresponds to the identified wearing state.

4. The electronic device of claim 3, wherein the maximum value among sums of degrees of similarity to which the weight value is applied is greater than or equal to a set minimum and/or small degree of similarity.

5. The electronic device of claim 1, wherein the movement is based on the acceleration signal and angular velocity signal obtained via the at least one sensor.

6. The electronic device of claim 1, wherein the wearing state is based on at least one of a PPG signal, an electrocardiogramaignal, and a pressure signal obtained via the at least one sensor.

7. The electronic device of claim 1, wherein the instructions, when executed by the at least one processor, individually and/or collectively, cause the electronic device to:
select the first group and obtain the first SpO2 using the first group and the first reference value based on the wearing state being a wearing state in which a size of an area in which the electronic device is in contact with a user's body is larger than or equal to a threshold area, and
select the second group and obtain the first SpO2 using the second group and the first reference value based on the wearing state being a wearing state applied when a single group used in a second measuring scheme is generated,
wherein the second measuring scheme is different from a first measuring scheme in which the plurality of groups are to be used.

8. The electronic device of claim 1,
wherein the instructions, when executed by the at least one processor, individually and/or collectively, cause the electronic device to:

receive, from the external electronic device, the updated selected group.

9. The electronic device of claim 1, wherein the selected group is to be updated by changing the first reference value included in the selected group to the second reference value which corresponds to the second SpO2.

10. The electronic device of claim 1, wherein the instructions, when executed by the at least one processor, individually and/or collectively, cause the electronic device to:

switch from the first measuring scheme to the second measuring scheme based on a condition being satisfied, and wherein the condition includes at least one of: a condition where change amount of the movement of the electronic device obtained via the at least one sensor is within a first threshold range, a condition where set time elapses after a time point at which the measurement of the first SpO2 is completed, or a condition where change amount of SpO2s measured in the first measuring scheme is within a second threshold range.

11. The electronic device of claim 1, wherein the instructions, when executed by the at least one processor, individually and/or collectively, cause the electronic device to:

identify a degree of similarity between wearing state information which corresponds to the identified wearing state and each of pieces of wearing state information mapped to the plurality of groups, and select a group mapped to wearing state information having a large and/or maximum value from among the identified degrees of similarity as a group which corresponds to the identified wearing state.

12. The electronic device of claim 11, wherein wearing state information includes at least one of: pressure applied to the electronic device by a user's body, a size of an area in which the electronic device is in contact with the user's body, or a direction in which the electronic device is in contact with the user's body as information elements, and wherein the instructions, when executed by the at least one processor, individually and/or collectively, cause the electronic device to:

identify degrees of similarity between information elements included in the wearing state information which corresponds to the identified wearing state and information elements included in each of the pieces of wearing state information mapped to the plurality of groups, for each of the plurality of groups, apply a weight value set for each information element to each of the identified degrees of similarity for the information elements, and select, from among the plurality of groups, a group in which sum of degrees of similarity to which the weight value is applied is a large and/or maximum value as the group which corresponds to the identified wearing state.

13. The electronic device of claim 12, wherein the large and/or maximum value among sums of degrees of similarity to which the weight value is applied is greater than or equal to a set minimum and/or small degree of similarity.

14. The electronic device of claim 1, wherein the instructions, when executed by the at least one processor, individually and/or collectively, cause the electronic device to:

based on identifying that change amount of the movement of the electronic device obtained via the at least one sensor is within a first threshold range, identify the wearing state for the electronic device in the first measuring scheme.

15. The electronic device of claim 1, wherein the instructions, when executed by the at least one processor, individually and/or collectively, cause the electronic device to:

receive, from the external electronic device via the communication circuit, an identifier of an updated group and the updated group, and based on a difference between the first SpO2 and the second SpO2 being less than or equal to a threshold value, update the updated group by changing the first reference value included in the selected group to the second reference value which corresponds to the second SpO2.

16. The electronic device of claim 1, wherein the instructions, when executed by the at least one processor, individually and/or collectively, cause the electronic device to:

select the first group and obtain the first SpO2 using the first group and the first reference value based on the wearing state being a wearing state in which a size of an area in which the electronic device is in contact with a user's body is larger than or equal to a threshold area, and select the second group and obtain the first SpO2 using the second group and the first reference value based on the wearing state being a wearing state which is applied when a single group used in a second measuring scheme is generated, and wherein the second measuring scheme is different from a first measuring scheme in which the plurality of groups are to be used.

17. An external electronic device comprising:

a communication circuit;

memory storing instructions; and at least one processor comprising processing circuitry and operatively connected with the communication circuit, wherein the instructions, when executed by the at least one processor, individually and/or collectively, cause the external electronic device to:

receive, from an electronic device via the communication circuit, a first SpO2 from a first measuring scheme in which a plurality of groups including a first group including saturations of percutaneous oxygen (SpO2s) which correspond to reference values based on photoplethysmogram (PPG) signals and a second group including other SpO2s which correspond to the reference values are to be used, a first reference value which corresponds to the first SpO2, an identifier of a group used for obtaining the first SpO2 among the plurality of groups, and a second SpO2 measured in a second measuring scheme in which a single group is used, update a group mapped to the identifier by changing the first reference value included in the group mapped to the identifier to a second reference value which corresponds to the second SpO2 based on a difference between the first SpO2 and the second SpO2 being less than or equal to a threshold value, and control to transmit, to the electronic device via the communication circuit, the identifier and the updated group.

18. The external electronic device of claim 17, wherein the group for obtaining the first SpO2 is a group mapped to wearing state information which corresponds to the wearing state of the electronic device identified in the first measuring scheme among the plurality of groups.

19. The external electronic device of claim 17, wherein a measuring scheme of the electronic device is to be switched from the first measuring scheme to the second measuring scheme based on a condition satisfied, and

wherein the condition includes at least one of a condition that change amount of movement of the electronic device is within a first threshold range, a condition that set time elapses after a time point at which the electronic device completes the measurement of the first SpO2, or a condition that change amount of SpO2s measured in the first measuring scheme is within a second threshold range.

20. The external electronic device of claim 17, wherein the instructions, when executed by the at least one processor individually and/or collectively, are configured to control the external electronic device to:

control to transmit, to the electronic device via the communication circuit, a message indicating that a group update is not performed based on the difference between the first SpO2 and the second SpO2 is greater than the threshold value.

\* \* \* \* \*

60